United States Patent
Wang et al.

(10) Patent No.: US 11,203,634 B2
(45) Date of Patent: Dec. 21, 2021

(54) METHODS OF TREATING AGE-RELATED MACULAR DEGENERATION IN A PATIENT COMPRISING ADMINISTERING AN ANTI-C5A ANTIBODY

(71) Applicant: ALEXION PHARMACEUTICALS, INC., New Haven, CT (US)

(72) Inventors: Yi Wang, Woodbridge, CT (US); Barbel Rohrer, Charleston, SC (US)

(73) Assignee: ALEXION PHARMACEUTICALS, INC., Boston, MA (US)

( * ) Notice: Subject to any disclaimer, the term of this patent is extended or adjusted under 35 U.S.C. 154(b) by 228 days.

(21) Appl. No.: 15/766,753

(22) PCT Filed: Oct. 6, 2016

(86) PCT No.: PCT/US2016/055794
§ 371 (c)(1),
(2) Date: Apr. 6, 2018

(87) PCT Pub. No.: WO2017/062649
PCT Pub. Date: Apr. 13, 2017

(65) Prior Publication Data
US 2019/0218278 A1    Jul. 18, 2019

Related U.S. Application Data

(60) Provisional application No. 62/238,483, filed on Oct. 7, 2015.

(51) Int. Cl.
| | | |
|---|---|---|
| *C07K 16/18* | (2006.01) | |
| *A61K 39/395* | (2006.01) | |
| *A61P 27/02* | (2006.01) | |
| *A61K 9/00* | (2006.01) | |
| *A61K 39/00* | (2006.01) | |

(52) U.S. Cl.
CPC ............ *C07K 16/18* (2013.01); *A61K 9/0019* (2013.01); *A61P 27/02* (2018.01); *A61K 2039/505* (2013.01); *A61K 2039/54* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 4,676,980 A | 6/1987 | Segal et al. | |
| 5,258,498 A | 11/1993 | Huston et al. | |
| 5,525,491 A | 6/1996 | Huston et al. | |
| 5,534,254 A | 7/1996 | Huston et al. | |
| 6,005,079 A | 12/1999 | Casterman et al. | |
| 6,355,245 B1 | 3/2002 | Evans et al. | |
| 6,897,290 B1 | 5/2005 | Atkinson et al. | |
| 7,112,324 B1 | 9/2006 | Dorken et al. | |
| 7,390,786 B2 | 6/2008 | Warne et al. | |
| 7,999,081 B2 | 8/2011 | Tedesco et al. | |
| 8,241,628 B2 | 8/2012 | Diefenbach-Streiber et al. | |
| 8,454,963 B2 | 6/2013 | Tomlinson et al. | |
| 8,883,158 B2 | 11/2014 | Diefenbach-Streiber et al. | |
| 9,079,949 B1 | 7/2015 | Andrien, Jr. et al. | |
| 9,296,816 B2 | 3/2016 | Johnson et al. | |
| 2005/0265995 A1 | 12/2005 | Tomlinson et al. | |
| 2007/0004909 A1 | 1/2007 | Johnson et al. | |
| 2010/0034809 A1 | 2/2010 | Diefenbach-Streiber et al. | |
| 2012/0230982 A1 | 9/2012 | Xiao-Hong et al. | |
| 2012/0237515 A1 | 9/2012 | Bell et al. | |
| 2015/0299305 A1* | 10/2015 | Andrien, Jr. ............ A61P 27/02 435/69.6 |

FOREIGN PATENT DOCUMENTS

| | | |
|---|---|---|
| WO | 9404678 A1 | 3/1994 |
| WO | 9425591 A1 | 11/1994 |
| WO | 9627011 A1 | 9/1996 |
| WO | 2007024715 A2 | 3/2007 |
| WO | 2008024188 A2 | 2/2008 |
| WO | 2011/137395 A1 | 11/2011 |
| WO | 2011137395 A1 | 11/2011 |
| WO | 2012044893 A1 | 4/2012 |
| WO | 2012135345 A1 | 10/2012 |

OTHER PUBLICATIONS

Rudikoff et al., Proc Natl Acad Sci USA 79: 1979-1983 (1982). (Year: 1982).*
Colman, Research in Immunology 145: 33-36 (1994). 1994 (Year: 1994).*
Kussie et al.,J. Immunol. 152: 146-152 (1994). (Year: 1994).*
Chen et al., EMBO J., 14:2784-2794 (1995). (Year: 1994).*
D'Angelo et al., Many Routes to an Antibody Heavy-Chain CDR3: Necessary, Yet Insufficient, for Specific Binding; Frontiers in Immunology vol. 9, Article 395 Mar. 2018; doi:10.3389/fimmu.2018.00395. (Year: 2018).*
Piche-Nicholas et al., Changes in complemetarity-determining regions significantly alter IgG binding to the neonatal Fc receptor (FcRN) and pharmacokinetics; MABS 2018, vol. 10, No. 1, 81-94, doi.org/10.1080/19420862.2017.1389355). (Year: 2018).*
Liu et al., Journal of Translational Medicine 2011, 9: 111; www.translational-medicine.com/content/9/1/111). (Year: 2011).*
Thomas, TC et al. Inhibition of complement activity by humanized anti-C5 antibody and single-chain Fv. Mol Immunol. 1996;33(17-18):1389-401.

(Continued)

*Primary Examiner* — Phillip Gambel
(74) *Attorney, Agent, or Firm* — McBee Moore & Vanik IP, LLC

(57) ABSTRACT

The present disclosure relates to, inter alia, a method of treating age-related macular degeneration (AMD) in a patient, comprising administering an effective amount of a C5 inhibitor or a C5a inhibitor.

17 Claims, 14 Drawing Sheets
Specification includes a Sequence Listing.

(56) References Cited

OTHER PUBLICATIONS

Thurman JM et al. Oxidative stress renders retinal pigment epithelial cells susceptible to complement-mediated injury. J Biol Chem. 2009;284(25): 16939-47.
Todorovska et al., Design and application of diabodies, triabodies and tetrabodies for cancer targeting. J Immunol Methods. 2001;248(1-2):47-66.
Tutt, A et al. Trispecific F(ab')3 derivatives that use cooperative signaling via the TCR/CD3 complex and CD2 to activate and redirect resting cytotoxic T cells. J Immunol. 1991;147(1):60-69.
Van Kuik-Romeijn P et al. Expression of a functional mouse-human chimeric anti-CD19 antibody in the milk of transgenic mice. Transgenic Res. 2000;9(2):155-9.
Wang Y et al. Anti-C5 monoclonal antibody therapy prevents collagen-induced arthritis and ameliorates established disease. Proc Natl Acad Sci U S A. 1995;92:8955-8959.
Wang Y et al. Amelioration of lupus-like autoimmune disease in NZB/WF1 mice after treatment with a blocking monoclonal antibody specific for complement component C5. Proc Natl Acad Sci U S A. 1996;93:8563-8568.
Wang H et al. Complement inhibition with an anti-C5 monoclonal antibody prevents hyperacute rejection in a xenograft heart transplantation model. Transplantation. 1999;68(11):1643-51.
Ward, PA et al. Complement-derived leukotactic factors in inflammatory synovial fluids of humans. J Clin Invest. 1971;50(3):606-16.
Weisman, HF et al. Soluble human complement receptor type 1: In vivo inhibitor of complement suppressing post-ischemic myocardial inflammation and necrosis. Science. 1990;249(4965):146-51.
Wetsel; Kolb, Complement-independent activation of the fifth component (C5) of human complement: limited trypsin digestion resulting in the expression of biological activity. J Immunol. 1982;128(5):2209-2216.
Whiss, PA. Pexelizumab Alexion. Curr Opin Investig Drugs. 2002;3(6):870-7.
Wu C et al. Simultaneous targeting of multiple disease mediators by a dual-variable-domain immunoglobulin. Nat Biotechnol. 2007;25(11):1290-7.
Wuerzner, R. et al. Inhibition of terminal complement complex formation and cell lysis by monoclonal antibodies. Complement Inflamm. 1991;8(5-6):328-40.
Yamamoto KI et al. The complex of C5b and C6: isolation, characterization, and identification of a modified form of C5b consisting of three polypeptide chains. J Immunol. 1978;120(6):2008-2015.
Zapata, G et al. Engineering linear F(ab')2 fragments for efficient production in *Escherichia coli* and enhanced antiproliferative activity. Protein Eng. 1995;8(10):1057-62.
Zhu, Z. et al. High level secretion of a humanized bispecific diabody from *Escherichia coli*. Biotechnology (N Y). 1996;14(2):192-6.
Zuber, J et al. Use of eculizumab for atypical haemolytic uraemic syndrome and C3 glomerulopathies. Nat Rev Nephrol. 2012;8(11):643-57. doi: 10.1038/nmeph.2012.214. Epub Oct. 2, 2012.
Bruesselbach S et al., Enzyme recruitment and tumor cell killing in vitro by a secreted bispecific single-chain diabody. Tumor targeting. 1999;4:115-123.
Amsterdam, EA et al. Limitation of reperfusion injury by a monoclonal antibody to C5a during myocardial infarction in pigs. Am J Physiol. 1995;268(1 Pt 2):H448-57.
ALEXION. New Clinical Trial Data Show Substantial Improvement With Eculizumab (Soliris@) In Patients With Stec-Hus. Nov. 3, 2012. (Press Release).
Alzayady KJ et al. Functional inositol 1,4,5-trisphosphate receptors assembled from concatenated homo- and heteromeric subunits. J Biol Chem. 2013;288(41):29772-84.
Berge SM et al. Pharmaceutical salts. J Pharm Sci. 1977;66(1)1-19.
Brennan, M et al. Preparation of bispecific antibodies by chemical recombination of monoclonal immunoglobulin G1 fragments. Science. 1985;229(4708):81-3.

Damerau et al. Non-enzymic activation of the fifth component of human complement, by oxygen radicals. Some properties of the activation product, C5b-like C5. J Molecular Immunology. 1989;26:1133-1142.
Dunkelberger JR et al. Complement and its role in innate and adaptive immune responses. Cell Res. 2010;20(1):34-50.
Fredslund et al., Structure of and influence of a tick complement inhibitor on human complement component 5. Nat Immunol. 2008;9(7):753-60. doi: 10.1038/ni.1625. Epub Jun. 8, 2008.
Giani A et al. In vivo evaluation of laser-induced choroidal neovascularization using spectral-domain optical coherence tomography. Invest Ophthalmol Vis Sci. 2011;52(6):3880-7.
Grosse-Hovest, L et al. Cloned transgenic farm animals produce a bispecific antibody for T cell-mediated tumor cell killing. Proc Natl Acad Sci U S A. 2004;101(18):6858-63.
Gruber, M et al. Efficient tumor cell lysis mediated by a bispecific single chain antibody expressed in *Escherichia coli*. J Immunol. 1994;152(11):5368-5374.
Haq E et al. S-nitrosoglutathione prevents interphotoreceptor retinoid-binding protein (IRBP(161-180))-induced experimental autoimmune uveitis. J Ocul Pharmacol Ther. 2007;23(3):221-31.
Haviland et al., Complete cDNA sequence of human complement pro-C5. Evidence of truncated transcripts derived from a single copy gene. J Immunol. 1991;146 (1):362-368.
Hayden, MS et al. Single-chain mono- and bispecific antibody derivatives with novel biological properties and antitumour activity from a COS cell transient expression system. Ther Immunol. 1994;1(1):3-15.
Helfrich W et al. Construction and characterization of a bispecific diabody for retargeting T cells to human carcinomas. Int J Cancer. 1998;76(2):232-9.
Hillmen, P et al. Effect of eculizumab on hemolysis and transfusion requirements in patients with paroxysmal nocturnal hemoglobinuria. N Engl J Med. 2004;350(6):552-9.
Hillmen, P et al. The complement inhibitor eculizumab in paroxysmal nocturnal hemoglobinuria. N Engl J Med. 2006;355(12):1233-43.
Hoenemann, D et al. A novel recombinant bispecific single-chain antibody, bscWue-1×CD3, induces T-cell-mediated cytotoxicity towards human multiple myeloma cells. Leukemia. 2004;18(3):636-44.
Holers VM et al. The spectrum of complement alternative pathway-mediated diseases. Immunol Rev. 2008;223:300-316.
Holliger, P et al. "Diabodies": small bivalent and bispecific antibody fragments. Proc Natl Acad Sci USA. 1993;90(14):6444-6448.
Homeister, JW et al. Soluble complement receptor type 1 prevents human complement-mediated damage of the rabbit isolated heart. J Immunol. 1993;150(3):1055-64.
Houdebine LM. Antibody manufacture in transgenic animals and comparisons with other systems. Curr Opin Biotechnol. 2002;13(6):625-9.
Hudson et al. High avidity scFv multimers; diabodies and triabodies. J Immunol Methods. 1999;231(1-2):177-89.
Johne B et al. Epitope mapping and binding kinetics of monoclonal antibodies studied by real time biospecific interaction analysis using surface plasmon resonance. J Immunol Methods. 1993;160(2):191-8.
Keefe, AD et al. Aptamers as therapeutics. Nat Rev Drug Discov. 2010;9(7):537-50.
Kipriyanov SM et al. Bispecific tandem diabody for tumor therapy with improved antigen binding and pharmacokinetics. J Mol Biol. 1999;293(1):41-56.
Korn, T et al. Recombinant bispecific antibodies for the targeting of adenoviruses to CEA-expressing tumour cells: a comparative analysis of bacterially expressed single-chain diabody and tandem scFv. J Gene Med. Jun. 2004;6(6):642-51.
Kostelny, SA et al. Formation of a bispecific antibody by the use of leucine zippers. J Immunol. 1992;148(5):1547-53.
Kroshus, TJ et al. Complement inhibition with an anti-C5 monoclonal antibody prevents acute cardiac tissue injury in an ex vivo model of pig-to-human xenotransplantation. Transplantation. 1995;60(11):1194-1202.

(56) References Cited

OTHER PUBLICATIONS

Maletz, K et al. Bispecific single-chain antibodies as effective tools for eliminating epithelial cancer cells from human stem cell preparations by redirected cell cytotoxicity. Int J Cancer. 2001;93(3):409-16.

Minta et al. Cleavage of human C5 by trypsin: characterization of the digestion products by gel electrophoresis. J Immunol. 1977;119(5);1597-1602.

Moongkarndi, P et al. Immunological and functional properties of two monoclonal antibodies against human C5. Immunobiol. 1983;165:323.

Moongkarndi, P et al. Monoclonal antibodies against the fifth component of human complement. Immunobiol. 1982;162:397.

Muyldermans et al., Recognition of antigens by single-domain antibody fragments: the superfluous luxury of paired domains. Trends Biochem Sci. 2001;26(4):230-5.

Nettelbeck DM et al. Targeting of Adenovirus to Endothelial Cells by a Bispecific Single-Chain Diabody Directed against the Adenovirus Fiber Knob Domain and Human Endoglin (CD105). Mol Ther. 2001;3(6):882-91.

Noris, M. et al. STEC-HUS, atypical HUS and TTP are all diseases of complement activation. Nat Rev Nephrol. 2012;8(11):622-33. doi: 10.1038/nrneph.2012.195. Epub Sep. 18, 2012.

Nuttall SD et al., Immunoglobulin VH domains and beyond: design and selection of single-domain binding and targeting reagents. Curr Pharm Biotechnol. 2000;1(3):253-63.

Patel, MR et al. Pexelizumab: A novel therapy for myocardial ischemia-reperfusion. Drugs Today (Barc). 2005;41(3):165-70.

Poljak RJ, Production and structure of diabodies. Structure. 1994;2(12):1121-1123.

Pollock DP et al. Transgenic milk as a method for the production of recombinant antibodies. J Immunol Methods. 1999;231(1-2):147-57.

Rabinovici, R et al. Role of complement in endotoxin/platelet-activating factor-induced lung injury. J Immunol. 1992;149(5):1744-50.

Ren-Heidenreich, L et al. Redirected T-cell cytotoxicity to epithelial cell adhesion molecule-overexpressing adenocarcinomas by a novel recombinant antibody, E3Bi, in vitro and in an animal model. Cancer. 2004;100(5):1095-103.

Rinder CS et al. Blockade of C5a and C5b-9 generation inhibits leukocyte and platelet activation during extracorporeal circulation. J Clin Invest. 1995;96:1564-1572.

Rohrer B et al. A targeted inhibitor of the alternative complement pathway reduces angiogenesis in a mouse model of age-related macular degeneration. Invest Ophthalmol Vis Sci. 2009;50(7):3056-64.

Romay-Penabad, Z et al. Complement C5-inhibitor rEV576 (coversin) ameliorates in-vivo effects of antiphospholipid antibodies. Lupus. 2014;23(12):1324-6.

Rondon IJ et al. Intracellular antibodies (intrabodies) for gene therapy of infectious diseases. Annu Rev Microbiol. 1997;51:257-83.

Rother et al. Discovery and development of the complement inhibitor eculizumab for the treatment of paroxysmal nocturnal hemoglobinuria. Nature Biotechnology. 2007;25:1256-1264.

Segal, DM et al. Production of bispecific antibodies. Curr Protoc Immunol. 1995; Chap. 2.13.1-2.13.16.

Shalaby, MR et al. Development of humanized bispecific antibodies reactive with cytotoxic lymphocytes and tumor cells overexpressing the HER2 protooncogene. J Exp Med. 1992;175(1):217-25.

Song, H et al. Complement receptor 2-mediated targeting of complement inhibitors to sites of complement activation. J Clin Invest. 2003;111(12):1875-85.

Suresh, MR et al. Bispecific monoclonal antibodies from hybrid hybridomas. Methods Enzymol. 1986;121:210-28.

Miho Nozaki et al., "Drusen complement components C3a and C5a promote choroidal neovascularization," Proceedings of the National Academy of Sciences of the United States of America, (2006), vol. 103, No. 7: 2328-2333.

Christopher Toomey et al., "Effect of Anti-C5a Therapy in a Murine Model of Early/Intermediate Fry Age-Related Macular Degeneration," Investigative Opthalmology & Visual Science, (2018), vol. 59, No. 2: 662-673.

Buschini, Elisa, et al., "Recent developments in the management of dry age-related macular degeneration," Clinical Ophthalmology, (2015), vol. 9 : 563-574.

ALEXION, Annual Report, (2010).

International Search Report received in PCT/US16/55974 dated Dec. 31, 2017; pp. 6.

Michael John Tolentino et al: Drugs in Phase I I clinical trials for the treatment of age-related macular degeneration11 , Expert Opinion on Investigational Drugs, vol. 24. No. 2. Sep. 22, 2014 (Sep. 22, 2014), pp. 183-199, XP055263180,UK; ISSN: 1354-3784, DOI:10.1517/13543784.2015.961601 p. 191.

Zohar Yehoshua et al: "Systemic Complement Inhibition with Eculizumab for Geographic Atrophy in Age-Related Macular Degeneration". Ophthalmology., vol. 121, No. 3, Mar. 1, 2014 (Mar. 1, 2014), pp. 693-701, XP55331111, US ISSN: 0161-6420, DOI: 10.1016/j.ophtha.2013.09.044 abstract.

Joensson U el al. Introducing a biosensor based technology for real-time biospecific interaction analysis. Ann Biol Clin (Paris). 1993;51(1):19-26.

Joensson U et al. Real-time biospecific interaction analysis using surface plasmon resonance and a sensor chip technology. Biotechniques. 1991;11(5):620-7.

Reichmann et al., Single domain antibodies: comparison of camel VH and camelised human VH domains. J Immunol Methods. 1999;231(1-2):25-38.

Wurzner, R. et al. Inhibition of terminal complement complex formation and cell lysis by monoclonal antibodies. Complement Inflamm. 1991;8(5-6):328-40.

Zuber, J et al. Use of eculizumab for atypical haemolytic uraemic syndrome and C3 glomerulopathies. Nat Rev Nephrol. 2012;8(11):643-57. doi: 10.1038/nrneph.2012.214. Epub Oct. 2, 2012.

\* cited by examiner

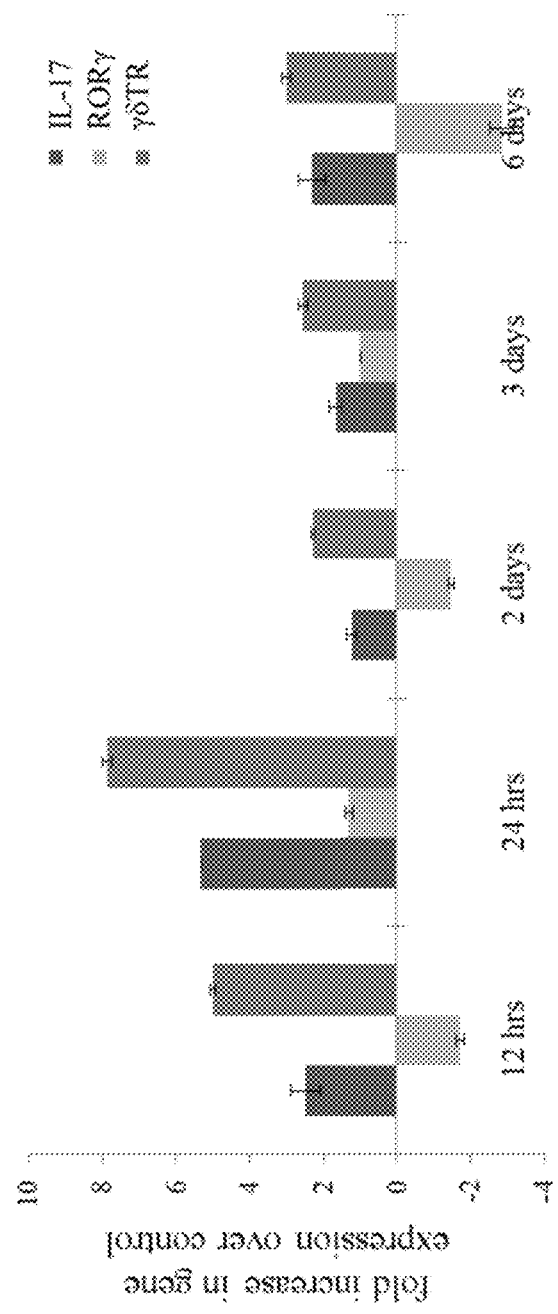
Figure 1: T cell gene expression in the eye over time in response to CNV lesions

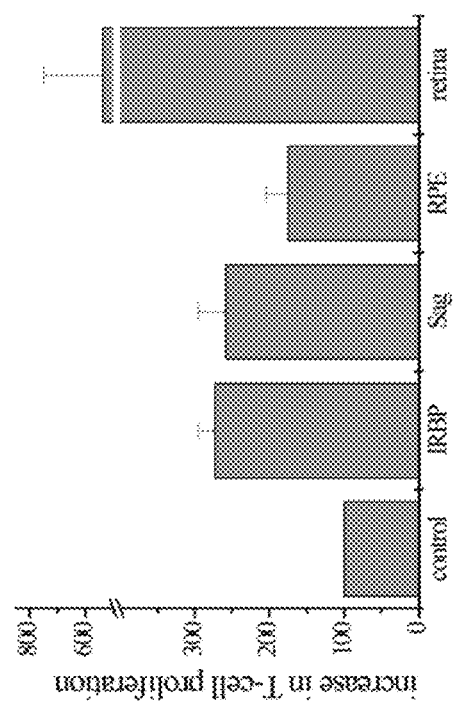
Figure 2: T-cell proliferation in response to ocular antigens

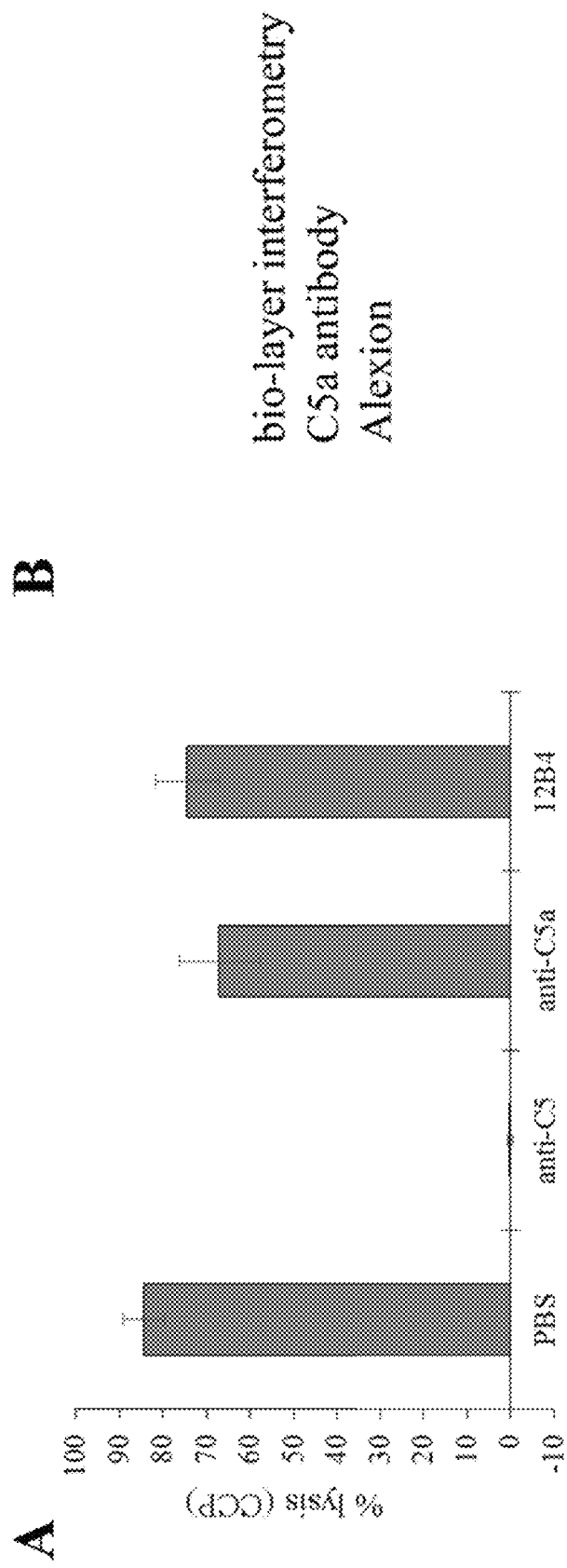

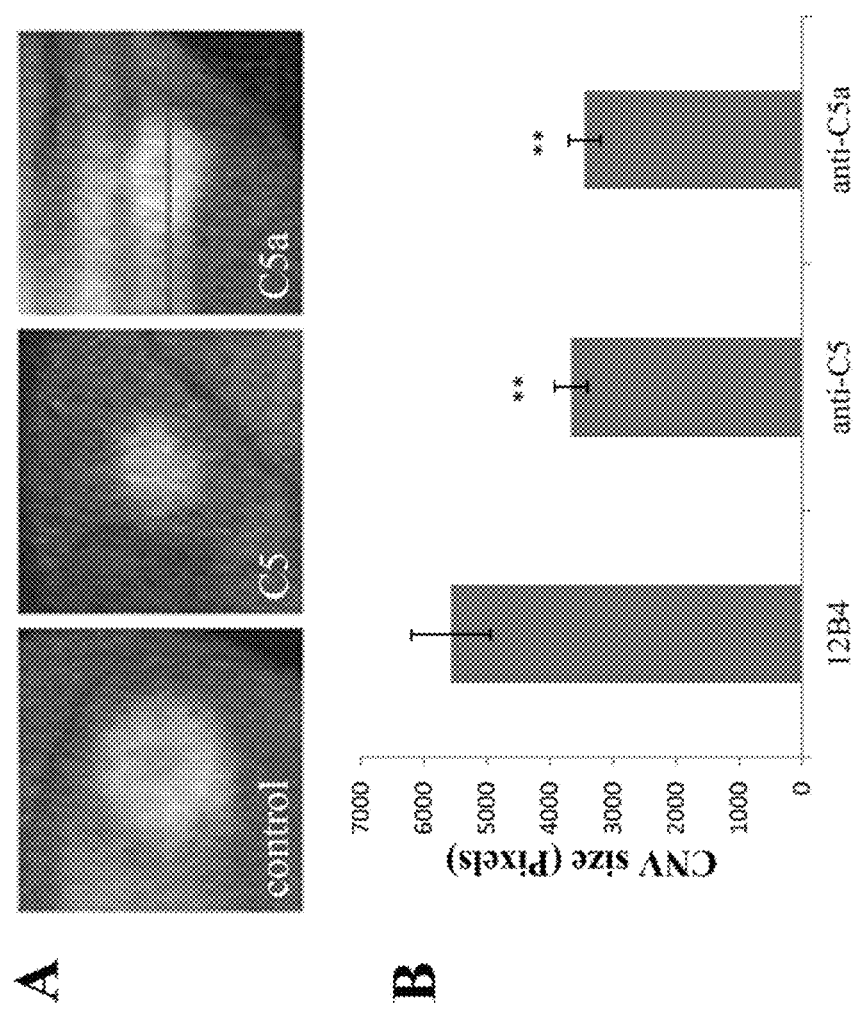
Figure 4: CNV is reduced in animals injected with anti-C5 and anti-C5a blocking antibodies

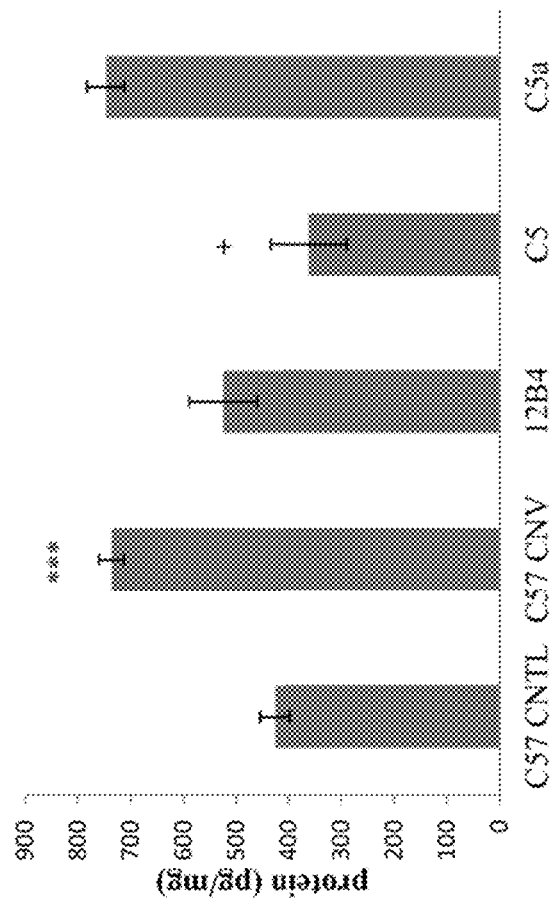
Figure 5: Animals injected with anti-C5 have lower ocular C5a levels.

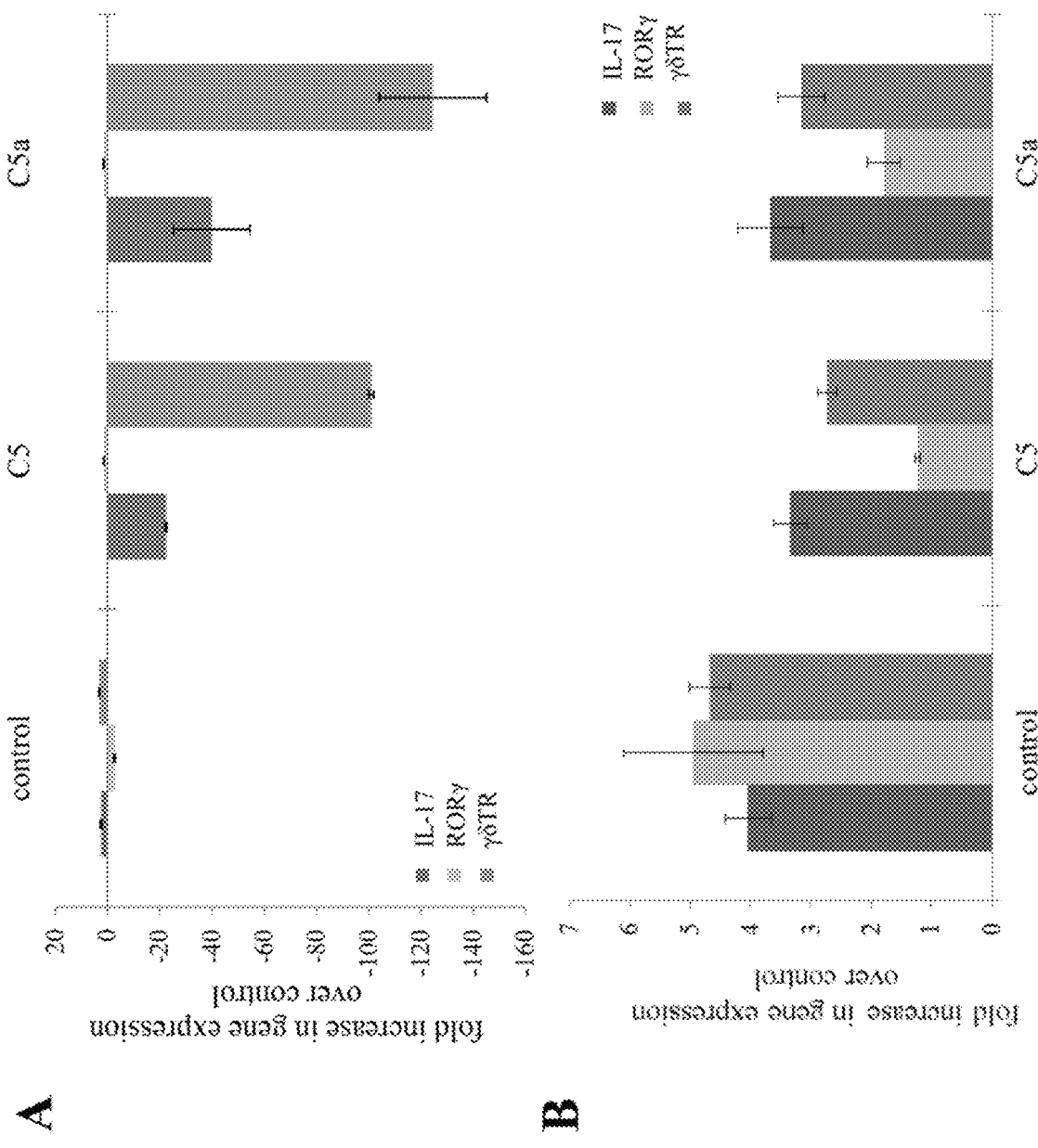
Figure 6: effects of C5a and C5 on ocular (a) and (b) splenic T-cells

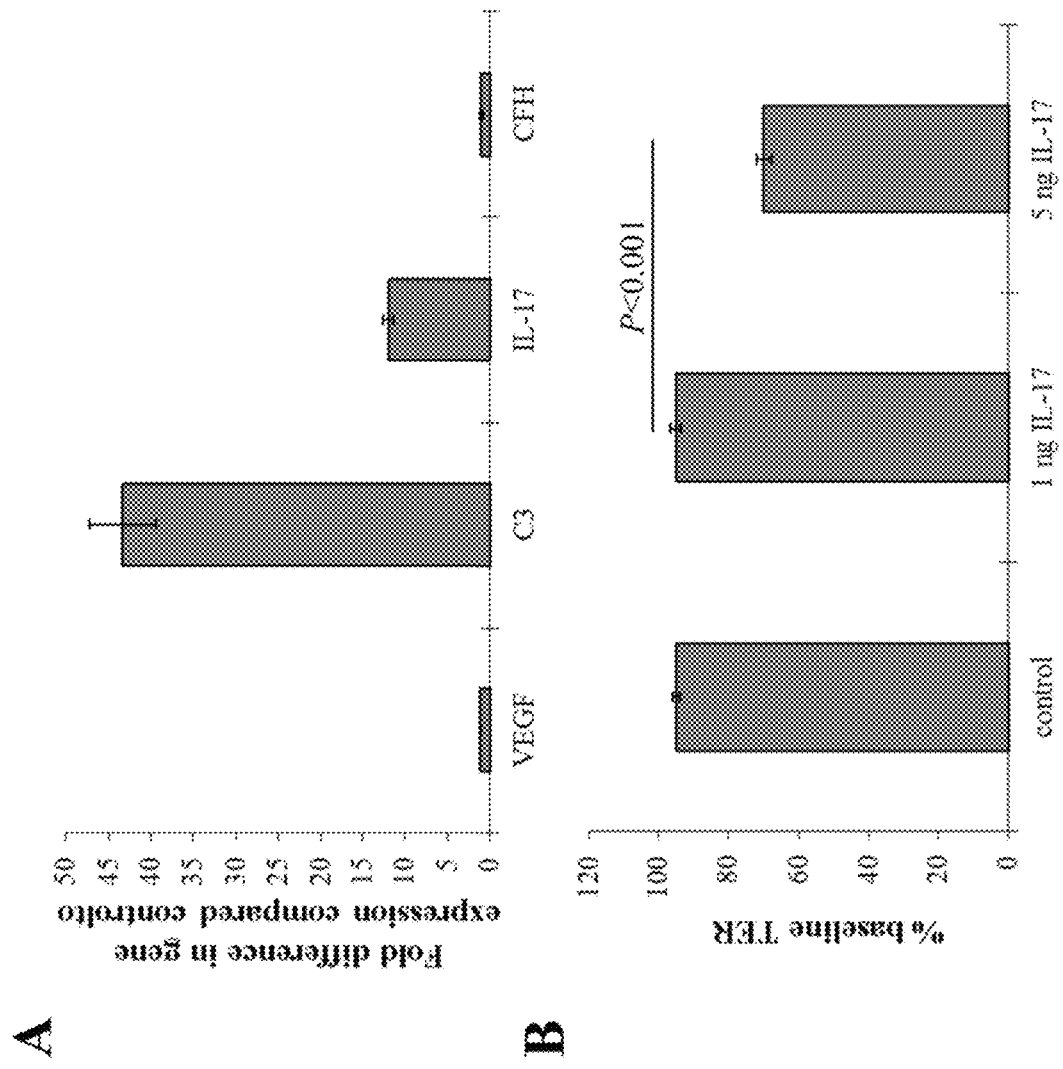
Figure 7: ARPE-19 cells treated with IL-17 have change in (a) gene expression and (b) barrier function 22 Days After IVT or IV 22 Days After IVT or IV

SEQUENCE LISTING

<160> NUMBER OF SEQ ID NOS: 50

<210> SEQ ID NO 1
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(738)

<400> SEQUENCE: 1

```
gat atc cag atg acc cag tcc ccg tcc tcc ctg tcc gcc tct gtg ggc      48
Asp Ile Gln Met Thr Gln Ser Pro Ser Ser Leu Ser Ala Ser Val Gly
 1               5                  10                  15 gat agg gtc acc atc acc tgc ggc gcc agc gaa aac atc tat ggc gcg      96
Asp Arg Val Thr Ile Thr Cys Gly Ala Ser Glu Asn Ile Tyr Gly Ala
                20                  25                  30 ctg aac tgg tat caa cag aaa ccc ggg aaa gct ccg aag ctt ctg att     144
Leu Asn Trp Tyr Gln Gln Lys Pro Gly Lys Ala Pro Lys Leu Leu Ile
            35                  40                  45 tac ggt gcg acg aac ctg gca gat gga gtc cct tct cgc ttc tct gga     192
Tyr Gly Ala Thr Asn Leu Ala Asp Gly Val Pro Ser Arg Phe Ser Gly
        50                  55                  60 tcc ggc tcc gga acg gat ttc act ctg acc atc agc agt ctg cag cct     240
Ser Gly Ser Gly Thr Asp Phe Thr Leu Thr Ile Ser Ser Leu Gln Pro
 65                  70                  75                  80 gaa gac ttc gct acg tat tac tgt cag aac gtt tta aat act ccg ttg     288
Glu Asp Phe Ala Thr Tyr Tyr Cys Gln Asn Val Leu Asn Thr Pro Leu
                 85                  90                  95 act ttc gga cag ggt acc aag gtg gaa ata aaa cgt act ggc ggt ggt     336
Thr Phe Gly Gln Gly Thr Lys Val Glu Ile Lys Arg Thr Gly Gly Gly
                100                 105                 110 ggt tct ggt ggc ggt gga tct ggt ggt ggc ggt tct caa gtc caa ctg     384
Gly Ser Gly Gly Gly Gly Ser Gly Gly Gly Gly Ser Gln Val Gln Leu
            115                 120                 125 gtg caa tcc ggc gcc gag gtc aag aag cca ggg gcc tca gtc aaa gtg     432
Val Gln Ser Gly Ala Glu Val Lys Lys Pro Gly Ala Ser Val Lys Val
        130                 135                 140 tcc tgt aaa gct agc ggc tat att ttt tct aat tat tgg att caa tgg     480
Ser Cys Lys Ala Ser Gly Tyr Ile Phe Ser Asn Tyr Trp Ile Gln Trp
145                 150                 155                 160 gtg cgt cag gcc ccc ggg cag ggc ctg gaa tgg atg ggt gag atc tta     528
Val Arg Gln Ala Pro Gly Gln Gly Leu Glu Trp Met Gly Glu Ile Leu
                165                 170                 175
```

```
ccg ggc tct ggt agc acc gaa tat acc gaa aat ttt aaa gac cgt gtt    576
Pro Gly Ser Gly Ser Thr Glu Tyr Thr Glu Asn Phe Lys Asp Arg Val
            180                 185                 190 act atg acg cgt gac act tcg act agt aca gta tac atg gag ctc tcc    624
Thr Met Thr Arg Asp Thr Ser Thr Ser Thr Val Tyr Met Glu Leu Ser
        195                 200                 205 agc ctg cga tcg gag gac acg gcc gtc tat tat tgc gcg cgt tat ttt    672
Ser Leu Arg Ser Glu Asp Thr Ala Val Tyr Tyr Cys Ala Arg Tyr Phe
    210                 215                 220 ttt ggt tct agc ccg aat tgg tat ttt gat gtt tgg ggt caa gga acc    720
Phe Gly Ser Ser Pro Asn Trp Tyr Phe Asp Val Trp Gly Gln Gly Thr
225                 230                 235                 240 ctg gtc act gtc tcg agc tga                                        741
Leu Val Thr Val Ser Ser
                245
```

<210> SEQ ID NO 2
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Gly Ser Gln Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Ile Phe Ser Asn Tyr Trp Ile Gln Trp
145                 150                 155                 160

Val Arg Gln Ala Pro Gly Gln Gly Leu Glu Trp Met Gly Glu Ile Leu
                165                 170                 175

Pro Gly Ser Gly Ser Thr Glu Tyr Thr Glu Asn Phe Lys Asp Arg Val
            180                 185                 190

Thr Met Thr Arg Asp Thr Ser Thr Ser Thr Val Tyr Met Glu Leu Ser
        195                 200                 205

Ser Leu Arg Ser Glu Asp Thr Ala Val Tyr Tyr Cys Ala Arg Tyr Phe
    210                 215                 220

Phe Gly Ser Ser Pro Asn Trp Tyr Phe Asp Val Trp Gly Gln Gly Thr
225                 230                 235                 240

Leu Val Thr Val Ser Ser
                245
```

<210> SEQ ID NO 3
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 1676
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 4

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

-continued

```
Glu Asp Leu Lys Asp Asp Gln Lys Glu Met Met Gln Thr Ala Met Gln
            275                 280                 285
Asn Thr Met Leu Ile Asn Gly Ile Ala Gln Val Thr Phe Asp Ser Glu
290                 295                 300
Thr Ala Val Lys Glu Leu Ser Tyr Tyr Ser Leu Glu Asp Leu Asn Asn
305                 310                 315                 320
Lys Tyr Leu Tyr Ile Ala Val Thr Val Ile Glu Ser Thr Gly Gly Phe
                325                 330                 335
Ser Glu Glu Ala Glu Ile Pro Gly Ile Lys Tyr Val Leu Ser Pro Tyr
                340                 345                 350
Lys Leu Asn Leu Val Ala Thr Pro Leu Phe Leu Lys Pro Gly Ile Pro
                355                 360                 365
Tyr Pro Ile Lys Val Gln Val Lys Asp Ser Leu Asp Gln Leu Val Gly
370                 375                 380
Gly Val Pro Val Ile Leu Asn Ala Gln Thr Ile Asp Val Asn Gln Glu
385                 390                 395                 400
Thr Ser Asp Leu Asp Pro Ser Lys Ser Val Thr Arg Val Asp Asp Gly
                405                 410                 415
Val Ala Ser Phe Val Leu Asn Leu Pro Ser Gly Val Thr Val Leu Glu
                420                 425                 430
Phe Asn Val Lys Thr Asp Ala Pro Asp Leu Pro Glu Glu Asn Gln Ala
                435                 440                 445
Arg Glu Gly Tyr Arg Ala Ile Ala Tyr Ser Ser Leu Ser Gln Ser Tyr
                450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
                485                 490                 495
Thr His Tyr Asn Tyr Leu Ile Leu Ser Lys Gly Lys Ile Ile His Phe
                500                 505                 510
Gly Thr Arg Glu Lys Phe Ser Asp Ala Ser Tyr Gln Ser Ile Asn Ile
                515                 520                 525
Pro Val Thr Gln Asn Met Val Pro Ser Ser Arg Leu Leu Val Tyr Tyr
                530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
                565                 570                 575
Pro Asp Ala Asp Ala Tyr Ser Pro Gly Gln Thr Val Ser Leu Asn Met
                580                 585                 590
Ala Thr Gly Met Asp Ser Trp Val Ala Leu Ala Ala Val Asp Ser Ala
                595                 600                 605
Val Tyr Gly Val Gln Arg Gly Ala Lys Lys Pro Leu Glu Arg Val Phe
610                 615                 620
Gln Phe Leu Glu Lys Ser Asp Leu Gly Cys Gly Ala Gly Gly Gly Leu
625                 630                 635                 640
Asn Asn Ala Asn Val Phe His Leu Ala Gly Leu Thr Phe Leu Thr Asn
                645                 650                 655
Ala Asn Ala Asp Asp Ser Gln Glu Asn Asp Glu Pro Cys Lys Glu Ile
                660                 665                 670
Leu Arg Pro Arg Arg Thr Leu Gln Lys Lys Ile Glu Glu Ile Ala Ala
                675                 680                 685
Lys Tyr Lys His Ser Val Val Lys Lys Cys Cys Tyr Asp Gly Ala Cys
```

```
            690                 695                 700
Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
                740                 745                 750

His Met Lys Thr Leu Leu Pro Val Ser Lys Pro Glu Ile Arg Ser Tyr
                755                 760                 765

Phe Pro Glu Ser Trp Leu Trp Glu Val His Leu Val Pro Arg Arg Lys
            770                 775                 780

Gln Leu Gln Phe Ala Leu Pro Asp Ser Leu Thr Thr Trp Glu Ile Gln
785                 790                 795                 800

Gly Ile Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
                820                 825                 830

Val Val Arg Gly Glu Gln Ile Gln Leu Lys Gly Thr Val Tyr Asn Tyr
                835                 840                 845

Arg Thr Ser Gly Met Gln Phe Cys Val Lys Met Ser Ala Val Glu Gly
            850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
                900                 905                 910

Ser Leu Glu Thr Trp Phe Gly Lys Glu Ile Leu Val Lys Thr Leu Arg
            915                 920                 925

Val Val Pro Glu Gly Val Lys Arg Glu Ser Tyr Ser Gly Val Thr Leu
            930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
                980                 985                 990

Ser Gln Glu Gly Ile Asn Ile Leu Thr His Leu Pro Lys Gly Ser Ala
                995                 1000                1005

Glu Ala Glu Leu Met Ser Val Val Pro Val Phe Tyr Val Phe His
    1010                1015                1020

Tyr Leu Glu Thr Gly Asn His Trp Asn Ile Phe His Ser Asp Pro
    1025                1030                1035

Leu Ile Glu Lys Gln Lys Leu Lys Lys Lys Leu Lys Glu Gly Met
    1040                1045                1050

Leu Ser Ile Met Ser Tyr Arg Asn Ala Asp Tyr Ser Tyr Ser Val
    1055                1060                1065

Trp Lys Gly Gly Ser Ala Ser Thr Trp Leu Thr Ala Phe Ala Leu
    1070                1075                1080

Arg Val Leu Gly Gln Val Asn Lys Tyr Val Glu Gln Asn Gln Asn
    1085                1090                1095

Ser Ile Cys Asn Ser Leu Leu Trp Leu Val Glu Asn Tyr Gln Leu
    1100                1105                1110
```

```
Asp Asn Gly Ser Phe Lys Glu Asn Ser Gln Tyr Gln Pro Ile Lys
1115                1120                1125

Leu Gln Gly Thr Leu Pro Val Glu Ala Arg Glu Asn Ser Leu Tyr
1130                1135                1140

Leu Thr Ala Phe Thr Val Ile Gly Ile Arg Lys Ala Phe Asp Ile
1145                1150                1155

Cys Pro Leu Val Lys Ile Asp Thr Ala Leu Ile Lys Ala Asp Asn
1160                1165                1170

Phe Leu Leu Glu Asn Thr Leu Pro Ala Gln Ser Thr Phe Thr Leu
1175                1180                1185

Ala Ile Ser Ala Tyr Ala Leu Ser Leu Gly Asp Lys Thr His Pro
1190                1195                1200

Gln Phe Arg Ser Ile Val Ser Ala Leu Lys Arg Glu Ala Leu Val
1205                1210                1215

Lys Gly Asn Pro Pro Ile Tyr Arg Phe Trp Lys Asp Asn Leu Gln
1220                1225                1230

His Lys Asp Ser Ser Val Pro Asn Thr Gly Thr Ala Arg Met Val
1235                1240                1245

Glu Thr Thr Ala Tyr Ala Leu Leu Thr Ser Leu Asn Leu Lys Asp
1250                1255                1260

Ile Asn Tyr Val Asn Pro Val Ile Lys Trp Leu Ser Glu Glu Gln
1265                1270                1275

Arg Tyr Gly Gly Gly Phe Tyr Ser Thr Gln Asp Thr Ile Asn Ala
1280                1285                1290

Ile Glu Gly Leu Thr Glu Tyr Ser Leu Leu Val Lys Gln Leu Arg
1295                1300                1305

Leu Ser Met Asp Ile Asp Val Ser Tyr Lys His Lys Gly Ala Leu
1310                1315                1320

His Asn Tyr Lys Met Thr Asp Lys Asn Phe Leu Gly Arg Pro Val
1325                1330                1335

Glu Val Leu Leu Asn Asp Asp Leu Ile Val Ser Thr Gly Phe Gly
1340                1345                1350

Ser Gly Leu Ala Thr Val His Val Thr Thr Val Val His Lys Thr
1355                1360                1365

Ser Thr Ser Glu Glu Val Cys Ser Phe Tyr Leu Lys Ile Asp Thr
1370                1375                1380

Gln Asp Ile Glu Ala Ser His Tyr Arg Gly Tyr Gly Asn Ser Asp
1385                1390                1395

Tyr Lys Arg Ile Val Ala Cys Ala Ser Tyr Lys Pro Ser Arg Glu
1400                1405                1410

Glu Ser Ser Ser Gly Ser Ser His Ala Val Met Asp Ile Ser Leu
1415                1420                1425

Pro Thr Gly Ile Ser Ala Asn Glu Glu Asp Leu Lys Ala Leu Val
1430                1435                1440

Glu Gly Val Asp Gln Leu Phe Thr Asp Tyr Gln Ile Lys Asp Gly
1445                1450                1455

His Val Ile Leu Gln Leu Asn Ser Ile Pro Ser Ser Asp Phe Leu
1460                1465                1470

Cys Val Arg Phe Arg Ile Phe Glu Leu Phe Glu Val Gly Phe Leu
1475                1480                1485

Ser Pro Ala Thr Phe Thr Val Tyr Glu Tyr His Arg Pro Asp Lys
1490                1495                1500
```

Gln Cys Thr Met Phe Tyr Ser Thr Ser Asn Ile Lys Ile Gln Lys
    1505                1510                1515

Val Cys Glu Gly Ala Ala Cys Lys Cys Val Glu Ala Asp Cys Gly
    1520                1525                1530

Gln Met Gln Glu Glu Leu Asp Leu Thr Ile Ser Ala Glu Thr Arg
    1535                1540                1545

Lys Gln Thr Ala Cys Lys Pro Glu Ile Ala Tyr Ala Tyr Lys Val
    1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 5
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly Ser Thr Glu Tyr Thr Glu Asn Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro

```
            165                 170                 175
Ala Val Leu Gln Ser Ser Gly Leu Tyr Ser Leu Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
            210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 6
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Leu His Glu Ala
            420                 425                 430
Leu His Ser His Tyr Thr Gln Lys Ser Leu Ser Leu Ser Leu Gly Lys
        435                 440                 445

<210> SEQ ID NO 8
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Thr Gln Ser Pro Ser Ser Leu Ser Ala Ser Val Gly
1               5                   10                  15
Asp Arg Val Thr Ile Thr Cys Gly Ala Ser Glu Asn Ile Tyr Gly Ala
            20                  25                  30
Leu Asn Trp Tyr Gln Gln Lys Pro Gly Lys Ala Pro Lys Leu Leu Ile
        35                  40                  45
Tyr Gly Ala Thr Asn Leu Ala Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Asn Val Leu Asn Thr Pro Leu
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly

```
            115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Tyr Ile Phe Ser Asn Tyr Trp Ile Gln
1               5                   10

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Glu Ile Leu Pro Gly Ser Gly Ser Thr Glu Tyr Thr Glu Asn Phe Lys
1               5                   10                  15
Asp

<210> SEQ ID NO 11
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Tyr Phe Phe Gly Ser Ser Pro Asn Trp Tyr Phe Asp Val
1               5                   10

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12
```

```
Gly Ala Ser Glu Asn Ile Tyr Gly Ala Leu Asn
1               5                   10
```

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

```
Gly Ala Thr Asn Leu Ala Asp
1               5
```

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

```
Gln Asn Val Leu Asn Thr Pro Leu Thr
1               5
```

<210> SEQ ID NO 15
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser
            115                 120
```

<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Gly Gly Gly Ser Gly Gly Gly Gly Ser
1               5                   10

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Gly Gly Ser Gly Gly Gly Ser Gly Gly Gly Ser Gly Gly Gly Ser
1               5                   10                  15

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20
```

Gly Gly Gly Ser
1

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Gly Gly Gly Gly
1               5

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Gly Gly Gly Gly Ser Gly Gly Gly Gly
1               5                   10

<210> SEQ ID NO 23
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
aaatctggca ccacaccttc                                              20

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
ggggtgttga aggtctcaaa                                              20

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
tcagataagg aggggcacaa                                              20

<210> SEQ ID NO 26
<211> LENGTH: 22

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
atgaagaggt acccactctg ga                                           22

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
cagggtactt tgcctgctga                                              20

<210> SEQ ID NO 28
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
tggattttca tggtggggca                                              20

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ctggaccctg gctttactgc                                              20

<210> SEQ ID NO 30
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tgaacttgat cacttcatgg gact                                         24

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
```

```
ttcagggtcg agaagatgct                                               20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
aaacgtgggg gtttcttagg                                               20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
cgactggagg accttctacg                                               20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ttggcaaact ccaccacata                                               20

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
caggcactta catccactgg t                                             21

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
tgaatctgga atccaccaca g                                             21

<210> SEQ ID NO 37
<211> LENGTH: 20
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic primer"

<400> SEQUENCE: 37
aaatctggca ccacaccttc                                                  20

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
ggggtgttga aggtctcaaa                                                  20

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
accacaccct ccaaacaaag                                                  20

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
actgtcttct ccacggtgct                                                  20

<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
tcttcaagcc atcctgtgtc                                                  20

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
atccgcataa tctgcatggt                                                  20

<210> SEQ ID NO 43
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
gcaatgagga ccctgagaga                                                      20

<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
tggatgggga cagagttcat                                                      20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
agaaggcacc caggctatct                                                      20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
cacagggcct tttctgacat                                                      20

<210> SEQ ID NO 47
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
```

```
                65                  70                  75                  80
        Ser Leu Gln Pro Glu Asp Phe Ala Thr Tyr Tyr Cys Gln Gln Ser Asn
                            85                  90                  95

Glu Asp Pro Tyr Thr Phe Gly Gly Gly Thr Lys Val Glu Ile Lys Arg
                        100                 105                 110

Thr Val Ala Ala Pro Ser Val Phe Ile Phe Pro Pro Ser Asp Glu Gln
                        115                 120                 125

Leu Lys Ser Gly Thr Ala Ser Val Val Cys Leu Leu Asn Asn Phe Tyr
                    130                 135                 140

Pro Arg Glu Ala Lys Val Gln Trp Lys Val Asp Asn Ala Leu Gln Ser
        145                 150                 155                 160

Gly Asn Ser Gln Glu Ser Val Thr Glu Gln Asp Ser Lys Asp Ser Thr
                            165                 170                 175

Tyr Ser Leu Ser Ser Thr Leu Thr Leu Ser Lys Ala Asp Tyr Glu Lys
                        180                 185                 190

His Lys Val Tyr Ala Cys Glu Val Thr His Gln Gly Leu Ser Ser Pro
                        195                 200                 205

Val Thr Lys Ser Phe Asn Arg Gly Glu Cys
                    210                 215

<210> SEQ ID NO 48
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Val Gln Leu Val Gln Ser Gly Ala Glu Val Lys Lys Pro Gly Ala
        1               5                   10                  15

Ser Val Lys Val Ser Cys Lys Ala Ser Gly Tyr Thr Phe Thr Asp Tyr
                        20                  25                  30

Ser Met Asp Trp Val Arg Gln Ala Pro Gly Gln Gly Leu Glu Trp Met
                    35                  40                  45

Gly Ala Ile His Leu Asn Thr Gly Tyr Thr Asn Tyr Asn Gln Lys Phe
                50                  55                  60

Lys Gly Arg Val Thr Met Thr Arg Asp Thr Ser Thr Ser Thr Val Tyr
        65                  70                  75                  80

Met Glu Leu Ser Ser Leu Arg Ser Glu Asp Thr Ala Val Tyr Tyr Cys
                            85                  90                  95

Ala Arg Gly Phe Tyr Asp Gly Tyr Ser Pro Met Asp Tyr Trp Gly Gln
                        100                 105                 110

Gly Thr Thr Val Thr Val Ser Ser Ala Ser Thr Lys Gly Pro Ser Val
                    115                 120                 125

Phe Pro Leu Ala Pro Cys Ser Arg Ser Thr Ser Glu Ser Thr Ala Ala
                130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                            165                 170                 175

Leu Gln Ser Ser Gly Leu Tyr Ser Leu Ser Ser Val Val Thr Val Pro
                        180                 185                 190

Ser Ser Asn Phe Gly Thr Gln Thr Tyr Thr Cys Asn Val Asp His Lys
                    195                 200                 205
```

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
                385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
    420                 425                 430

Asn His Tyr Thr Gln Lys Ser Leu Ser Leu Gly Lys
        435                 440                 445

<210> SEQ ID NO 49
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met Asp Trp Val Arg Gln Ala Pro Gly Gln Gly Leu Glu Trp Met
            35                  40                  45

Gly Ala Ile His Leu Asn Thr Gly Tyr Thr Asn Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
            100                 105                 110

```
Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Val Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 50
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
```

```
                   20                  25                  30
Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Ser Gln Val Gln Leu
            115                 120                 125

Val Gln Ser Gly Ala Glu Val Lys Lys Pro Gly Ala Ser Val Lys Val
            130                 135                 140

Ser Cys Lys Ala Ser Gly Tyr Ile Phe Ser Asn Tyr Trp Ile Gln Trp
145                 150                 155                 160

Val Arg Gln Ala Pro Gly Gln Gly Leu Glu Trp Met Gly Glu Ile Leu
                165                 170                 175

Pro Gly Ser Gly Ser Thr Glu Tyr Thr Glu Asn Phe Lys Asp Arg Val
                180                 185                 190

Thr Met Thr Arg Asp Thr Ser Thr Ser Thr Val Tyr Met Glu Leu Ser
            195                 200                 205

Ser Leu Arg Ser Glu Asp Thr Ala Val Tyr Tyr Cys Ala Arg Tyr Phe
    210                 215                 220

Phe Gly Ser Ser Pro Asn Trp Tyr Phe Asp Val Trp Gly Gln Gly Thr
225                 230                 235                 240

Leu Val Thr Val Ser Ser
                245
```

METHODS OF TREATING AGE-RELATED MACULAR DEGENERATION IN A PATIENT COMPRISING ADMINISTERING AN ANTI-C5A ANTIBODY

INCORPORATION OF SEQUENCE LISTING

The instant application contains a Sequence Listing which has been submitted electronically in ASCII format and is hereby incorporated by reference in its entirety. Said ASCII copy, created on Sep. 30, 2016, is named 1900-417PCT_SL.txt and is 57,044 bytes in size.

TECHNICAL FIELD

This invention relates to the fields of immunology and immunological disorders.

BACKGROUND

In humans, age-related macular degeneration (AMD) is the leading cause of blindness in industrialized nations. The disease is most common in adults age 50 or older, with an estimated 1.75 million Americans currently diagnosed with advanced AMD. AMD gradually leads to the degeneration of the macula, the site of central, fine-tuned vision in the human eye. Advanced AMD occurs in two forms, dry (atrophic) and wet AMD.

Atrophic AMD is characterized by thinning or loss of the macular retinal pigment epithelium (RPE) and thickening of Bruch's membrane (BrM), leading to atrophic region (geographic atrophy, or GA) and affects the great majority of people afflicted with AMD. The appearance of increasing number of large drusen (crystalline deposits of extracellular material) and linear deposits (basolaminar deposits) between the RPE and BrM are indicative of dry AMD. These deposits interfere with the hydraulic conductivity of BrM and impair the integrity of the RPE, which ultimately affects the health of the photoreceptors, resulting in retinal degeneration.

Wet AMD is characterized by breakdown of RPE/Bruch's membrane, increased release of the pro-angiogenic factor VEGF, and development of choroidal neovascularization (CNV).

In CNV, newly formed choroidal blood vessels grow through the RPE/BrM. Since new blood vessels are leakier, fluid accumulates between the RPE and the retina, disrupting the connection between the photoreceptors and the RPE. Unless the fluid is drained and the retina allowed to reattach, the photoreceptors will be lost, leading to loss of vision.

New, effective treatment for AMD is needed.

SUMMARY

This disclosure solves the issue above by providing a method of treating AMD in a patient, comprising administering an effective amount of an inhibitor, the inhibitor being either (or both) a C5 inhibitor, such as, for example, an antibody, including eculizumab, or an antigen-binding fragment thereof, or an eculizumab variant, or an antigen-binding fragment thereof, or an a C5a inhibitor, such as an anti-C5a antibody, or an antigen-binding fragment thereof, to the patient.

Numerous other aspects are provided in accordance with these and other aspects of the invention. Other features and aspects of the present invention will become more fully apparent from the following detailed description and the appended claims.

BRIEF DESCRIPTION OF THE DRAWINGS

FIG. 1 shows T cell gene expression in the eye over time. Expression of IL-17, RORγ, and γδTR (γδT cell receptor) following CNV were measured at 12 hours, 24 hours, 2 days, 3 days, and 6 days. Levels of IL-17 mRNA peaked at 24 hours following CNV and remained elevated throughout 6 days. γδTR levels were similarly elevated through day 6 with a peak observed at 24 hours. RORγ levels remained unaltered in the presence of CNV. Data shown are average values (±SEM) per sample.

FIG. 2 shows T cell proliferation in response to ocular antigens. T cells derived from spleens of CNV animals were stimulated by various ocular antigens and T cell proliferation was measured. Splenocytes stimulated by the RPE/choroid (RPE) extracts and the retina proteins IRBP and S-antigen demonstrated a moderate increase (2-3 fold) in proliferation when compared to control; whereas stimulation with retinal extracts resulted in a much larger (6-fold) increase in T cell proliferation. Data shown are average values (±SD) per sample.

FIG. 3 shows characterization of antibodies. (a) Serum from mice injected with PBS, anti-C5, anti-C5a, and the antibody control 12B4 were analyzed for complement activation through use of a hemolysis assay. Serum from anti-C5 antibody treated animals was unable to lyse sheep red blood cells, indicating successful blockage of complement activation. No significant difference was reported between lysis in mice injected with anti-C5a, PBS or 12B4. Data shown are average values (±SEM) per sample. (b) Specificity of the monoclonal antibody specific for murine C5a was confirmed to bind to its target, murine C5a, with single digit nM affinity, using bio-layer interferometry.

FIG. 4 shows CNV is reduced in animals injected with anti-C5 and anti-C5a. Following laser-induced CNV, OCT was used to measure lesion size in the presence of anti-C5, anti-C5a, or 12B4 (control). OCT images show a decrease in lesion size with treatment of anti-C5 and anti-C5a when compared to control (a). Quantification of these results (b) indicated a nearly 40% decrease in lesion size when injected with anti-C5 and anti-C5a (P≤0.01). Data shown are average values (±SEM) per lesion.

FIG. 5 shows that animals injected with anti-C5 have lower ocular anti-C5a levels. ELISA measurements of RPE/choroid demonstrated an increase of C5a levels after induction of CNV (P≤0.001). This increase was eliminated in anti-C5-treated mice; whereas mice treated with anti-C5a and 12B4 control antibodies had control levels of ocular C5a. Data shown are average values (±SEM).

FIG. 6 shows effects of C5a and C5 on T cells. Splenic (b) and ocular (a) samples were isolated 6 days after induction of CNV and analyzed by QRT-PCR using primers specific for Th-17 (RORγ) and γδT-cells (γδTR). (a) Following CNV, mice treated with anti-C5 and anti-C5a demonstrated a significant decrease in ocular levels of IL-17 and γδTR gene expression, whereas RORγ levels were unaltered. (b). Splenic levels of T-cell-specific genes in CNV mice indicated that RORγ levels returned to control levels in mice treated with anti-C5 and anti-C5a, whereas γδTR remained elevated.

FIG. 7 shows effect of IL-17 on RPE cells. (a) Change in gene expression following apical IL-17 exposure (5 ng/mL) was measured in mature ARPE-19 cell monolayers. C3 as well as IL-17 expression levels demonstrated an increase in fold change over the control, whereas VEGF and CFH were unaltered. (b) Transepithelial resistance measurements indicated a loss in barrier function in response to apical application of 5 ng/mL IL-17 after four hours.

DETAILED DESCRIPTION

Figure 8B:
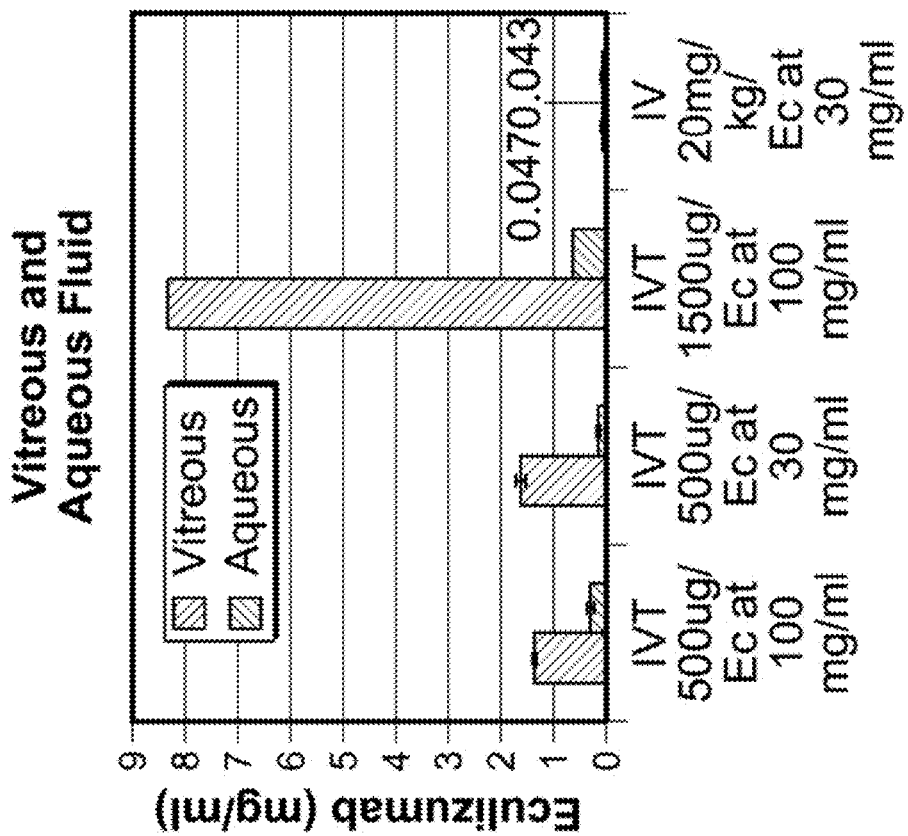
FIG. 8 shows that intravitreal (IVT) administration resulted in higher eculizumab (Ec) concentrations in retina and vitreous, aqueous than for IV dosing of 20 mg/Kg of eculizumab.

As used herein, the word "a" or "plurality" before a noun represents one or more of the particular noun. For example, the phrase "a mammalian cell" represents "one or more mammalian cells."

The term "antibody" is known in the art. The term "antibody" is sometimes used interchangeably with the term "immunoglobulin." Briefly, it can refer to a whole antibody comprising two light chain polypeptides and two heavy chain polypeptides. Whole antibodies include different antibody isotypes including IgM, IgG, IgA, IgD, and IgE antibodies. The term "antibody" includes, for example, a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody. The antibody can also be an engineered protein or antibody-like protein containing at least one immunoglobulin domain (e.g., a fusion protein). The engineered protein or antibody-like protein can also be a bi-specific antibody or a tri-specific antibody, or a dimer, trimer, or multimer antibody, or a diabody, a DVD-Ig, a CODV-Ig, an AFFIBODY®, or a NANOBODY®. The term antibody also includes antibody fragments.

The term "antibody fragment," "antigen-binding fragment," or similar terms are known in the art and can, for example, refer to a fragment of an antibody that retains the ability to bind to a target antigen (e.g., human C5 or human C5a) and inhibit the activity of the target antigen. Such antibody fragments include, e.g., a single chain antibody, a single chain Fv fragment (scFv), an Fd fragment, an Fab fragment, an Fab' fragment, or an F(ab')2 fragment. A scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283. An antigen-binding fragment can also include the variable region of a heavy chain polypeptide and the variable region of a light chain polypeptide. An antigen-binding fragment can thus comprise the CDRs of the light chain and heavy chain polypeptide of an antibody.

The term "antibody fragment" also can include, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079. The term "antibody fragment" also includes single domain antibodies comprising two $V_H$ domains with modifications such that single domain antibodies are formed.

An "antibody fragment" also includes a polypeptide comprising the antigen binding parts (one or more of the CDRs) of an antibody.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

All publications, patent applications, patents, sequences, database entries, and other references mentioned herein are incorporated by reference in their entirety. In case of conflict, the present specification, including definitions, will control.

The Complement System

The immune system is divided into two distinct types—innate and adaptive. The innate immune system consists of the complement system as well as different immune cell types that include phagocytes, mast cells, eosinophils, and basophils. The adaptive immune system, in which pathogenic exposure confers long-term defense memory in the host organism, includes T- and B-lymphocytes. While both systems primarily protect the organism against invading pathogens, under disease conditions, self-cells can become targets for destruction and invading immune cell can cause damage to the host they are intended to protect. Finally, a number of different links exist that connect the innate and adaptive immune responses, including the complement system, and involving cell types that have functional characteristics of both systems, which includes B1-cells and γδT-cells.

The complement system is initiated through three separate and independent pathways, the classical, the lectin, and the alternative pathway. These three pathways converge at the formation of a C3 convertase, C4bC2a (classical and lectin pathway C3 convertase) and C3bBb (alternative pathway C3 convertase), which then triggers activation of the common terminal pathway. As part of the terminal pathway, C3 and C5 convertase activation results in the production of the soluble anaphylatoxins C3a and C5a, which play a major role in mediating chemotaxis, inflammation, and the generation of cytotoxic oxygen radicals.

The C5 convertases cleave C5, which is a 190 kDa beta globulin found in normal human serum at approximately 75 μg/ml (0.4 μM). C5 is glycosylated, with about 1.5-3 percent of its mass attributed to carbohydrate. Mature C5 is a heterodimer of a 999 amino acid 115 kDa alpha chain that is disulfide linked to a 655 amino acid 75 kDa beta chain. C5 is synthesized as a single chain precursor protein product of a single copy gene (Haviland et al. (1991) *J Immunol.* 146:362-368). The cDNA sequence of the transcript of this human gene predicts a secreted pro-C5 precursor of 1658 amino acids along with an 18 amino acid leader sequence. See, e.g., U.S. Pat. No. 6,355,245.

The pro-C5 precursor is cleaved after amino acids 655 and 659, to yield the beta chain as an amino terminal fragment (amino acid residues +1 to 655 of the above sequence) and the alpha chain as a carboxyl terminal fragment (amino acid residues 660 to 1658 of the above sequence), with four amino acids (amino acid residues 656-659 of the above sequence) deleted between the two.

C5a is cleaved from the alpha chain of C5 by either alternative or classical C5 convertase as an amino terminal fragment comprising the first 74 amino acids of the alpha chain (i.e., amino acid residues 660-733 of the above sequence). Approximately 20 percent of the 11 kDa mass of C5a is attributed to carbohydrate. The cleavage site for convertase action is at, or immediately adjacent to, amino acid residue 733. A compound that would bind at, or adjacent to, this cleavage site would have the potential to block access of the C5 convertase enzymes to the cleavage site and thereby act as a complement inhibitor. A compound that binds to C5 at a site distal to the cleavage site could also have the potential to block C5 cleavage, for example, by way of steric hindrance-mediated inhibition of the interaction between C5 and the C5 convertase. A compound, in a mechanism of action consistent with that of the tick saliva complement inhibitor, *Ornithodoros moubata* C inhibitor (OmCI) (which can be a C5 inhibitor), may also prevent C5 cleavage by reducing flexibility of the C345C domain of the alpha chain of C5, which reduces access of the C5 convertase to the cleavage site of C5. See, e.g., Fredslund et al. (2008) *Nat Immunol* 9(7):753-760.

C5 can also be activated by means other than C5 convertase activity. Limited trypsin digestion (see, e.g., Minta and Man (1997) *J Immunol* 119:1597-1602 and Wetsel and Kolb (1982) *J Immunol* 128:2209-2216) and acid treatment (Yamamoto and Gewurz (1978) *J Immunol* 120:2008 and Damerau et al. (1989) *Molec Immunol* 26:1133-1142) can also cleave C5 and produce active C5b.

Cleavage of C5 releases C5a, a potent anaphylatoxin and chemotactic factor, and leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

The first step in the formation of the terminal complement complex involves the combination of C5b with C6, C7, and C8 to form the C5b-8 complex at the surface of the target cell. Upon the binding of the C5b-8 complex with several C9 molecules, the membrane attack complex ("MAC", C5b-9, terminal complement complex—"TCC") is formed. When sufficient numbers of MACs insert into target cell membranes the openings they create (MAC pores) mediate rapid osmotic lysis of the target cells, such as red blood cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

While a properly functioning complement system provides a robust defense against infecting microbes, inappropriate regulation or activation of complement has been implicated in the pathogenesis of a variety of disorders, including, e.g., rheumatoid arthritis ("RA"); lupus nephritis; asthma; ischemia-reperfusion injury; atypical hemolytic uremic syndrome ("aHUS"); dense deposit disease ("DDD"); paroxysmal nocturnal hemoglobinuria ("PNH"); macular degeneration (e.g., age-related macular degeneration ("AMD")); hemolysis, elevated liver enzymes, and low platelets ("HELLP") syndrome; thrombotic thrombocytopenic purpura ("TTP"); spontaneous fetal loss; Pauci-immune vasculitis; epidermolysis bullosa; recurrent fetal loss; multiple sclerosis ("MS"); traumatic brain injury; and injury resulting from myocardial infarction, cardiopulmonary bypass and hemodialysis. See, e.g., Holers et al. (2008) *Immunological Reviews* 223:300-316. Inhibition of complement (e.g., inhibition of terminal complement formation, C5 cleavage, or complement activation) has been demonstrated to be effective in treating several complement-associated disorders both in animal models and in humans. See, e.g., Rother et al. (2007) *Nature Biotechnology* 25(11):1256-1264; Wang et al. (1996) *Proc Natl Acad Sci USA* 93:8563-8568; Wang et al. (1995) *Proc Natl Acad Sci USA* 92:8955-8959; Rinder et al. (1995) *J Clin Invest* 96:1564-1572; Kroshus et al. (1995) *Transplantation* 60:1194-1202; Homeister et al. (1993) *J Immunol* 150:1055-1064; Weisman et al. (1990) *Science* 249:146-151; Amsterdam et al. (1995) *Am J Physiol* 268:H448-H457; and Rabinovici et al. (1992) *J Immunol* 149:1744 1750.

C3a and C5a are anaphylatoxins. These activated complement components can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

Anaphylatoxin receptors are G-protein coupled cell surface receptors expressed by many different cells. They have been demonstrated to be present on retinal pigment epithelium (RPE) and choroidal endothelial cells based on functional assays and receptor-mediated movement of leukocytes in the direction of the increasing concentration of anaphylatoxins has been demonstrated.

Leukocytes fall into two categories, myeloid cells (neutrophils, monocytes, eosinophils and basophils) and lymphocytes (T-cells, B-cells and natural killer cells). In animal models of AMD a number of cells have been identified to infiltrate the eyes, including neutrophils and macrophages, natural killer cells and T-cells; likewise, T-cells, macrophages and monocytes as well as other immune cells have been identified in eyes from AMD patients. T-cells consist of four categories, T-helper cells (which includes Th1-, Th2- and Th17-cells), cytotoxic T-cells, γδT-cells, and T-regulatory cells. Importantly, the signature cytokine of Th17- and γδT-cells, IL-17, is significantly increased human eyes with AMD8, and blocking IL-17 in eyes of mice with focal retinal degeneration was found to be neuroprotective. Therefore, it was postulated that one or both of these cell types, Th17- and γδT-cells, contribute to inflammation and angiogenesis in the eye through the production of the IL-17 cytokine.

Treating AMD

In humans, age-related macular degeneration (AMD) is the leading cause of blindness in industrialized nations. The disease is most common in adults age 50 or older, with an estimated 1.75 million Americans currently diagnosed with advanced AMD. AMD gradually leads to the degeneration of the macula, the site of central, fine-tuned vision in the human eye. Advanced AMD occurs in two forms, dry (atrophic) and wet AMD.

Atrophic AMD is characterized by thinning or loss of the macular retinal pigment epithelium (RPE) and thickening of Bruch's membrane (BrM), leading to atrophic region (geographic atrophy, or GA) and affects the great majority of people afflicted with AMD. The appearance of increasing number of large drusen (crystalline deposits of extracellular material) and linear deposits (basolaminar deposits) between the RPE and BrM are indicative of dry AMD. These deposits interfere with the hydraulic conductivity of BrM and impair the integrity of the RPE, which ultimately affects the health of the photoreceptors, resulting in retinal degeneration.

Wet AMD is characterized by breakdown of RPE/Bruch's membrane, increased release of the pro-angiogenic factor VEGF and development of choroidal neovascularization (CNV).

In CNV, newly formed choroidal blood vessels grow through the RPE/BrM. Since new blood vessels are leakier, fluid will accumulate between the RPE and the retina, disrupting the connection between the photoreceptors and the RPE. Unless the fluid is drained and the retina allowed to reattach, the photoreceptors will be lost, leading to loss of vision.

In certain aspects, a method of treating age-related macular degeneration (AMD) in a patient is provided. In certain embodiments, the patient is a human patient. The method comprises administering an effective amount of an inhibitor, either a C5 inhibitor or a C5a inhibitor, or both, to the patient.

In certain embodiments, the inhibitor is a C5 inhibitor. In certain further embodiments, the C5 inhibitor is a polypeptide or an antibody. Eculizumab or an eculizumab variant is an example of an anti-C5 antibody. In certain embodiments, the eculizumab or eculizumab variant is administered at about 30 mg/ml to about 100 mg/ml (including about 30 mg/ml and about 100 mg/ml), or more, to the patient. In certain embodiments, the anti-C5 antibody is a single-chain antibody. In certain embodiments, the anti-C5 antibody is a polypeptide comprising one of the amino acid sequence depicted in SEQ ID NO:1, SEQ ID NO:2, SEQ ID NO:5 and SEQ ID NO:6, or SEQ ID NO: 7 and SEQ ID NO: 8, or SEQ ID NO:50, or an antigen binding fragment of any of the above. In certain other embodiments, the anti-C5 antibody is a polypeptide comprising one or more of the amino acid sequence depicted in SEQ ID NOs:9-16.

In certain embodiments, the inhibitor is a C5a inhibitor. In further embodiments, the C5a inhibitor is an antibody.

One example of an anti-C5a antibody is CLS026. CLS026 is a monoclonal antibody specific for murine C5a. CLS026 was derived from a phage display library using conventional panning techniques, with negative selection against human C5 and converted to a full length IgG. This neoepitope specific antibody binds to its target, murine C5a, with single digit nM affinity, as shown with bio-layer interferometry. CLS026 was cultured in CHO cells and purified using single step affinity chromatography with mabselect Xtra (GE) protein A resin. CLS026 was free of endotoxin and determined to be greater than 95% pure using capillary electrophoresis. See also the anti-C5a antibodies from Biocompare, South San Francisco, Calif.

Yet another example is an anti-human C5a antibody, with a light chain depicted in SEQ ID NO:47 and a heavy chain depicted in SEQ ID NO:48 or SEQ ID NO: 49.

The amount of C5a in a patient before, during, and after treatment can be monitored, by, for example, an immunoassay, such as an ELISA.

For example, for the quantitative determination of mouse C5a in RPE/choroid tissue homogenates, a sandwich enzyme immunoassay is used according to the manufacturer's instructions (Kamiya Biomedical Company; Seattle, Wash.). In short, pre-coated plates are exposed to the antigen for 2 hours at 37° C., washed and incubated with detection antibody to C5a followed by peroxidase-conjugated secondary antibody and color development using TMB substrate. The concentration of C5a in the ocular samples are determined by comparing the O.D. of the samples to a calibration curve (calibrators provided in the kit).

In certain embodiments, the inhibitor is administered intravenously or intravitreally, or both.

In certain embodiments, the inhibitor is administered at about 500 µg to about 1,500 µg per eye. In yet other embodiments, wherein the inhibitor is administered at about 0.5 mg, about 1.5 mg, about 5 mg, or about 10 mg per eye. In further embodiments, the inhibitor is administered at about 0.5 mg to about 10 mg per eye.

In certain embodiments, the level of γδT-cells in the eye is reduced. In certain embodiments, the levels of Th17- and/or γδT-cells in the spleen are reduced. In some embodiments, the level of IL-17 in the eye is reduced. In certain embodiments, the inflammation in the eye is reduced. In some embodiments, choroidal neovascularization (CNV) in the eye is reduced.

Any method for identifying and quantifying γδT-cells, Th17- and/or γδT-cells, and IL-17 can be used. Such methods are known in the art.

In certain embodiments, the AMD is wet AMD or is dry (atrophic) AMD. Diagnosis of AMD is known in the art.

In certain embodiments, a typical therapeutic treatment includes a series of doses, which will usually be administered concurrently with the monitoring of clinical endpoints with the dosage levels adjusted as needed to achieve the desired clinical outcome. In certain embodiments, a typical therapeutic treatment includes one or more dosages administered within about 12-48 hours after diagnosis of AMD, possibly with follow-up dosages after that time period. In certain embodiments, treatment is administered in multiple dosages over at least a few hours or a few days. In certain embodiments, treatment is administered in multiple dosages over at least a week. In certain embodiments, treatment is administered in multiple dosages over at least a month. In certain embodiments, treatment is administered in multiple dosages over at least a year. In certain embodiments, treatment is administered in multiple dosages over the remainder of the patient's life.

The frequency of administration can also be adjusted according to various parameters. These include, for example, the clinical response, the plasma half-life of the inhibitor, and the levels of the inhibitor (such as an antibody) in a body fluid, such as, blood, plasma, serum, or synovial fluid. To guide adjustment of the frequency of administration, levels of the inhibitor in the body fluid can be monitored during the course of treatment.

In certain embodiments, the dosage(s) and frequency of administration are determined according to the need of the patient, at the discretion of the treating physician.

For the treatment of AMD by systemic administration of an inhibitor, administration of a large initial dose can be performed. Such a large initial dose can be followed by regularly repeated administration of tapered doses as needed. In other embodiments, the initial dose is given by both local and systemic routes, followed by repeated systemic administration of tapered doses.

In some embodiments, the complement C5 protein is a human complement C5 protein (the human proprotein is depicted in SEQ ID NO:4). In some embodiments, the complement C5a protein is a human complement C5a protein.

In certain embodiments, a therapeutically effective amount of an inhibitor (such as eculizumab) can include an amount (or various amounts in the case of multiple administrations) that improves or maintains the patient's vision.

In certain embodiments, the method further comprises administering a second therapeutic agent to the patient. Any appropriate second therapeutic agent is contemplated.

Anti-C5 Inhibitor and Anti-C5a Inhibitor

A C5 inhibitor can be any C5 inhibitor. In certain embodiments, the C5 inhibitor is eculizumab, an antigen-binding fragment thereof, a polypeptide comprising the antigen-binding fragment of eculizumab, a fusion protein comprising the antigen binding fragment of eculizumab, or a single chain antibody version of eculizumab, or a small-molecule C5 inhibitor.

In some embodiments, the C5 inhibitor is a small-molecule chemical compound. One example of a small molecule chemical compound that is a C5 inhibitor is Aurin tricarboxylic acid. In other embodiments, the C5 inhibitor is a polypeptide, such as an antibody.

The C5 inhibitor is one that binds to a complement C5 protein and is also capable of inhibiting the generation of C5a. A C5-binding inhibitor can also be capable of inhibiting, e.g., the cleavage of C5 to fragments C5a and C5b, and thus preventing the formation of terminal complement complex.

For example, an anti-C5 antibody blocks the generation or activity of the C5a active fragment of a C5 protein (e.g., a human C5 protein). Through this blocking effect, the antibody inhibits, e.g., the proinflammatory effects of C5a. An anti-C5 antibody can further have activity in blocking the generation or activity of C5b. Through this blocking effect, the antibody can further inhibit, e.g., the generation of the C5b-9 membrane attack complex at the surface of a cell.

In some embodiments, the C5 inhibitor antibody is a polypeptide inhibitor. In yet further other embodiments, the polypeptide inhibitor is eculizumab. SEQ ID NO:5 depicts the entire heavy chain of eculizumab; SEQ ID NO:6 depicts the entire light chain of eculizumab; SEQ ID NOs:9-11 depict, respectively, CDR1-3 of the heavy chain of eculizumab; SEQ ID NOs:12-14 depict, respectively, CDR1-3 of the light chain of eculizumab; SEQ ID NO:15 depicts the variable region of the heavy chain of eculizumab; and SEQ ID NO:16 depicts the variable region of the light chain of Eculizumab. Eculizumab is a humanized anti-human C5 monoclonal antibody (Alexion Pharmaceuticals, Inc.), with a human IgG2/IgG4 hybrid constant region, so as to reduce the potential to elicit proinflammatory responses. Eculizumab has the trade name SOLIRIS® and is currently approved for treating paroxysmal nocturnal hemoglobinuria ("PNH") and atypical hemolytic uremic syndrome ("aHUS"). Paroxysmal nocturnal hemoglobinuria is a form of hemolytic anemia, intravascular hemolysis being a prominent feature due to the absence of the complement regulatory protein CD59 and CD55. CD59, for example, functions to block the formation of the terminal complement complex. AHUS involves chronic uncontrolled complement activation, resulting in, inter alia, inhibition of thrombolitic microangiopathy, the formation of blood clots in small blood vessels throughout the body, and acute renal failure. Eculizumab specifically binds to human C5 protein and blocks the formation of the generation of the potent proinflammatory protein C5a. Eculizumab further blocks the formation of the terminal complement complex. Eculizumab treatment reduces intravascular hemolysis in patients with PNH and decreases complement levels in aHUS. See, e.g., Hillmen et al., *N Engl J Med* 2004; 350:552-9; Rother et al., *Nature Biotechnology* 2007; 25(11): 1256-1264; Hillmen et al., *N Engl J Med* 2006, 355; 12, 1233-1243; Zuber et al., *Nature Reviews Nephrology* 8, 643-657 (2012)|U.S. Patent Publication Number 2012/0237515, and U.S. Pat. No. 6,355,245. Eculizumab has also been shown in a recent clinical trial to be effective for patients with Shiga-toxin-producing *E. coli* hemolytic uremic syndrome ("STEC-HUS"). See Alexion press release, "New Clinical Trial Data Show Substantial Improvement with Eculizumab (SOLIRIS®) in Patients with STEC-HUS," Saturday, Nov. 3, 2012. STEC-HUS is characterized by systemic complement-mediated thrombotic microangiopathy and acute vital organ damage. Eculizumab administration to these patients resulted in rapid and sustained improvement in thrombotic microangiopathy and improvements in systemic organ complications. As can be seen, like PNH, aHUS, and STEC-HUS are all diseases relating to inappropriate complement activation. See, e.g., Noris et al., *Nat Rev Nephrol.* 2012 November; 8(11):622-33.; Hillmen et al., *N* Engl J Med 2004; 350:6, 552-9; Rother et al., *Nature Biotechnology* 2007; 25(11): 1256-1264; Hillmen et al., *N Engl J Med* 2006, 355; 12, 1233-1243; Zuber et al., *Nature Reviews Nephrology* 8, 643-657 (2012).

In yet further other embodiments, the C5 inhibitor is a single chain version of eculizumab, including pexelizumab (SEQ ID NO:1)—a specific single chain version of the whole antibody eculizumab. See, e.g., Whiss (2002) *Curr Opin Investig Drugs* 3(6):870-7; Patel et al. (2005) *Drugs Today (Barc)* 41(3):165-70; Thomas et al. (1996) *Mol Immunol* 33(17-18):1389-401; and U.S. Pat. No. 6,355,245. In yet other embodiments, the C5 inhibitor antibody is a single chain variant of pexelizumab, with the arginine (R) at position 38 (according to Kabat numbering and the amino acid sequence number set forth in SEQ ID NO:2) of the light chain of the pexelizumab antibody amino acid sequence changed to a glutamine (Q). The single chain antibody having the amino acid sequence depicted in SEQ ID NO:2 is a variant of the single chain antibody pexelizumab (SEQ ID NO:1), in which the arginine (R) at position 38 has been substituted with a glutamine (Q). An exemplary linker amino acid sequence present in a variant pexelizumab antibody is shown in SEQ ID NO:3. An exemplary ScFv of eculizumab is depicted in SEQ ID NO: 50.

In certain embodiments, the anti-C5 antibody is a variant derived from eculizumab, having one or more improved properties (e.g., improved pharmacokinetic properties) relative to eculizumab. The variant eculizumab antibody (also referred to herein as an eculizumab variant, a variant eculizumab, or the like) or C5-binding fragment thereof is one that: (a) binds to complement component C5; (b) inhibits the generation of C5a; and can further inhibit the cleavage of C5 into fragments C5a and C5b. The variant eculizumab antibody can have a serum half-life in a human that is greater than, or at least, 10 (e.g., greater than, or at least, 11, 12, 13, 14, 15, 16, 17, 18, 19, 20, 21, 22, 23, 24, 25, 26, 27, 28, 29, 30, 31, 32, 33 or 34) days. Such variant eculizumab antibodies are described in U.S. Pat. No. 9,079,949.

In certain embodiments, the eculizumab variant antibody is an antibody defined by the sequences depicted in SEQ ID NO:7 (heavy chain) and SEQ ID NO:8 (light chain), or an antigen-binding fragment thereof. This antibody binds to human C5 and inhibits the formation of C5a, as well as the cleavage of C5 to fragments C5a and C5b, and thus preventing the formation of terminal complement complex.

The C5-binding polypeptide antibody for use in methods of this invention can comprise, or can consist of, the amino acid sequence depicted in SEQ ID NO:1, SEQ ID NO:2, SEQ ID NO:5 and SEQ ID NO:6, or SEQ ID NO: 7 and SEQ ID NO: 8, or an antigen binding fragment of any of the above. The polypeptide can comprise one or more of the amino acid sequence depicted in SEQ ID NOs:9-16.

In yet other embodiments, the C5 inhibitor is LFG316 (Novartis, Basel, Switzerland, and MorphoSys, Planegg, Germany) or another antibody defined by the sequences of Table 1 in U58,241,628 and U58,883,158, ARC1905 (Ophthotech, Princeton, N.J. and New York, N.Y.), which is an anti-C5 pegylated RNA aptamer (see, e.g., Keefe et al., *Nature Reviews Drug Discovery* 9, 537-550 (July 2010), MUBODINA® (Adienne Pharma & Biotech, Bergamo, Italy) (see, e.g., U57,999,081), rEV576 (coversin) (Volution Immuno-pharmaceuticals, Geneva, Switzerland)(see, e.g., Penabad et al., *Lupus*, 2014 October; 23(12):1324-6. ARC1005 (Novo Nordisk, Bagsvaerd, Denmark), SOMAmers (SomaLogic, Boulder, Colo.), SOB1002 (Swedish Orphan Biovitrum, Stockholm, Sweden), RA101348 (Ra Pharmaceuticals, Cambridge, Mass.), Aurin Tricarboxylic Acid ("ATA"), and anti-C5-siRNA (Alnylam Pharmaceuticals, Cambridge, Mass.), and Ornithodoros moubata C inhibitor ('OmCI").

In certain embodiments, the inhibitor is a C5a inhibitor. Any C5a inhibitor can be used. The C5a inhibitor, for example, can be an antibody or a polypeptide.

One example of an anti-C5a antibody is CLS026. CLS026 is a monoclonal antibody specific for murine C5a. CLS026 was derived from a phage display library using conventional panning techniques, with negative selection against human C5 and converted to a full length IgG. This neoepitope specific antibody binds to its target, murine C5a, with single digit nM affinity, as shown with bio-layer interferometry. CLS026 was cultured in CHO cells and purified using single step affinity chromatography with mabselect Xtra (GE) protein A resin. CLS026 was free of endotoxin and determined to be greater than 95% pure using capillary electrophoresis. See also the anti-C5a antibodies from Biocompare, South San Francisco, Calif.

In some embodiments, the antibody is humanized anti-C5a monoclonal antibody.

In some embodiments, the antibody is an anti-C5a antibody having with a light chain depicted in SEQ ID NO:47 and a heavy chain depicted in SEQ ID NO:48 or SEQ ID NO: 49.

In some embodiments, an antibody inhibitor is not a whole antibody. In some embodiments, an antibody inhibitor is an antigen-binding fragment of an antibody that is a single chain antibody.

In some embodiments, an antibody inhibitor is a bispecific antibody. In some embodiments, an antibody is a humanized monoclonal antibody, a chimeric monoclonal antibody, or a human monoclonal antibody, or an antigen binding fragment of any of them.

In some embodiments, an antibody is an antibody or an antigen binding fragment thereof, or a poplypeptide comprising the same. The antibody can be a monoclonal antibody. In other embodiments, the inhibitor comprises the variable region, or a fragment thereof, of an antibody, such as a monoclonal antibody. In other embodiments, the antibody is an immunoglobulin that binds specifically to a C5 complement protein or to a C5a complement protein. In other embodiments, the polypeptide agent is an engineered protein or a recombinant protein. In some embodiments, the antibody agent is not a whole antibody, but comprises parts of an antibody. In some embodiments, the inhibitor is a single chain antibody. In some embodiments, the inhibitor is a bispecific antibody. In some embodiments, the antibody is a humanized monoclonal antibody, a chimeric monoclonal antibody, or a human monoclonal antibody, or an antigen binding fragment of any of them. Methods of making a polypeptide agent, including antibodies, are known in the art.

As stated above, the C5 inhibitor, including a C5-binding polypeptide, can inhibit complement component C5. In particular, the inhibitors, including polypeptides, inhibit the generation of the C5a anaphylatoxin, or the generation of c5a and the C5b active fragments of a complement component C5 protein (e.g., a human C5 protein). Accordingly, the C5 inhibitors inhibit, e.g., the pro-inflammatory effects of C5a; and can inhibit the generation of the C5b-9 membrane attack complex ("MAC") at the surface of a cell and subsequent cell lysis. See, e.g., Moongkarndi et al. (1982) *Immunobiol* 162:397 and Moongkarndi et al. (1983) *Immunobiol* 165:323.

Suitable methods for measuring inhibition of C5 cleavage are known in the art. For example, the concentration and/or physiologic activity of C5a and/or C5b in a body fluid can be measured by methods well known in the art. Methods for measuring C5a concentration or activity include, e.g., chemotaxis assays, RIAs, or ELISAs (see, e.g., Ward and Zvaifler (1971) *J Clin Invest* 50(3):606-16 and Wurzner et al. (1991) *Complement Inflamm* 8:328-340). For C5b, hemolytic assays or assays for soluble C5b-9 known in the art can be used. Other assays known in the art can also be used.

For those C5 inhibitors that also inhibit TCC formation, inhibition of complement component C5 can also reduce the cell lysing ability of complement in a subject's body fluids. Such reductions of the cell-lysing ability of complement present can be measured by methods well known in the art such as, for example, by a conventional hemolytic assay such as the hemolysis assay described by Kabat and Mayer (eds), "Experimental Immunochemistry, 2nd Edition," 135-240, Springfield, Ill., C C Thomas (1961), pages 135-139, or a conventional variation of that assay such as the chicken erythrocyte hemolysis method as described in, e.g., Hillmen et al. (2004) *N Engl J Med* 350(6):552.

In some embodiments, the C5-binding polypeptides are variant antibodies of an anti-C5 antibody (such as eculizumab) that still bind to the antigen, including deletion variants, insertion variants, and/or substitution variants. See, e.g., the polypeptides depicted in SEQ ID NO:1, SEQ ID NO:2, or SEQ ID NO:7 and SEQ ID NO:8. Methods of making such variants, by, for example, recombinant DNA technology, are well known in the art.

In some embodiments, an inhibitor comprises an antibody as part of a fusion protein. The fusion protein can be constructed recombinantly such that the fusion protein is expressed from a nucleic acid that encodes the fusion protein. The fusion protein can comprise one or more C5-binding polypeptide segments (e.g., C5-binding segments depicted in SEQ ID NO:1, SEQ ID NO:2, or SEQ ID NO:5 and/or SEQ ID NO:6, SEQ ID NO: 7 and/or SEQ ID NO: 8, or any one or more of SEQ ID NOs:9-16) and one or more segments that are heterologous to the C5-binding segment(s). The heterologous sequence can be any suitable sequence, such as, for example, an antigenic tag (e.g., FLAG, polyhistidine, hemagglutinin ("HA"), glutathione-S-transferase ("GST"), or maltose-binding protein ("MBP")). Heterologous sequences can also be proteins useful as diagnostic or detectable markers, for example, luciferase, green fluorescent protein ("GFP"), or chloramphenicol acetyl transferase ("CAT"). In some embodiments, the heterologous sequence can be a targeting moiety that targets the C5-binding segment to a cell, tissue, or microenvironment of interest. In some embodiments, the targeting moiety is a soluble form of a human complement receptor (e.g., human complement receptor 2) or an antibody (e.g., a single chain antibody) that binds to C3b or C3d. In some embodiments, the targeting moiety is an antibody that binds to a tissue-specific antigen, such as a kidney-specific antigen. Methods of constructing such fusion proteins, such as by recombinant DNA technology, are well known in the art.

In some embodiments, the antibody, or an antigen-binding fragment thereof, is fused to a targeting moiety. For example, a construct can contain a C5-binding polypeptide and a targeting moiety that targets the polypeptide to a site of complement activation. Such targeting moieties can include, e.g., soluble form of complement receptor 1 (CR1), a soluble form of complement receptor 2 (CR2), or an antibody (or antigen-binding fragment thereof) that binds to C3b and/or C3d.

Methods for generating fusion proteins (e.g., fusion proteins containing a C5-binding polypeptide and a soluble form of human CR1 or human CR2), including recombinant DNA technology, are known in the art and described in, e.g., U.S. Pat. No. 6,897,290; U.S. patent application publication no. 2005265995; and Song et al. (2003) *J Clin Invest* 11(12):1875-1885.

In certain embodiments, the inhibitor is a bispecific antibody. Methods for producing a bispecific antibody (e.g., a bispecific antibody comprising an anti-C5 antibody and an antibody that binds to C3b and/or C3d) are also known in the art. A bispecific antibody comprising a C5-binding antibody and any other antibody is contemplated.

A wide variety of bispecific antibody formats are known in the art of antibody engineering and methods for making the bispecific antibodies (e.g., a bispecific antibody comprising an anti-C5 antibody [i.e., a C5-binding antibody] and an antibody that binds to C3b, C3d, or a tissue-specific antigen) are well within the purview of those skilled in the art. See, e.g., Suresh et al. (1986) *Methods in Enzymology* 121:210; PCT Publication No. WO 96/27011; Brennan et al. (1985) *Science* 229:81; Shalaby et al., *J. Exp. Med.* (1992) 175:217-225; Kostelny et al. (1992) *J Immunol* 148(5): 1547-1553; Hollinger et al. (1993) *Proc Natl Acad Sci USA* 90:6444-6448; Gruber et al. (1994) *J Immunol* 152:5368; and Tutt et al. (1991) *J Immunol* 147:60.

Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques. U.S. Pat. No. 5,534,254 describes several different types of bispecific antibodies including, e.g., single chain Fv fragments linked together by peptide couplers, chelating agents, or chemical or disulfide couplings. In another example, Segal and Bast [(1995) *Curr Protocols Immunol Suppl.* 14:2.13.1-2.13.16] describes methods for chemically cross-linking two monospecific antibodies to thus form a bispecific antibody. A bispecific antibody can be formed, e.g., by conjugating two single chain antibodies which are selected from, e.g., a C5-binding antibody and an antibody that binds to, e.g., C3b, C3d, or a lung-specific antigen, an eye-specific antigen, a kidney-specific antigen, etc.

The bispecific antibody can be a tandem single chain (sc) Fv fragment, which contains two different scFv fragments covalently tethered together by a linker (e.g., a polypeptide linker). See, e.g., Ren-Heidenreich et al. (2004) *Cancer* 100:1095-1103 and Korn et al. (2004) *J Gene Med* 6:642-651. Examples of linkers can include, but are not limited to, $(Gly_4Ser)_2$ [GGGGSGGGGS, SEQ ID NO:17], $(Gly_4Ser)_3$ [GGGGSGGGGSGGGGS, SEQ ID NO:18], $(Gly_3Ser)_4$ [GGGSGGGSGGGSGGGS, SEQ ID NO:19], $(G_3S)$ [GGGS, SEQ ID NO:20], $SerGly_4$ [SGGGG, SEQ ID NO:21], and $SerGly_4SerGly_4$ [SGGGGSGGGG, SEQ ID NO:22].

In some embodiments, the linker can contain, or be, all or part of a heavy chain polypeptide constant region such as a CH1 domain as described in, e.g., Grosse-Hovest et al. (2004) *Proc Natl Acad Sci USA* 101:6858-6863. In some embodiments, the two antibody fragments can be covalently tethered together by way of a polyglycine-serine or polyserine-glycine linker as described in, e.g., U.S. Pat. Nos. 7,112,324 and 5,525,491, respectively. See also U.S. Pat. No. 5,258,498. Methods for generating bispecific tandem scFv antibodies are described in, e.g., Maletz et al. (2001) *Int J Cancer* 93:409-416; Hayden et al. (1994) *Ther Immunol* 1:3-15; and Honemann et al. (2004) *Leukemia* 18:636-644. Alternatively, the antibodies can be "linear antibodies" as described in, e.g., Zapata et al. (1995) *Protein Eng.* 8(10):1057-1062. Briefly, these antibodies comprise a pair of tandem Fd segments ($V_H$-$C_H$1-$V_H$-$C_H$1) that form a pair of antigen binding regions.

A bispecific antibody can also be a diabody. Diabody technology described by, e.g., Hollinger et al. (1993) *Proc Natl Acad Sci USA* 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. See also Zhu et al. (1996) *Biotechnology* 14:192-196 and Helfrich et al. (1998) *Int J Cancer* 76:232-239. Bispecific single chain diabodies ("scDb") as well as methods for generating scDb are described in, e.g., Brusselbach et al. (1999) *Tumor Targeting*

4:115-123; Kipriyanov et al. (1999) *J Mol Biol* 293:41-56; and Nettlebeck et al. (2001) *Mol Ther* 3:882-891.

Variant forms of bispecific antibodies such as the tetravalent dual variable domain immunoglobulin (DVD-Ig) molecules described in Wu et al. (2007) *Nat Biotechnol* 25(11): 1290-1297 can also be used in the methods of this invention. The DVD-Ig molecules are designed such that two different light chain variable domains ($V_L$) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024188 and WO 07/024715. Also embraced is the bispecific format described in, e.g., U.S. patent application publication no. 20070004909. Another bispecific format that can be used is the Cross-Over Dual V Region (CODV-Ig) which is a format for engineering four domain antibody-like molecules described in WO2012/135345. CODV-Ig was shown to be useful in engineering bispecific antibody-like molecules where steric hindrance at the C-terminal V domains (internal) may prevent construction of a DVD-Ig.

The C5-binding antibodies or the C5a-binding antibodies and/or targeting-moieties that are used to form the bispecific antibody molecules can be, e.g., chimeric, humanized, rehumanized, deimmunized, or fully human, all of which are well known in the art.

C5 and C5a inhibitors that are small molecule chemical compounds can be produced by methods known in the art.

The C5-binding inhibitors and the C5a-binding inhibitors, including polypeptides and antibodies, can be produced using a variety of techniques known in the art of molecular biology and protein chemistry.

For example, a nucleic acid encoding a C5-binding polypeptide (e.g., a C5-binding polypeptide comprising or consisting of the amino acid sequence depicted in SEQ ID NO:2) or a C5a-binding polypeptide can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

An exemplary nucleic acid, which encodes an exemplary C5-binding polypeptide (Pexelizumab), is as follows:
GATATCCA-
GATGACCCAGTCCCCGTCCTCCCTGTCCGCCTCTGT
GGGCGATAGGGTCACCATCA
CCTGCGGCGCCAGCGAAAACATCTATGGCGCGCT-
GAACTGGTATCAACAGAAACCCGGGAAAGC
TCCGAAGCTTCTGATT-
TACGGTGCGACGAACCTGGCAGATG-
GAGTCCCTTCTCGCTTCTCTGGA TCCGGCTCCG-
GAACGGATTTCACTCTGACCATCAGCAGTCTGCAG
CCTGAAGACTTCGCTACGT
ATTACTGTCAGAACGTTT-
TAAATACTCCGTTGACTTTCGGACAGGGTAC-
CAAGGTGGAAATAAA
ACGTACTGGCGGTGGTGGTTCTGGTGGCGGTG-
GATCTGGTGGTGGCGGTTCTCAAGTCCAACTG
GTGCAATCCGGCGCCGAGGT-
CAAGAAGCCAGGGGCCTCAGT-
CAAAGTGTCCTGTAAAGCTAGCG GCTATAT-
TTTTTCTAATTATTGGATTCAATGGGTGCGTCAGGC
CCCCGGGCAGGGCCTGGAATG GATGGGT-
GAGATCT-
TACCGGGCTCTGGTAGCACCGAATATACCGAAAAT-
TTTAAAGACCGTGTT
ACTATGACGCGTGACACTTCGACTAGTACAGTATA-
CAT
GGAGCTCTCCAGCCTGCGATCGGAGG
ACACGGCCGTCTATTATTGCGCGCGTTAT-
TTTTTTGGTTCTAGCCCGAATTGGTATTTTGATGT
TTGGGGTCAAGGAACCCTGGT-
CACTGTCTCGAGCTGA (SEQ ID NO:1). In some embodiments, the nucleic acid comprises nucleotides 1-738 of SEQ ID NO:1, e.g., in embodiments where carboxyl-terminal fusion proteins are to be generated or produced.

Several possible vector systems (such as plasmid vector systems) well known in the art are available for the expression of C5-binding or C5a-binding polypeptides from nucleic acids in a number of cells, including in mammalian cells.

The expression vectors can be introduced by methods well known in the art into cells in a manner suitable for subsequent expression of the nucleic acid.

An antibody, or an antigen-binding fragment thereof, can be expressed in any appropriate host cells. Appropriate host cells include, for example, yeast, bacteria, insect, plant, and mammalian cells, including bacteria such as *E. coli*, fungi such as *Saccharomyces cerevisiae* and *Pichia pastoris*, insect cells such as SF9, mammalian cell lines (e.g., human cell lines), primary cell lines (e.g., primary mammalian cells), Chinese hamster ovary ("CHO") cells, and a suitable myeloma cell line such as NSO.

In some embodiments, an antibody, or an antigen-binding fragment thereof, can be expressed in, and purified from, transgenic animals (e.g., transgenic mammals). For example, a C5-binding polypeptide can be produced in transgenic non-human mammals (e.g., rodents, sheep or goats) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The antibody, or an antigen-binding fragment thereof, can be produced from cells by culturing a host cell transformed with the expression vector containing nucleic acid encoding the polypeptides, under conditions, and for an amount of time, sufficient to allow expression of the proteins. Such conditions for protein expression will vary with the choice of the expression vector and the host cell, and will be easily ascertained by one skilled in the art through routine experimentation. See, e.g., Current Protocols in Molecular Biology, Wiley & Sons, and Molecular Cloning—A Laboratory Manual—3rd Ed., Cold Spring Harbor Laboratory Press, New York (2001), which has comprehensive disclosure of recombinant DNA technology.

Following expression, the antibody, or an antigen-binding fragment thereof, can be isolated or purified in a variety of ways known to those skilled in the art.

The C5-binding polypeptides, as well as other C5 inhibitors, specifically bind to a human complement component C5 protein; the anti-C5a agents, such as an anti-C5a antibody, specifically binds to a human complement component C5a. The terms "specific binding" or "specifically binds" are known in the art and, briefly, can refer to two molecules forming a complex (e.g., a complex between a C5 inhibitor, including a C5-binding polypeptide, and a complement component C5 protein) that is relatively stable under physiologic conditions.

Methods for determining whether an antibody binds, including "specifically binds," to an antigen and/or the affinity for an antibody to an antigen are known in the art. For example, the binding of an antibody to an antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2nd Edition, Oxford University Press, NY, Oxford; Johne et al. (1993) J Immunol Meth 160:191-198; Jonsson et al. (1993) *Ann Biol Clin* 51:19-26; and Jonsson et al. (1991) *Biotechniques* 11:620-627.

Methods of making, identifying, purifying, modifying, etc. an agent for use in methods disclosed herein are well known in the art.

Pharmaceutical Compositions and Formulations

Compositions containing an inhibitor for use in methods disclosed herein can be formulated as a pharmaceutical composition for administering to a subject for treating AMD. Any suitable pharmaceutical compositions and formulations, as well as suitable methods for formulating and suitable routes and suitable sites of administration, are within the scope of this invention, and are known in the art. Also, any suitable dosage(s) and frequency of administration are contemplated.

The pharmaceutical compositions can include a pharmaceutically acceptable carrier. A "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J Pharm Sci* 66:1-19).

In certain embodiments, those that are protein compositions can be stabilized and formulated as a solution, microemulsion, dispersion, liposome, lyophilized (freeze-dried) powder, or other ordered structure suitable for stable storage at high concentration. Sterile injectable solutions can be prepared by incorporating a C5-binding or a C5a-binding polypeptide, for use in the methods disclosed herein, in the required amount in an appropriate solvent with one or a combination of ingredients enumerated above, as required, followed by filtered sterilization. Generally, dispersions are prepared by incorporating a C5-binding polypeptide into a sterile vehicle that contains a basic dispersion medium and the required other ingredients from those enumerated above. In the case of sterile powders for the preparation of sterile injectable solutions, methods for preparation include vacuum drying and freeze-drying that yield a powder of an inhibitor polypeptide plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin. Non-protein inhibitors can be formulated in the same, or similar, way.

The C5 inhibitor, including a C5-binding polypeptide, such as eculizumab, an antigen-binding fragment thereof, an antigen-binding variant thereof, a polypeptide comprising the antigen-binding fragment of eculizumab or the antigen-binding fragment of an eculizumab variant, a fusion protein comprising the antigen binding fragment of eculizumab or the antigen-binding fragment of an eculizumab variant, or a single chain antibody version of eculizumab or of an eculizumab variant, and an C5a inhibitor, can be formulated at any desired concentration, including relatively high concentrations in aqueous pharmaceutical solutions. For example, a C5-binding polypeptide, such as eculizumab, an antigen-binding fragment thereof, an antigen-binding variant thereof, a polypeptide comprising the antigen-binding fragment of eculizumab or the antigen-binding fragment of an eculizumab variant, a fusion protein comprising the antigen binding fragment of eculizumab or the antigen-binding fragment of an eculizumab variant, or a single chain antibody version of eculizumab or of an eculizumab variant, can be formulated in solution at a concentration of between about 10 mg/mL to about 100 mg/mL, or more, (e.g., between about 9 mg/mL and about 90 mg/mL; between about 9 mg/mL and about 50 mg/mL; between about 10 mg/mL and about 50 mg/mL; between about 15 mg/mL and about 50 mg/mL; between about 15 mg/mL and about 110 mg/mL; between about 15 mg/mL and about 100 mg/mL; between about 20 mg/mL and about 100 mg/mL; between about 20 mg/mL and about 80 mg/mL; between about 25 mg/mL and about 100 mg/mL; between about 25 mg/mL and about 85 mg/mL; between about 20 mg/mL and about 50 mg/mL; between about 25 mg/mL and about 50 mg/mL; between about 30 mg/mL and about 100 mg/mL; between about 30 mg/mL and about 50 mg/mL; between about 40 mg/mL and about 100 mg/mL; between about 50 mg/mL and about 100 mg/mL; or between about 20 mg/mL and about 50 mg/mL); or at any suitable concentration. A C5-binding polypeptide used in the methods of this invention can be present in the solution at greater than (or at least equal to) about 5 (e.g., greater than, or at least equal to, about any of the following: 5, 6, 7, 8, 9, 10, 11, 12, 13, 14, 15, 16, 17, 18, 19, 20, 21, 22, 23, 24, 25, about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, or even 150, or more) mg/mL. A C5-binding polypeptide, such as eculizumab, an antigen-binding fragment thereof, an antigen-binding variant thereof, a polypeptide comprising the antigen-binding fragment of eculizumab or the antigen-binding fragment of an eculizumab variant, a fusion protein comprising the antigen binding fragment of eculizumab or the antigen-binding fragment of an eculizumab variant, or a single chain antibody version of eculizumab or of an eculizumab variant, can be formulated at a concentration of greater than about 2 (e.g., greater than about any of the following: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 or more) mg/mL, but less than about 55 (e.g., less than about any of the following: 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or less than about 5) mg/mL. Thus, in some embodiments, a C5-binding polypeptide, such as eculizumab, an antigen-binding fragment thereof, an antigen-binding variant thereof, a polypeptide comprising the antigen-binding fragment of eculizumab or the antigen-binding fragment of an eculizumab variant, a fusion protein comprising the antigen binding fragment of eculizumab or the antigen-binding fragment of an eculizumab variant, or a single chain antibody version of eculizumab or of an eculizumab variant, can be formulated in an aqueous solution at a concentration of greater than about 5 mg/mL and less than about 55 mg/mL. A C5-binding polypeptide, such as eculizumab, an antigen-binding fragment thereof, an antigen-binding variant thereof, a polypeptide comprising the antigen-binding fragment of eculizumab or the antigen-binding fragment of an eculizumab variant, a fusion protein comprising the antigen binding fragment of eculizumab or the antigen-binding fragment of an eculizumab variant, or a single chain antibody version of eculizumab or of an eculizumab variant, can be formulated in an aqueous solution at a concentration of about 50 mg/mL. Any suitable concentration is contemplated. Methods for formulating a protein in an aqueous solution are known in the art and are described in, e.g., U.S. Pat. No. 7,390,786; McNally and Hastedt (2007), "Protein Formulation and Delivery," Second Edition, *Drugs and the Pharmaceutical Sciences*, Volume 175, CRC Press; and Banga (1995), "Therapeutic peptides and proteins: formulation, processing, and delivery systems," CRC Press.

The dosage level for an inhibitor agent can be any suitable level. In certain embodiments, the dosage levels of an C5-binding polypeptide, such as eculizumab, an antigen-binding fragment thereof, an antigen-binding variant thereof, a polypeptide comprising the antigen-binding fragment of eculizumab or the antigen-binding fragment of an eculizumab variant, a fusion protein comprising the antigen binding fragment of eculizumab or the antigen-binding fragment of an eculizumab variant, or a single chain antibody version of eculizumab or of an eculizumab variant, for human subjects can generally be between about 1 mg per kg and about 100 mg per kg per patient per treatment, and can be between about 5 mg per kg and about 50 mg per kg per patient per treatment.

The plasma concentration in a patient, whether the highest level achieved or a level that is maintained, of an inhibitor agent can be any desirable or suitable concentration. Such plasma concentration can be measured by methods known in the art.

In some embodiments, the inhibitor, either a C5 inhibitor or a C5a inhibitor, is administered intravenously to the subject (the term "subject" is used herein interchangeably with the term "patient"), including by intravenous injection or by intravenous infusion. In some embodiments, the inhibitor, either a C5 inhibitor or a C5a inhibitor, is administered to the subject intravitreally or intraocularly, including by injection. In some embodiments, the inhibitor agent, either a C5 inhibitor or a C5a inhibitor, is administered intravenously and intravitreally or intraocularly.

An inhibitor agent, either a C5 inhibitor or a C5a inhibitor, can be administered to a subject as a monotherapy. In some embodiments, the methods described herein can include administering to the subject one or more additional treatments, such as one or more additional therapeutic agents.

The additional treatment can be any additional treatment, including experimental treatment for AMD, or a treatment for a symptom of AMD. The other treatment can be any treatment (any therapeutic agent) that improves or stabilizes the patient's health. The additional therapeutic agent(s) includes IV fluids, such as water and/or saline, acetaminophen, conventional AMD treatment such as EYLEA®, LUCENTIS®, AND MACUGEN®, etc. The one or more additional therapeutic agents can be administered together with the C5 inhibitor or C5a inhibitor as separate therapeutic compositions or one therapeutic composition can be formulated to include both: (i) one or more anti-C5 agent or anti-C5a agent and (ii) one or more additional therapeutic agents. An additional therapeutic agent can be administered prior to, concurrently, or after administration of the anti-C5 agent or anti-C5a agent. An additional agent and an anti-C5 agent or anti-C5a agent, can be administered using the same delivery method or route or using a different delivery method or route. The additional therapeutic agent can be another complement inhibitor, including another C5 inhibitor or another C5a inhibitor (anti-C5a agent).

In some embodiments, a C5 inhibitor or a C5a inhibitor can be formulated with one or more additional active agents useful for treating AMD in a patient.

When a C5 inhibitor or a C5a inhibitor is to be used in combination with a second active agent, the agents can be formulated separately or together. For example, the respective pharmaceutical compositions can be mixed, e.g., just prior to administration, and administered together or can be administered separately, e.g., at the same or different times, by the same route or different route.

In some embodiments, a composition can be formulated to include a sub-therapeutic amount of a C5 inhibitor or a C5a inhibitor and a sub-therapeutic amount of one or more additional active agents such that the components in total are therapeutically effective for treating AMD. Methods for determining a therapeutically effective dose of an agent such as a therapeutic antibody are known in the art.

The compositions can be administered to a subject, e.g., a human subject, using a variety of methods that depend, in part, on the route of administration. The route can be, e.g., intravenous ("IV") injection or infusion, subcutaneous ("SC") injection, intraperitoneal ("IP") injection, pulmonary delivery such as by intrapulmonary injection, intraocular injection, intraarticular injection, intravitreal injection, or intramuscular ("IM") injection.

A suitable dose of a C5 inhibitor or a C5a inhibitor, which dose is capable of treating or preventing AMD in a subject, can depend on a variety of factors including, e.g., the age, gender, and weight of a subject to be treated and the particular inhibitor compound used. Other factors affecting the dose administered to the subject include, e.g., the type or severity of AMD. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

A C5 inhibitor or a C5a inhibitor can be administered as a fixed dose, or in a milligram per kilogram (mg/kg) dose. In some embodiments, the dose can also be chosen to reduce or avoid production of antibodies or other host immune responses against one or more of the active antibodies in the composition.

A pharmaceutical composition can include a therapeutically effective amount of a C5 inhibitor or a C5a inhibitor. Such effective amounts can be readily determined by one of ordinary skill in the art.

The terms "therapeutically effective amount" or "therapeutically effective dose," or similar terms used herein are intended to mean an amount of a C5 inhibitor or a C5a inhibitor that will elicit the desired biological or medical response. A therapeutically effective amount of a C5 inhibitor or a C5a inhibitor can include an amount (or various amounts in the case of multiple administration) that improves or maintains the patient's vision, decreases IL-17 level in the eye, decreases inflammation in the eye, decreases the level of γδT-cells in the eye, reduced the production of Th17- and γδT-cells in the spleen, reduced CNV size, or any combination thereof. All of these parameters can be ascertained or measured by known methods to a person skilled in the art.

In some embodiments, a composition described herein contains a therapeutically effective amount of a C5 inhibitor or a C5a inhibitor. In some embodiments, the composition contains any of a C5 inhibitor or a C5a inhibitor, and one or more (e.g., one, two, three, four, five, six, seven, eight, nine, ten, or eleven or more) additional therapeutic agents such that the composition as a whole is therapeutically effective. For example, a composition can contain a C5 inhibitor or C5a inhibitor and an immunosuppressive agent, wherein the polypeptide and agent are each at a concentration that when combined are therapeutically effective for treating or preventing AMD in a subject.

A "subject," as used herein, can be a human. The term "patient" is used herein interchangeably with the term "subject." In certain embodiments, the patient (or the subject) is a human patient (or human subject).

EXAMPLES

For this invention to be better understood, the following examples are set forth. These examples are for purposes of illustration only and are not be construed as limiting the scope of the invention in any manner.

Example 1

Treating Wet AMD in a Mouse Model with an C5 Inhibitor and/or C5a Inhibitor

Neovascular age-related macular degeneration (AMD) is characterized by choroidal neovascularization (CNV). An overactive complement system may contribute to AMD pathogenesis, and serum pro-inflammatory cytokines, including IL-17, are elevated in AMD patients. IL-17 is produced by anaphylatoxin C5a receptor-expressing T-cells. CNV lesions were generated in mice using laser photocoagulation and quantified by imaging; and T-lymphocytes were characterized by QRT-PCR. CNV resulted in an increase in splenic IL-17-producing γδT- and Th17-cells; yet in the CNV eye, only elevated levels of γδT-cells could be observed.

Administration of anti-C5 or anti-C5a-blocking antibodies to reduce levels of C5a production in the eye, blunted the CNV-induced production of splenic Th17- and γδT-cells, reduced CNV size and eliminated ocular γδT-cell infiltration. In ARPE-19 cell monolayers, IL-17 triggered a pro-inflammatory state; and T-cell proliferation was elevated in response to ocular proteins. Taken together, CNV lesions trigger a systemic immune response, augmenting local ocular inflammation via the infiltration of IL-17-producing γδT-cells, which are presumably recruited to the eye in a C5a-dependent manner.

C57BL/6J mice were generated from breeding pairs (Jackson Laboratories, Bar Harbor, Me.). Animals were housed under a 12:12 hour, light:dark cycle with access to food and water ad libitum.

CNV lesions were induced as described in Rohrer, B. et al. *Invest Ophthalmol Vis Sci* 50, 3056-3064. Briefly, 3- to 4-month-old mice were anesthetized (xylazine and ketamine, 20 and 80 mg/kg, respectively) and pupils dilated (2.5% phenylephrine HCl and 1% atropine sulfate), using argon laser photocoagulation (532 nm, 100 μm spot size, 0.1 s duration, 100 mW) to generate four laser spots per eye surrounding the optic nerve, using a handheld coverslip as a contact lens. Any laser spots not creating a lesion (indicated by bubble formation), or those accidentally rupturing a blood vessel were excluded from size determination by ICAM2 staining or optical coherence (OCT) analysis.

CNV size determination was accomplished by ICAM2 staining or OCT analysis. Briefly, for immunofluorescence, eyes were enucleated, fixed in 4% paraformaldehyde and eyecups stained for CD102 (also referred to as ICAM2; 0.5 mg/mL at 1:200; BD Pharmingen, San Diego, Calif.) followed by visualization with an Alexa-488-coupled secondary antibody (2 mg/mL at 1:400; Invitrogen, Grand Island, N.Y.). A Z-stack of 2 m optical sections through the entire depth of the CNV lesion was obtained using confocal microscopy (40× oil lens; fixed laser intensity setting for all experiments). For each optical section, the amount of fluorescence was determined which was used to determine pixel intensity against depth (area under the curve provides indirect volume measurement). Rohrer, B. et al. *Invest Ophthalmol Vis Sci* 50, 3056-3064, (2009). A Z-stack away from the CNV lesions was collected for background subtraction. For size determination using OCT, a SD-OCT BIOPTIGEN® Spectral Domain Ophthalmic Imaging System (Bioptigen Inc., Durham, N.C.) was utilized. Mice were anesthetized and eyes hydrated with normal saline. Using the BIOPTIGEN® InVivoVue software, rectangular volume scans were performed (1.6×1.6 mm; 100 B-scans, 1000 A-scans per B scan), and using the systems en face fundus reconstruction tool the center of the lesion was determined and the image saved. ImageJ software (Wayne Rasband, National Institutes of Health, Bethesda, Md. was then used to measure the area around the hyporeflective spot produced in the fundus image. Giani, A. et al. *Invest Ophthalmol Vis Sci* 52, 3880-3887. Data for both imaging modalities were expressed as mean±SEM.

CLS026 is a monoclonal antibody specific for murine C5a. CLS026 was derived from a phage display library using conventional panning techniques, with negative selection against human C5 and converted to a full length IgG. This neoepitope specific antibody binds to its target, murine C5a, with single digit nM affinity, as shown with bio-layer interferometry. CLS026 was cultured in CHO cells and purified using single step affinity chromatography with mabselect Xtra (GE) protein A resin. CLS026 was free of endotoxin and determined to be greater than 95% pure using capillary electrophoresis.

ELISA was used to determine levels of mouse C5a. For the quantitative determination of mouse C5a in RPE/choroid tissue homogenates, a sandwich enzyme immunoassay was used according to the manufacturer's instructions (Kamiya Biomedical Company; Seattle, Wash.). In short, pre-coated plates were exposed to the antigen for 2 hours at 37° C., washed and incubated with detection antibody to C5a followed by peroxidase-conjugated secondary antibody and color development using TMB substrate. The concentrations of C5a in the ocular samples were determined by comparing the O.D. of the samples to a calibration curve (calibrators provided in the kit).

Quantitative RT-PCR (QRT-PCR) was used to assess mRNA levels for genes of interest. ARPE-19 cells or RPE-choroid-sclera (referred to as RPE-choroid) fractions isolated from control and CNV eyes were utilized and processed as described before. Dunkelberger, J. R. & Song, W. C. *Cell Res* 20, 34-50, doi:10.1038/cr.2009.139 (2010); Rohrer, B. et al. *Invest Ophthalmol Vis Sci* 50, 3056-3064, (2009). In short, real-time PCR analyses were performed in triplicate in a GENEAMP® 5700 Sequence Detection System (Applied Biosystems, Foster City, Calif.) using standard cycling conditions. Quantitative values were obtained by the cycle number. Significance required both a ±2-fold difference and P<0.05 between the relevant comparisons. Primers used are listed in Table 1.

TABLE 1

QRT-PCR Primer Sequences

|  | Forward | Reverse |
|---|---|---|
| Mouse Primers | | |
| β-actin | 5'-AAATCTGGCACCACACCTTC-3' (SEQ ID NO: 23) | 5'-GGGGTGTTGAAGGTCTCAAA-3' (SEQ ID NO: 24) |
| C3 | 5'-TCAGATAAGGAGGGGCACAA-3' (SEQ ID NO: 25) | 5'-ATGAAGAGGTACCCACTCTGGA-3' (SEQ ID NO: 26) |
| C5 | 5'-CAGGGTACTTTGCCTGCTGA-3' (SEQ ID NO: 27) | 5'-TGGATTTTCATGGTGGGGCA-3' (SEQ ID NO: 28) |
| VEGF | 5'-CTGGACCCTGGCTTTACTGC-3' (SEQ ID NO: 29) | 5'-TGAACTTGATCACTTCATGGGACT-3' (SEQ ID NO: 30) |
| IL-17 | 5'-TTCAGGGTCGAGAAGATGCT-3' (SEQ ID NO: 31) | 5'-AAACGTGGGGGTTTCTTAGG-3' (SEQ ID NO: 32) |
| ROR gamma | 5'-CGACTGGAGGACCTTCTACG-3' (SEQ ID NO: 33) | 5'-TTGGCAAACTCCACCACATA-3' (SEQ ID NO: 34) |
| T cell Receptor | 5'-CAGGCACTTACATCCACTGGT-3' (SEQ ID NO: 35) | 5'-TGAATCTGGAATCCACCACAG-3' (SEQ ID NO: 36) |
| Human Primers | | |
| β-actin | 5'-AAATCTGGCACCACACCTTC-3' (SEQ ID NO: 37) | 5'-GGGGTGTTGAAGGTCTCAAA-3' (SEQ ID NO: 38) |
| C3 | 5'-ACCACACCCTCCAAACAAAG-3' (SEQ ID NO: 39) | 5'-ACTGTCTTCTCCACGGTGCT-3' (SEQ ID NO: 40) |
| VEGF | 5'0-TCTTCAAGCCATCCTGTGTC-3' (SEQ ID NO: 41) | 5'-ATCCGCATAATCTGCATGGT-3' (SEQ ID NO: 42) |
| IL-17 | 5'-GCAATGAGGACCCTGAGAGA-3' (SEQ ID NO: 43) | 5'-TGGATGGGGACAGAGTTCAT-3' (SEQ ID NO: 44) |
| Factor H | 5'-AGAAGGCACCCAGGCTATCT-3' (SEQ ID NO: 45) | 5'-CACAGGGCCTTTTCTGACAT-3' (SEQ ID NO: 46) |

ARPE-19 cells, a human RPE cell line that displays the differentiated phenotype of RPE cells, were grown as described previously. Thurman, J. M. et al. *J Biol Chem* 284, 16939-16947, (2009). Cells were expanded in DMEM-F12 (Gibco) with 10% fetal bovine serum (FBS) and 1× penicillin:streptomycin until they reached confluence. To promote formation of stable barrier facilities serum was reduced to 2%. Barrier function was assessed based on transepithelial resistance (TER) measurements. The 2% FBS was removed completely for two days, which does not alter survival or monolayer formation, such that cells can be treated with a known concentration of IL-17.

T-cell proliferation assays were performed as published previously. Haq, E., Rohrer, B., Nath, N., Crosson, C. E. & Singh, I. *J Ocul Pharmacol Ther* 23, 221-231, (2007). Briefly, cell suspensions of splenocytes were prepared and the concentration of cells adjusted to $5 \times 10^6$ cells/mL. The cells were grown in RPMI-complete medium containing RPMI-1640 (Gibco BRL Carlsbad, Calif.), 10% FBS, 1× penicillin:streptomycin, 1 mM glutamine, 1 mM nonessential amino acids, and 500 μM 2-ME (Sigma-Aldrich; St. Louis, Mo.). Splenocytes were stimulated with IRBP161-180 (20 g/mL), S-antigen (concentration), and supernatants of solubilized RPE/choroid or retina extracts for 72 hours (h). For proliferation at 48 hours, 1 Ci of [methyl-$^3$H] thymidine (Amersham Biosciences Pittsburgh, Pa.) was added to each well of the plate and the mean incorporation of thymidine into DNA was measured at 72 hours by a 1450 Microbeta Wallac Trilux Liquid Scintillation Counter (Perkin-Elmer Life Sciences, Waltham, Mass.).

Next, a complement hemolysis assay was used. Terminal complement activity in recipient mouse sera was determined by standard methods to assess its ability to lyse chicken erythrocytes, which had been presensitized with erythrocyte-specific Abs as previously described. Wang, H. et al. *Transplantation* 68, 1643-1651 (1999). Briefly, purified anti-C5 mAb at 100, 2, and 0 μg/ml in gelatin Veronal-buffered saline (GVBS) containing 0.1% gelatin, 141 mM NaCl, 0.5 mM MgCl2, 0.15 mM CaCl2, and 1.8 mM sodium barbital was used as low, medium, and 100% lysis controls, respectively. Experimental samples were prepared by diluting the murine test serum 1/10 in GVBS. Control and experimental samples were added, in triplicate, to wells of a 96-well plate containing an equal volume of 10% normal Balb/c mouse serum and 10% human C5-deficient serum in GVBS. Two microliters of 500 mM EDTA was added to the third well of both the 100% lysis and experimental sample triplicates to generate "no hemolysis" color control standards for each condition. Chicken erythrocytes were washed in GVBS, sensitized by incubation with an anti-chicken RBC polyclonal Ab (Intercell Technologies; 0.1% v/v) at 4° C. for 15 min, washed again, and resuspended in GVBS at a final concentration of ~7.5×10$^7$ cells/ml. The sensitized chicken erythrocytes (~2.5×10$^6$ cells) were added to the plate containing the controls and samples, mixed briefly on a plate shaker, and incubated at 37° C. for 30 min. The plate was then mixed again, centrifuged at 3000 rpm for 3 min, and 80 µl of the supernatant was transferred to wells of a 96-well flat-bottom microtiter plate (BD Biosciences). The plate was read at OD415 using a microplate reader and the percentage of hemolysis was determined using the following formula: % hemolysis=100×((OD sample−OD sample color control)/(OD 100% lysis control−OD 100% lysis color control)).

Statistical analysis was performed for data consisting of multiple groups, one-way ANOVA followed by Fisher's post hoc test (P<0.05) was used; single comparisons were analyzed by Student t test analysis (P<0.05); normalized data were analyzed using a Z-test (P<0.05).

Results

IL-17 Expression in the CNV Eye is Correlated with the Presence γδT-Cells Marker.

Induction of severe CNV (40-50 burns per eye) in mice results in a transient increase in ocular infiltrating inflammatory cells, measurable by flow cytometry in pooled eye samples. A small number of T-cells was found to be present between 12 hours and 7 days after induction of the lesions. The presence of marker genes unique to the T-cell types under investigation was used, comparing CNV eyes with four carefully placed lesions to non-lesioned age-matched controls.

To examine the presence and type of T-cells in eyes with CNV, RPE-choroid samples were analyzed using QRT-PCR. In analysis of the data, T-cells were present 6 days after CNV induction, as shown by the expression of CD3a (mature T-cells) and CD4 (T-regulatory cells and T-helper cells) being elevated in lasered eyes when compared to controls (CD3a: 8.0±1.4; CD4: 9.1±1.8). IL-17-producing T-cells, Th17- and γδT-cells, could be distinguished based on the presence of the transcription factor RAR-related orphan receptor gamma (RORγ) and the γδT-cell receptor (γδTR), respectively (FIG. 1). As shown in FIG. 1, Expression of IL-17, RORγ, and γδTR (γδT cell receptor) following CNV were measured at 12 hours, 24 hours, 2 days, 3 days, and 6 days. Levels of IL-17 mRNA peaked at 24 hours following CNV and remained elevated throughout 6 days. γδTR levels were similarly elevated through day 6 with a peak observed at 24 hours. RORγ levels remained unaltered in the presence of CNV. Data shown are average values (±SEM) per sample. Thus, the levels of IL-17 mRNA peaked at 24 hours post CNV induction, and was continuously elevated up to 6 days (latest time point measured). Increased levels of IL-17 correlated with those of the γδT-cell receptor; whereas levels for RORγ were unaltered by the lesions.

The spleen comprises B- and T-cells, which are exposed to antigens directly by filtering them from the blood, or indirectly by delivery by migratory macrophages or dendritic cells. Upon antigen presentation, T-cells can become activated, leading to clonal expansion. Six days after induction of CNV lesions, an equal increase in IL-17, RORγ and γδTR was measured in the spleen, suggestive of an overall activation of T-cells in the spleen (IL-17: 4.04±0.39; RORγ: 4.96±1.16; γδTR: 4.68±0.34) (see also FIG. 6). FIG. 6 shows effects of C5a and C5 on T cells. Splenic (b) and ocular (a) samples were isolated 6 days after induction of CNV and analyzed by QRT-PCR using primers specific for Th-17 (RORγ) and γδT-cells (γδTR). (a) Following CNV, mice treated with anti-C5 and anti-C5a demonstrated a significant decrease in ocular levels of IL-17 and γδTR gene expression, whereas RORγ levels were unaltered. (b). Splenic levels of T-cell-specific genes in CNV mice indicated that RORγ levels returned to control levels in mice treated with anti-C5 and anti-C5a, whereas γδTR remained elevated.

Spleens of CNV mice were collected and the resulting splenocytes stimulated ex vivo by the addition of antigenic stimuli (FIG. 2). T cells derived from spleens of CNV animals were stimulated by various ocular antigens and T cell proliferation was measured. As shown in FIG. 2, splenocytes stimulated by the RPE/choroid (RPE) extracts and the retina proteins IRBP and S-antigen demonstrated a moderate increase (2-3 fold) in proliferation when compared to control; whereas stimulation with retinal extracts resulted in a much larger (6-fold) increase in T cell proliferation. Data shown were average values (±SD) per sample. General stimulation to ocular antigens was provided using retina and RPE-choroid extracts, whereas specific antigen stimulation was provided using IRBP and S-antigen, two well-known antigenic proteins that cause experimental autoimmune uveitis (EAU) in animals. IRBP is a glycoprotein in the interphotoreceptor matrix, S-antigen a soluble photoreceptor cell protein. Both proteins and/or other soluble retina- and RPE-derived proteins may gain access to the blood stream upon generating CNV lesions that break that blood retina barrier. In T-cells derived from CNV animals, exposure to RPE-cell extract caused a modest increase in cell proliferation, whereas retina-extract triggered a massive increase. Purified retina proteins (IRBP and S-antigen) did not mimic the large increase in proliferation seen in the retina-extract group, with both causing a significant but modest increase.

Thus, CNV triggers an immune response involving the adaptive immune response, leading to T-cell proliferation and activation. Despite the increase in both Th17- and γδT-cells in the spleen and hence presumably in the blood stream, only a selective migration of γδT-cells into the eye is associated with CNV.

IL-17 Expression in the CNV Eye is Reduced by Blocking C5a Production or Signaling.

γδT-cells are recruited to the eye in CNV mice. T-cells have been shown to express C5a receptor (C5aR) on their cell surface, which could allow them to migrate towards the source of C5a present in the eye after the induction of CNV lesions. C5a production and C5a-receptor signaling can be reduced by either inhibiting complement activation upstream of the C5 convertase, or by using blocking antibodies or antagonists to C5, C5a or C5aR, respectively.

A blocking antibody against C5 (mouse IgG1) and a novel antibody against mouse C5a (mouse IgG1) were used, the anti-C5 antibody being one used successfully to block C5-dependent antiphospholipid antibody-mediated thrombophilia. Mouse IgG1 antibodies were used since they have little or no antibody-dependent cellular cytotoxicity and complement-dependent cytotoxicity.

To confirm efficacy of the anti-C5 blocking antibody, mice were injected with anti-C5 and control antibody and blood from the mice was collected for hemolysis assays. This tests the functional capability of serum complement components of the classical pathway to lyse sheep red blood cells in a membrane-attack complex-dependent manner. Serum of mice injected with the anti-C5 antibody were unable to lyse sheep red blood cells, confirming successful blockage of complement activation, whereas lysis did occur in mice injected with the control antibody or the antibody against C5a (FIG. 3a).

The monoclonal antibody specific for murine C5a was confirmed to bind to its target, murine C5a, with single digit nM affinity, using bio-layer interferometry (FIG. 3b).

FIG. 3 shows characterization of antibodies. (a) Serum from mice injected with PBS, anti-C5, anti-C5a, and the antibody control 12B4 were analyzed for complement activation through use of a hemolysis assay. Serum from anti-C5 antibody treated animals was unable to lyse sheep red blood cells, indicating successful blockage of complement activation. No significant difference was reported between lysis in mice injected with anti-C5a, PBS or 12B4. Data shown were average values (±SEM) per sample. (b) Specificity of the monoclonal antibody specific for murine C5a was confirmed to bind to its target, murine C5a, with single digit nM affinity, using bio-layer interferometry (data not shown).

The antibodies were tested in the mouse CNV model, after having confirmed that the antibodies can be used as blocking antibodies and/or bind to their targets. The CNV development following laser photocoagulation was assessed in 4 cohorts of mice (mice injected every 48 hours intravenously with PBS, control antibody, anti-C5 or anti-C5a) at 3 months of age. On day 5 after laser-induced CNV, CNV size was measured using OCT (FIG. 4a) in the presence of anti-C5, anti-C5a, or 12B4 (control). OCT images show a decrease in lesion size with treatment of anti-C5 and anti-C5a when compared to control (a). Six days after laser-induced CNV induction, mice were sacrificed and tissues collected. It was demonstrated that CNV development was significantly reduced in mice treated with mouse IgG1 anti-C5 (3666±359.9 pixels) or C5a-blocking (3453±253.8) antibodies when compared to control antibody-injected mice (5572±630.6; P≤0.01; FIG. 4b). Quantification of these results (b) indicated a nearly 40% decrease in lesion size when injected with anti-C5 and anti-C5a (P≤0.01). Data shown were average values (±SEM) per lesion.

ELISA measurements of RPE/choroid confirmed that CNV induction lead to increased C5a levels. Treatment with a C5 blocking antibody, which prevents the generation of C5a, resulted in the elimination of the CNV-induced increase in C5a levels, while animals treated with the C5a-blocking antibody retained elevated C5a levels; but C5a is presumably bound to the antibody and thereby inactivated (FIG. 5).

FIG. 5 shows that animals injected with anti-C5 have lower ocular anti-C5a levels. ELISA measurements of RPE/choroid demonstrated an increase of C5a levels after induction of CNV (P≤0.001). This increase was eliminated in anti-C5-treated mice; whereas mice treated with anti-C5a and 12B4 control antibodies had control levels of ocular C5a. Data shown were average values (±SEM).

Both anti-C5 and anti-C5a had small but significant effects in reducing the CNV-triggered increase in splenic γδTR levels; whereas the CNV-triggered increase in RORγ levels was completely prevented in the treated mice (FIG. 6b). Moreover, inhibitor treatment completely prevented the rise of IL-17 and γδTR in the eyes of CNV mice (FIG. 6b); apparently C5a levels in the eye contribute to the recruitment of C5a-receptor-bearing T-cells.

FIG. 6 shows effects of C5a and C5 on T cells. Splenic (b) and ocular (a) samples were isolated 6 days after induction of CNV and analyzed by QRT-PCR using primers specific for Th-17 (RORγ) and γδT-cells (γδTR). (a) Following CNV, mice treated with anti-C5 and anti-C5a demonstrated a significant decrease in ocular levels of IL-17 and γδTR gene expression, whereas RORγ levels were unaltered. (b). Splenic levels of T-cell-specific genes in CNV mice indicated that RORγ levels returned to control levels in mice treated with anti-C5 and anti-C5a, whereas γδTR remained elevated.

IL-17 Promotes Inflammation in the Eye

Hasegawa and colleagues have recently shown that depletion of γδT-cells reduced IL-17 levels in the eye and ameliorated experimental CNV. The pro-angiogenic effect of IL-17 in RPE cells was confirmed by stimulating ARPE-19 cells grown as mature monolayers (Thurman, J. M. et al. *J Biol Chem* 284, 16939-16947, (2009)) and measuring gene expression for marker genes and barrier function.

Here, a greater than 40-fold increase in C3 gene expression in the eye as well as a ~10 fold increase in IL-17 in the eye was observed following IL-17 stimulation, whereas expression levels of VEGF and CFH mRNA were unaffected in the eye (FIG. 7a). Addition of 5 ng of IL-17A into the apical chamber of the monolayer resulted in a significant decrease in transepithelial resistance as measured using a volt-ohm meter (FIG. 7b).

FIG. 7 shows effect of IL-17 on RPE cells. (a) Change in gene expression following apical IL-17 exposure (5 ng/mL) was measured in mature ARPE-19 cell monolayers. C3 as well as IL-17 expression levels demonstrated an increase in fold change over the control, whereas VEGF and CFH were unaltered. (b) Transepithelial resistance measurements indicated a loss in barrier function in response to apical application of 5 ng/mL IL-17 after four hours.

CNV triggered an immune response in the spleen, presumably via the release of soluble retina or RPE proteins, and resulted in an increase in IL-17-producing γδT- and Th17-cells; yet despite this increase in systemic γδT- and Th17-cells, there is only evidence for γδT-cell migration into the CNV eye.

A blocking antibody to C5 or reducing C5a-signaling reduced CNV in the mouse eye, blunted the CNV-induced production of Th17- and γδT-cells in the spleen, and prevented the influx of γδT-cells into the CNV eyes.

Reduced IL-17 production in ICOS$^{-/-}$ mice resulted in significantly smaller CNV lesion and a lack of invasion of γδT cells into the CNV eyes; and application of exogenous IL-17 triggered a pro-inflammatory state in RPE cells, resulting in an increase in VEGF and C3 production.

Thus CNV lesions trigger a splenic immune response that augments ocular inflammation via the infiltration of IL-17-producing γδT-cells recruited to the eye by the locally generated chemoattractant C5a.

Neoepitopes for nAbs are present in CNV lesions and rag1$^{-/-}$ can be reconstituted with these specific nAbs for the augmentation of CNV size. Joseph, K. et al. *J Biol Chem*, doi:M112.421891 [pii]10.1074/jbc.M112.421891 (2013). A proliferative spleen response of T-lymphocytes to retina- and RPE-derived antigens was generated, it is plausible that additional effects on B-cells were generated.

IL-17 in AMD

IL-17 is a major proinflammatory cytokine that is linked to the pathogenesis of a number of different diseases including rheumatoid arthritis, uveitis and possibly AMD. Relevant for the development of AMD, which for the wet form involves an increase in VEGF production and secretion and endothelial cell growth and vessel formation, IL-17 has been shown in other systems to not only increase production of VEGF, but to induce angiogenesis, cell migration, and cell invasion using human dermal endothelial cells. In animal models relevant to AMD, IL-17 has been found to accumulate in the mouse eye during age-dependent degeneration as well as during CNV, and CNV progression can be reduced by interfering with IL-17 signaling. Finally, in AMD patients, increased serum levels of IL-17 have been reported as well as hypomethylation of the IL-17 receptor C. There are a number of different effector cells that produce IL-17; the IL-17-producing T-cell (Th17), γδT-cells, as well as innate lymphoid cells (ILCs). In the mouse models relevant to AMD, IL-17 in the eye is due to the infiltration of γδT-cells rather than Th17-cells.

It appears that γδT- rather than Th17-cells are the T-cells producing IL-17 in the eye in response to CNV, since the increase in IL-17 observed in the eyes of control animals correlated with an increase of the γδT-cell receptor, rather than the marker specific for Th17 cells (RORγ). Likewise, IL-17 apparently generates a pro-inflammatory environment in the RPE by affecting barrier function, increasing VEGF and complement production, overall generating a vicious cycle of inflammation and complement activation.

How to Link Complement and IL-17-C5a as a Chemoattractant

It is now accepted that an overactive complement system is tied to the incidence of AMD. There exists a high concentration of complement regulatory proteins and membrane attack complex (MAC) in the area of Bruch's membrane and RPE and membrane attack complex deposition density is correlated with AMD risk genotypes. It has been hypothesized that the alternative pathway of complement (AP) is critical to AMD pathogenesis. In addition, variations in the genes for CFB, C2, C3, CFHR1/3 as risk factors have also been reported; and an inverse relationship between AMD and SERPING1 (C1 inhibitor) exists. Finally, anaphylatoxin proteins C3a and C5a have been reported in pathological structures associated with AMD. Of the biological effector molecules produced during complement activation, only the anaphylatoxins have been shown to exhibit proangiogenic and chemotactic properties. C5a has been shown to promote IL-22 and IL-17 expression from CD4+ T-cells derived from AMD patients, and C5a has been shown to promote production of another cytokine, IL-8, as well as VEGF, by ARPE-19 cells. Regarding C5a's chemotactic properties, while T-cells have been shown to express C5a receptors, no data is available in the ocular space that supports the notion that T-cells indeed follow the C5a gradient to enter the eye in AMD or in models of AMD.

The data here suggests for the first time that the anaphylatoxin C5a that is generated in the eye in response to CNV is reduced in response to the C5 blocking antibody or in response to a reduction of complement activation. This elevated level of the anaphylatoxin C5a in the eye could mediate the recruitment of pro-inflammatory T-cells into the eye. However, additive effects of removing direct effects of C5a on RPE or choroidal endothelial cells together with the lack of recruitment of γδT-cells cannot be excluded. Importantly, RPE cells have been shown to produce various cytokines in response to C5a stimulation and C5a was shown to interfere with anti-immunogenic role of the RPE by suppressing the production of the immunosuppressive agent TGF and decreasing the RPE's ability to suppress immune cell proliferation.

Example 2

Eculizumab at 100 mg/ml or 30 mg/ml for Ophthalmology Primate Study in Cynomolgus Monkeys The major objectives are: Compare routes of administration: intravitreal (IVT) versus intravenous (IV); Determine Intravitreal dose; Determine serum and ocular tissue distribution as well vitreous T of eculizumab in relation to routes of administration; Measure Eculizumab C5 binding activity recovered from vitreous fluid at various time points post IVT administration. The data represent evaluation of 10 primates.

TABLE 2

Cynomolgus Monkey Study Design

| Group Number Identification | Route | Dose* (µg/eye) | Dose Volume (µL/eye) | Dose Conc. (mg/mL) | Euthanasia Day |
|---|---|---|---|---|---|
| ECULIZUMAB 100 MG/ML placebo | IVT | 0 | 50/eye | 0 | 22 |
| 500 ug/eye ECULIZUMAB 100 MG/ML | IVT | 500 | 50/eye | 10 | 22 |
| 500 ug/eye ECULIZUMAB 100 MG/ML OD*/ ECULIZUMAB 100 MG/ML placebo OS | IVT X 2 d 0 & d 22 | 500 OD/ 0 OS | 50/eye | 10 OD/ 0 OS | 60 (after 2nd IVT) |
| 1500 ug/eye ECULIZUMAB 100 MG/ML | IVT | 1500/eye OD/0 OS | 50/eye | 30 | 22 and 45 |
| 5000 ug/eye ECULIZUMAB 100 MG/ML | IVT | 5000/eye OD/0 OS | 50/eye | 100 | 45 |
| ECULIZUMAB 30 MG/ML placebo | IVT | 0 | 50/eye | 0 | 22 |
| 500 ug/eye ECULIZUMAB 30 MG/ML | IVT | 500 | 50/eye | 10 | 22 |
| 500 ug/eye ECULIZUMAB 30 MG/ML OD/ ECULIZUMAB 30 MG/ML placebo OS | IVT X 2 d 0 & d 22 | 500 OD/ 0 OS | 50/eye | 10 OD/ 0 OS | 60 (after 2nd IVT) |

TABLE 2-continued

Cynomolgus Monkey Study Design

| Group Number Identification | Route | Dose* (µg/eye) | Dose Volume (µL/eye) | Dose Conc. (mg/mL) | Euthanasia Day |
|---|---|---|---|---|---|
| 1500 ug/eye ECULIZUMAB 30 MG/ML | IVT | 1500/eye OD/0 OS | 50/eye | 30 | 45 |
| Single IV ECULIZUMAB 30 MG/ML | Intravenous | IV 20 mg/kg | 0.680 mL/kg | 29.4 | 22 |

*The OD and OS nomenclature refers to using one eye for drug administration and the other eye for placebo.

Nine ocular compartments were dissected: sclera/choroid, retina, optic nerve, vitreous body, lens, ciliary body, cornea, iris, and aqueous humor.

Figure 8A:
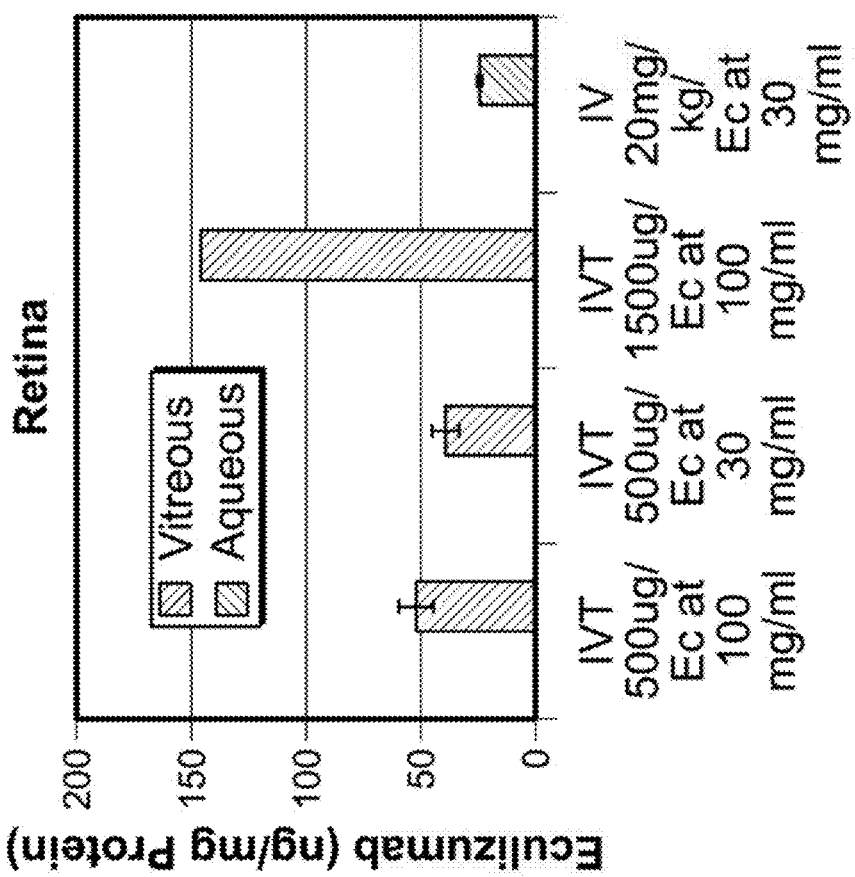

Intravitreal (IVT) administration resulted in higher eculizumab concentrations in retina and vitreous, aqueous than for IV Dosing of 20 mg/Kg of eculizumab. See FIG. 8.

Figure 9:
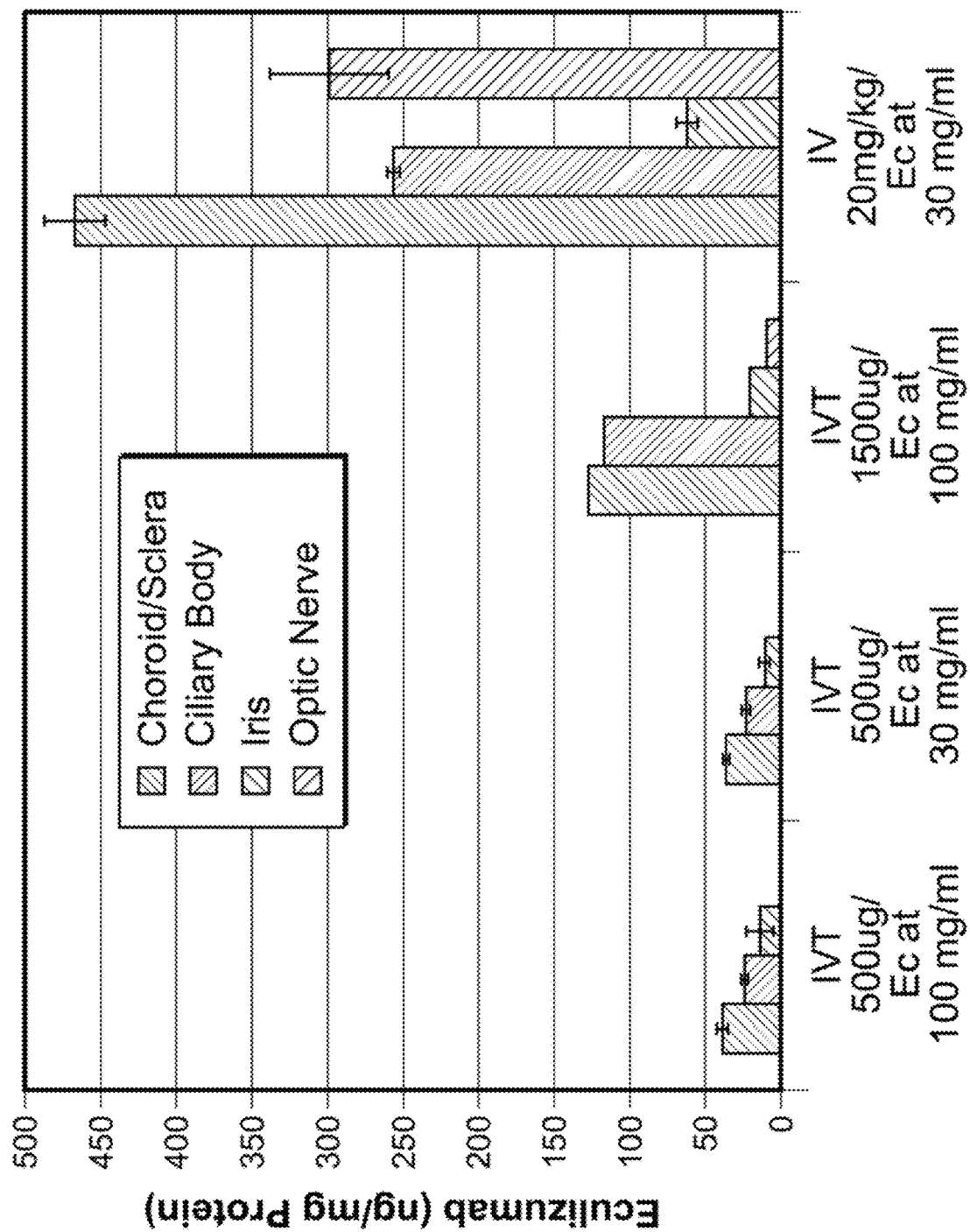
FIG. 9 shows that IV administration resulted in higher concentrations of eculizumab (Ec) than IVT in the vascularized eye compartments: choroid/sclera, optic nerve, ciliary body and iris.

IV administration resulted in higher concentrations of eculizumab than IVT in the vascularized eye compartments: choroid/sclera, optic Nerve, ciliary body and iris. See FIG. 9.

Figures 10A, 10B:
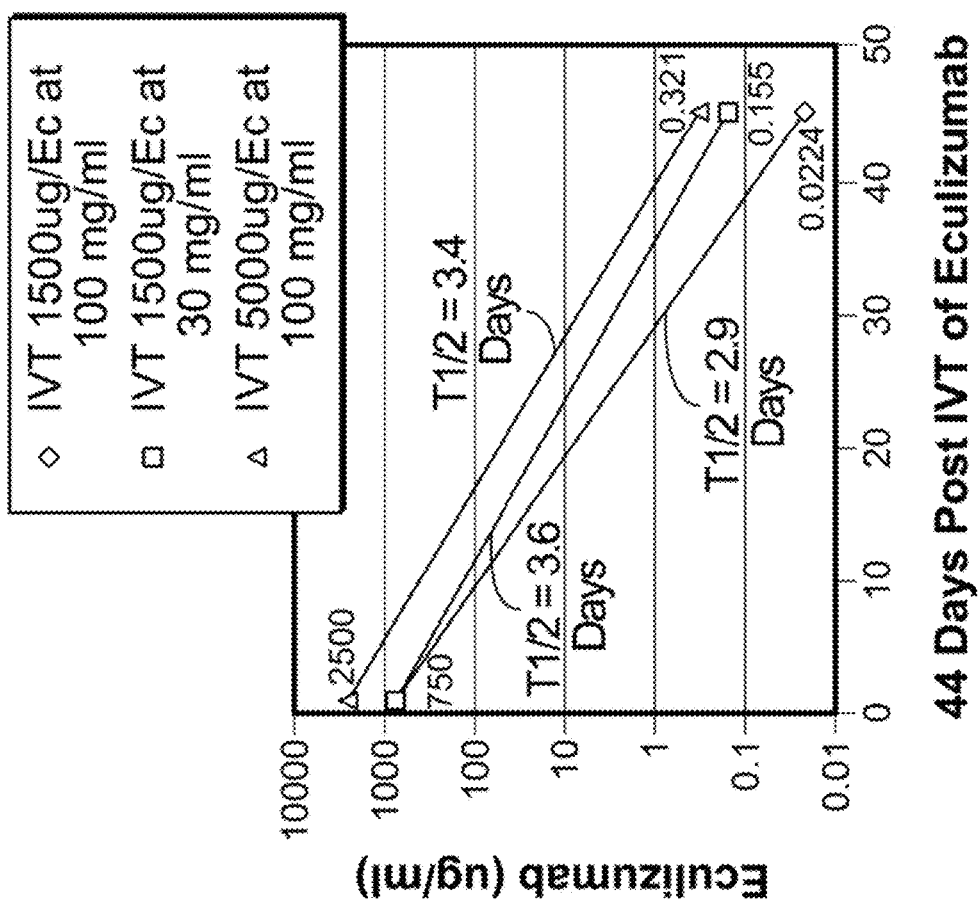
FIG. 10 shows that IVT administration of eculizumab (Ec) results in vitreous T1/2 ranging from 2.8 to 3.6 days.

IVT administration of eculizumab results in vitreous T1/2 ranging from 2.8 to 3.6 days. See FIG. 10.

Figure 11:
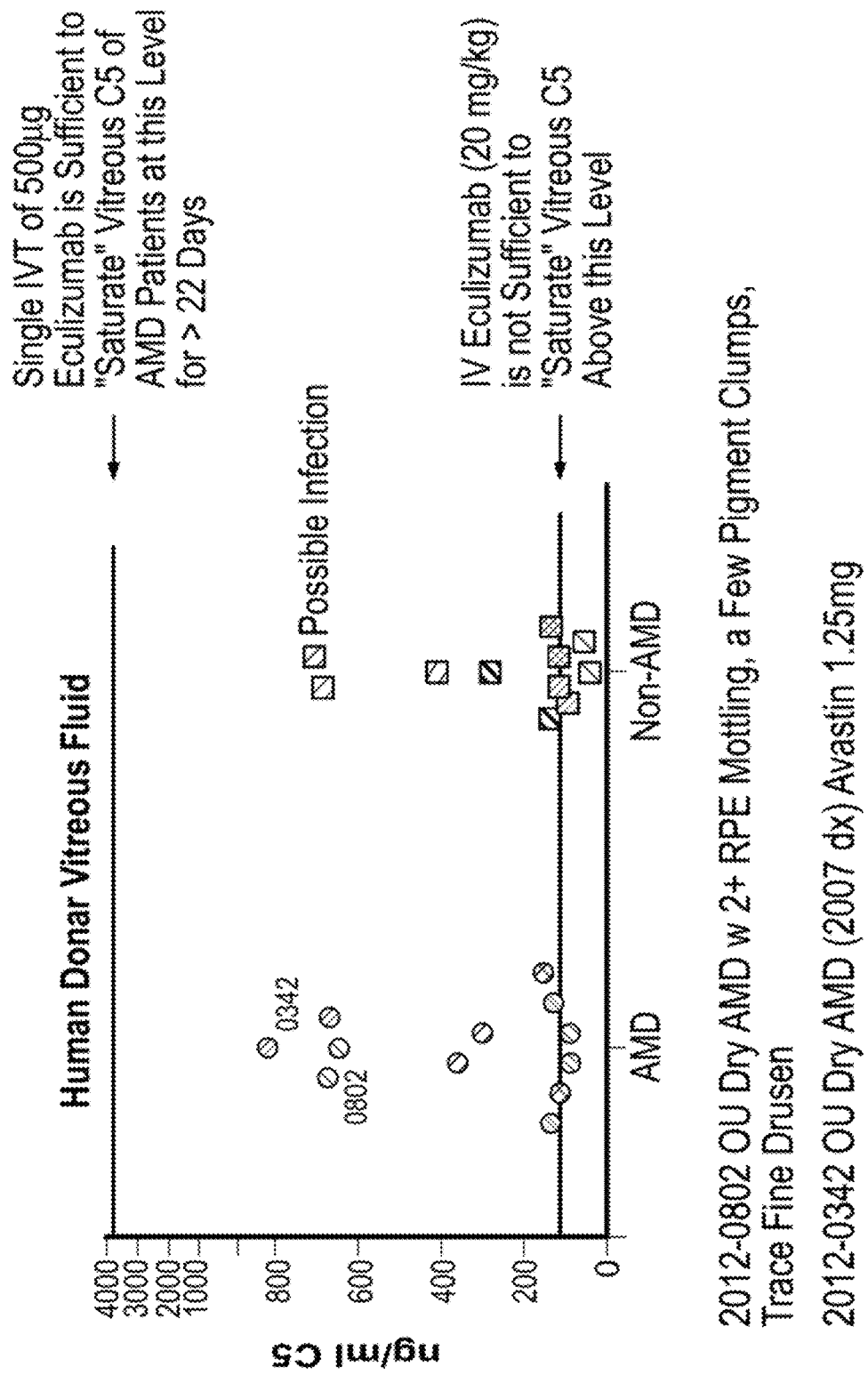
FIG. 11 shows that intravitreal but not IV administration of eculizumab is sufficient to saturate vitreous C5 in dry AMD patients.

Intravitreal but not IV administration of eculizumab is sufficient to saturate vitreous C5 in dry AMD patients. See FIG. 11.

Figure 12B:
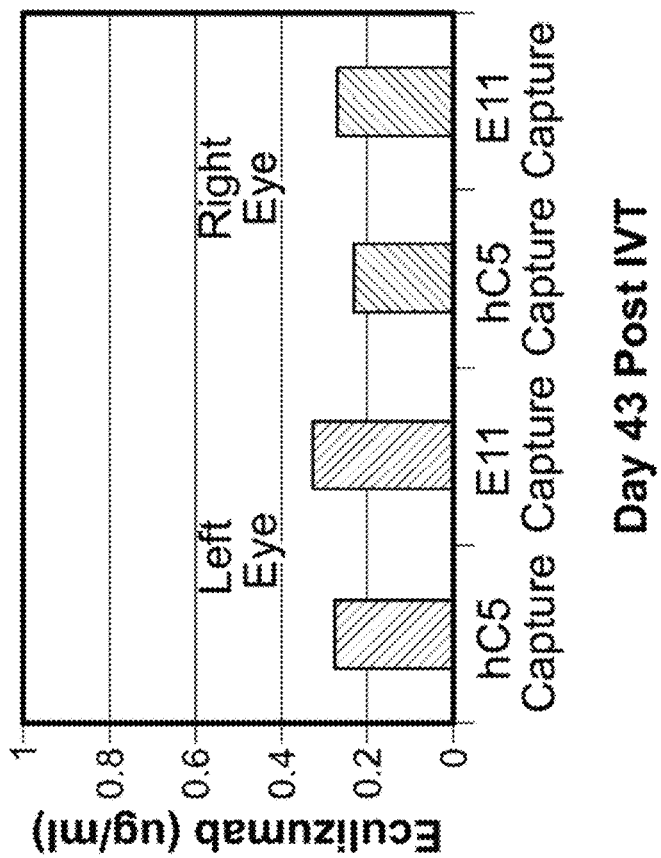
FIG. 12 shows that eculizumab maintains C5 binding activity in vitreous fluid more than 6 weeks post single IVT administration.
Figure 12A:
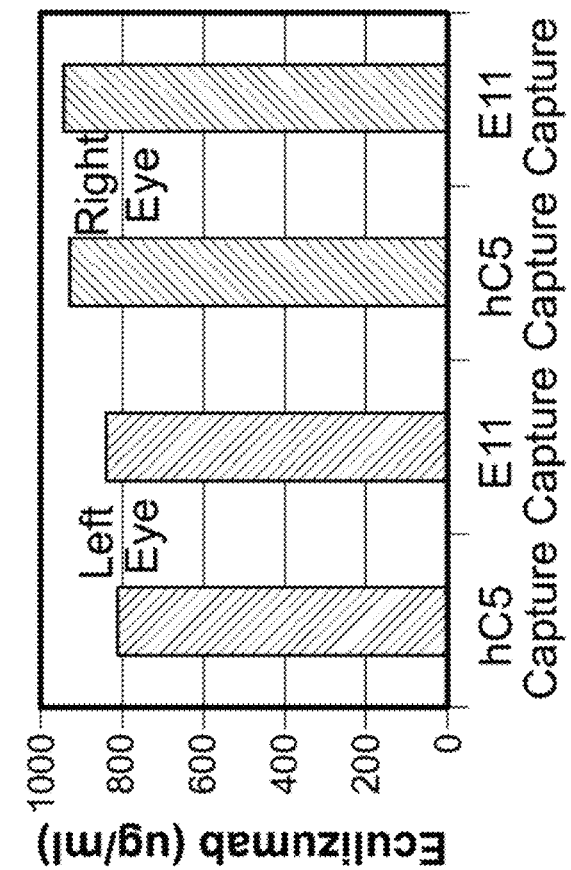

Eculizumab maintains C5 binding activity in vitreous fluid more than 6 weeks post single IVT administration. See FIG. 12.

Eculizumab (100 mg/ml or higher) for Ophthalmology Toxicology and PK Analysis in Cynomolgus Monkeys NHP (Cyno) Intravitreal and IV Tox/PK Study 570589 (Non-GLP)

Design: Single IVT Dose 0.5, 1.5, 5 mg/eye, two doses of 0.5 mg/eye at Day 1 and Day 22; single IV administration 20 mg/kg eculizumab.

Measured clinical signs, body weight, ophthalmology and ERG, gross necropsy.

Pharmacology

IVT administration resulted in higher eculizumab concentrations in retina, vitreous and aqueous fluid than IV administration. IVT administration of eculizumab resulted In vitreous T1/2 of 2.8 to 3.6 days. Eculizumab retains full human C5 (hC5) binding in vitreous fluid 43 days Post IVT administration. IV administration resulted in higher concentrations of eculizumab in the vascularized eye compartments: choroid/sclera, optic nerve, ciliary body and iris. Single IVT of 500 mg of eculizumab but not IV administration (of 20 mg/kg) eculizumab is sufficient to "saturate" vitreous C5 in dry AMD patients for more than 22 days. No antibodies against Eculizumab were detected in the serum of monkeys receiving 500 mg IVT doses X2.

Toxicology

Dose-related ocular findings—inflammatory: mild-moderate anterior chamber cells and cell-like opacities (0.2 and 0.5 mg); more prominent acute inflammation at 1.5 and 5.35 mg, including anterior chamber cells, flare and/or incomplete pupil dilation noted over the first week, tended to resolve over time (days 7-14). No other systemic effects or effects on ERGs. IVT administration of eculizumab at 100 mg/ml is well tolerated by cynomolgus monkeys.

NHP (Cyno) Intravitreal Tox/PK Study (Non-GLP)
Design
Single injection, 10 mg/eye
Measured clinical signs, body weight, ophthalmology and ERG, gross necropsy, histopathology
Pharmacology
IVT administration of eculizumab resulted in vitreous T1/2 of 2.97 days
Tox
Transient ocular inflammation, slight to moderate anterior uveitis, vitreal changes, vascular/perivascular inflammation in some animals. No systemic effects or effects on ERG.
Rabbit Intravitreal Tox/PK Study (Non-GLP)
Single IVT Dose, 0.2 1.5 or 5 mg/eye
High dose: slight uveitis on Day 3, progressing to severe by day 7. Animals euthanized for welfare reasons on day 13
Low and intermediate dose: uveitis, but less severe than high dose on Day 14
ADA present (all doses)

Example 3

Eculizumab scFv: Single Chain Anti-C5 mAb; Study of Ocular Topical Administration Rationale: Significant retinal scFv of eculizumab localization was observed following single topical administration as eye drops in rabbits.

Objective: To investigate if a scFv of eculizumab can reach the retina after topical administration in cynomolgus monkeys.

Study Design
Eculizumab scFv (44.5 mg/mL)
One drop per eye was administered every 30 minutes over a period of 5 hours for a total 10 administrations
Ocular tissues and serum were collected at 5 hours
Eculizumab scFv tissue concentration was measured by MSD ELISA assay

TABLE 3

Study Design (Cynomolgus Monkey)

| Group/Animal Number Identification | Dose Level (mg/eye)* | Dose Volume (µL/eye)* | Number of Animals | Sacrifice Time (hours post-dose) |
|---|---|---|---|---|
| 101 | 22 | 50 × 10 | 1 (male) | 5 hr |
| 151 | 22 | 50 × 10 | 1 (female) | 5 hr |

*50 µL drop was administered every 30 minutes over a period of 5 hours. (50 mL × 44.5 mg/ml × 10 = 22 mg/eye)

Figure 13:
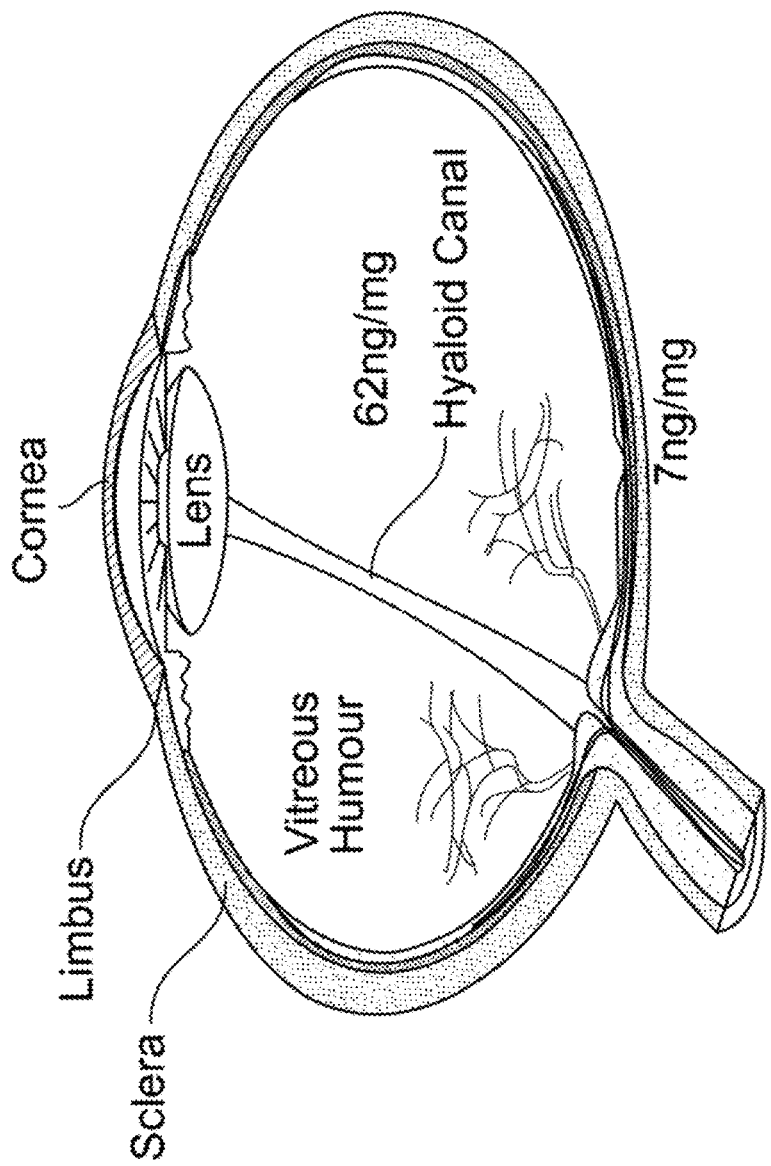
FIG. 13 shows eculizumab scFv tissue distribution following topical administration in cynomolgus monkeys, 5 hours after initial treatment. Note that eculizumab scFv multimerization in tissue may lead to underestimate of effective retinal concentration. Topically administered Eculizumab scFv can access the retina in NHPs. No corneal irritation was observed after topical administration of Eculizumab. Note that Serum: 0.12 ng/mg protein.

Eculizumab scFv tissue distribution following topical administration in cynomolgus monkeys is shown in FIG. 13, 5 hours after initial treatment. Note that eculizumab scFv multimerization in tissue may lead to underestimation of the effective retinal concentration. Topically administered Eculizumab scFv did access the retina in NHPs. No corneal irritation was observed after topical administration of Eculizumab and the serum concentration was 0.12 ng/mg protein.

Figures 14A, 14B, 14C:
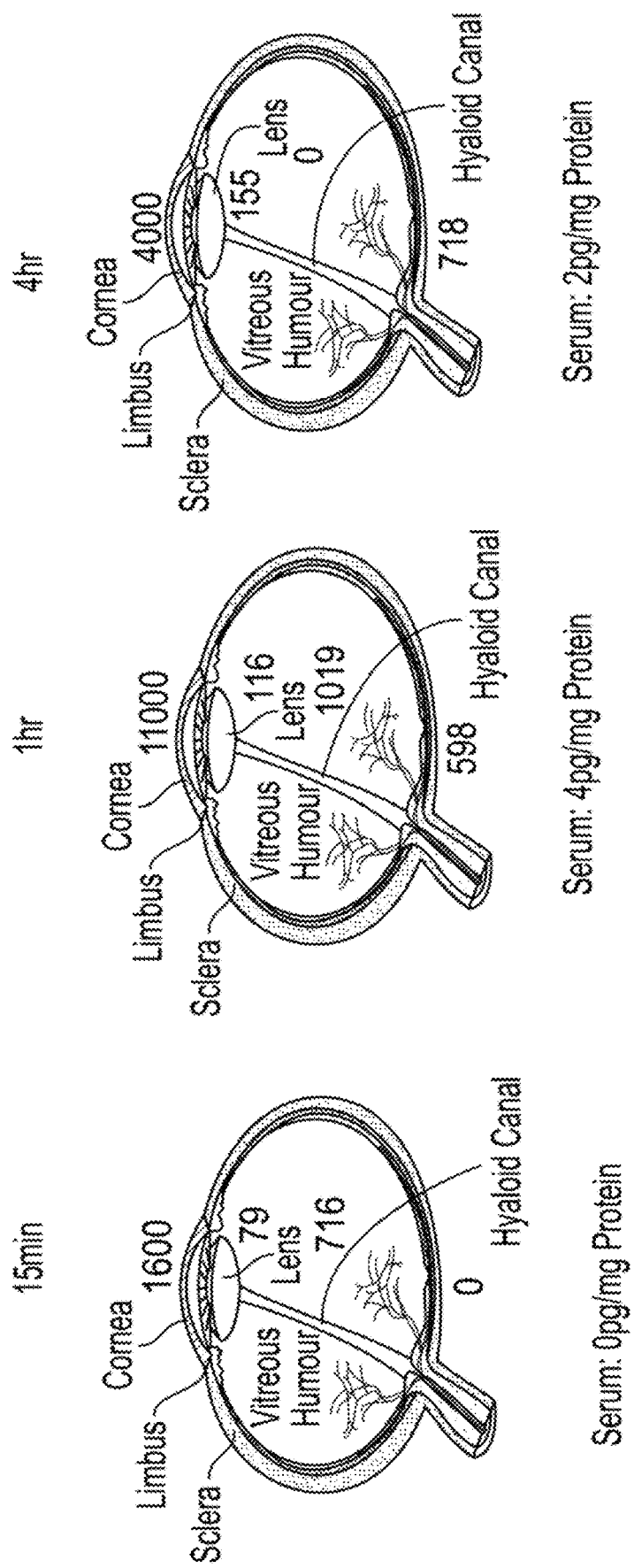
FIG. 14 shows estimated eculizumab scFv soluble multimer concentration after a single eye drop (pg/mg of protein).

Estimated eculizumab scFv soluble multimer Concentration after a single eye drop (pg/mg of protein). See FIG. 14.

Other Embodiments

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

TABLE 4

SOME NUCLEIC ACID AND AMINO ACID SEQUENCES

SEQ ID NO: 1

| | | | | | | | | | | | | | | | |
|---|---|---|---|---|---|---|---|---|---|---|---|---|---|---|---|
| gat | atc | cag | atg | acc | cag | tcc | ccg | tcc | tcc | ctg | tcc | gcc | tct | gtg | ggc | 48 |
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| gat | agg | gtc | acc | atc | acc | tgc | ggc | gcc | agc | gaa | aac | atc | tat | ggc | gcg | 96 |
| Asp | Arg | Val | Thr | Ile | Thr | Cys | Gly | Ala | Ser | Glu | Asn | Ile | Tyr | Gly | Ala |
| | | | 20 | | | | | 25 | | | | | 30 | | |
| ctg | aac | tgg | tat | caa | cag | aaa | ccc | ggg | aaa | gct | ccg | aag | ctt | ctg | att | 144 |
| Leu | Asn | Trp | Tyr | Gln | Gln | Lys | Pro | Gly | Lys | Ala | Pro | Lys | Leu | Leu | Ile |
| | | | 35 | | | | 40 | | | | | 45 | | | |
| tac | ggt | gcg | acg | aac | ctg | gca | gat | gga | gtc | cct | tct | cgc | ttc | tct | gga | 192 |
| Tyr | Gly | Ala | Thr | Asn | Leu | Ala | Asp | Gly | Val | Pro | Ser | Arg | Phe | Ser | Gly |
| | 50 | | | | | 55 | | | | | 60 | | | | |
| tcc | ggc | tcc | gga | acg | gat | ttc | act | ctg | acc | atc | agc | agt | ctg | cag | cct | 240 |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| gaa | gac | ttc | gct | acg | tat | tac | tgt | cag | aac | gtt | tta | aat | act | ccg | ttg | 288 |
| Glu | Asp | Phe | Ala | Thr | Tyr | Tyr | Cys | Gln | Asn | Val | Leu | Asn | Thr | Pro | Leu |
| | | | | 85 | | | | | 90 | | | | | 95 | |
| act | ttc | gga | cag | ggt | acc | aag | gtg | gaa | ata | aaa | cgt | act | ggc | ggt | ggt | 336 |
| Thr | Phe | Gly | Gln | Gly | Thr | Lys | Val | Glu | Ile | Lys | Arg | Thr | Gly | Gly | Gly |
| | | | 100 | | | | | 105 | | | | | 110 | | |
| ggt | tct | ggt | ggc | ggt | gga | tct | ggt | ggt | ggc | ggt | tct | caa | gtc | caa | ctg | 384 |
| Gly | Ser | Gly | Gly | Gly | Gly | Ser | Gly | Gly | Gly | Gly | Ser | Gln | Val | Gln | Leu |
| | | 115 | | | | | 120 | | | | | 125 | | | |
| gtg | caa | tcc | ggc | gcc | gag | gtc | aag | aag | cca | ggg | gcc | tca | gtc | aaa | gtg | 432 |
| Val | Gln | Ser | Gly | Ala | Glu | Val | Lys | Lys | Pro | Gly | Ala | Ser | Val | Lys | Val |
| | 130 | | | | | 135 | | | | | 140 | | | | |
| tcc | tgt | aaa | gct | agc | ggc | tat | att | ttt | tct | aat | tat | tgg | att | caa | tgg | 480 |
| Ser | Cys | Lys | Ala | Ser | Gly | Tyr | Ile | Phe | Ser | Asn | Tyr | Trp | Ile | Gln | Trp |
| 145 | | | | | 150 | | | | | 155 | | | | | 160 |
| gtg | cgt | cag | gcc | ccc | ggg | cag | ggc | ctg | gaa | tgg | atg | ggt | gag | atc | tta | 528 |
| Val | Arg | Gln | Ala | Pro | Gly | Gln | Gly | Leu | Glu | Trp | Met | Gly | Glu | Ile | Leu |
| | | | | 165 | | | | | 170 | | | | | 175 | |
| ccg | ggc | tct | ggt | agc | acc | gaa | tat | acc | gaa | aat | ttt | aaa | gac | cgt | gtt | 576 |
| Pro | Gly | Ser | Gly | Ser | Thr | Glu | Tyr | Thr | Glu | Asn | Phe | Lys | Asp | Arg | Val |
| | | | 180 | | | | | 185 | | | | | 190 | | |
| act | atg | acg | cgt | gac | act | tcg | act | agt | aca | gta | tac | atg | gag | ctc | tcc | 624 |
| Thr | Met | Thr | Arg | Asp | Thr | Ser | Thr | Ser | Thr | Val | Tyr | Met | Glu | Leu | Ser |
| | | 195 | | | | | 200 | | | | | 205 | | | |
| agc | ctg | cga | tcg | gag | gac | acg | gcc | gtc | tat | tat | tgc | gcg | cgt | tat | ttt | 672 |
| Ser | Leu | Arg | Ser | Glu | Asp | Thr | Ala | Val | Tyr | Tyr | Cys | Ala | Arg | Tyr | Phe |
| | 210 | | | | | 215 | | | | | 220 | | | | |
| ttt | ggt | tct | agc | ccg | aat | tgg | tat | ttt | gat | gtt | tgg | ggt | caa | gga | acc | 720 |
| Phe | Gly | Ser | Ser | Pro | Asn | Trp | Tyr | Phe | Asp | Val | Trp | Gly | Gln | Gly | Thr |
| 225 | | | | | 230 | | | | | 235 | | | | | 240 |
| ctg | gtc | act | gtc | tcg | agc | tga | | | | | | | | | |

TABLE 4-continued

SOME NUCLEIC ACID AND AMINO ACID SEQUENCES

741
Leu Val Thr Val Ser Ser
            245

SEQ ID NO: 2
Asp Ile Gln Met Thr Gln Ser Pro Ser Ser Leu Ser Ala Ser Val Gly
1               5                   10                  15
Asp Arg Val Thr Ile Thr Cys Gly Ala Ser Glu Asn Ile Tyr Gly Ala
            20                  25                  30
Leu Asn Trp Tyr Gln Gln Lys Pro Gly Lys Ala Pro Lys Leu Leu Ile
        35                  40                  45
Tyr Gly Ala Thr Asn Leu Ala Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Asn Val Leu Asn Thr Pro Leu
                85                  90                  95
Thr Phe Gly Gln Gly Thr Lys Val Glu Ile Lys Arg Thr Gly Gly Gly
            100                 105                 110
Gly Ser Gly Gly Gly Gly Ser Gly Gly Gly Gly Ser Gln Val Gln Leu
        115                 120                 125
Val Gln Ser Gly Ala Glu Val Lys Lys Pro Gly Ala Ser Val Lys Val
    130                 135                 140
Ser Cys Lys Ala Ser Gly Tyr Ile Phe Ser Asn Tyr Trp Ile Gln Trp
145                 150                 155                 160
Val Arg Gln Ala Pro Gly Gln Gly Leu Glu Trp Met Gly Glu Ile Leu
                165                 170                 175
Pro Gly Ser Gly Ser Thr Glu Tyr Thr Glu Asn Phe Lys Asp Arg Val
            180                 185                 190
Thr Met Thr Arg Asp Thr Ser Thr Ser Thr Val Tyr Met Glu Leu Ser
        195                 200                 205
Ser Leu Arg Ser Glu Asp Thr Ala Val Tyr Tyr Cys Ala Arg Tyr Phe
    210                 215                 220
Phe Gly Ser Ser Pro Asn Trp Tyr Phe Asp Val Trp Gly Gln Gly Thr
225                 230                 235                 240
Leu Val Thr Val Ser Ser
            245

SEQ ID NO: 3
Gly Gly Gly Gly Ser Gly Gly Gly Gly Ser Gly Gly Gly Gly Ser

SEQ ID NO: 4
Met Gly Leu Leu Gly Ile Leu Cys Phe Leu Ile Phe Leu Gly Lys Thr
1               5                   10                  15
Trp Gly Gln Glu Gln Thr Tyr Val Ile Ser Ala Pro Lys Ile Phe Arg
            20                  25                  30
Val Gly Ala Ser Glu Asn Ile Val Ile Gln Val Tyr Gly Tyr Thr Glu
        35                  40                  45
Ala Phe Asp Ala Thr Ile Ser Ile Lys Ser Tyr Pro Asp Lys Lys Phe
    50                  55                  60
Ser Tyr Ser Ser Gly His Val His Leu Ser Ser Glu Asn Lys Phe Gln
65                  70                  75                  80
Asn Ser Ala Ile Leu Thr Ile Gln Pro Lys Gln Leu Pro Gly Gly Gln
                85                  90                  95
Asn Pro Val Ser Tyr Val Tyr Leu Glu Val Val Ser Lys His Phe Ser
            100                 105                 110
Lys Ser Lys Arg Met Pro Ile Thr Tyr Asp Asn Gly Phe Leu Phe Ile
        115                 120                 125
His Thr Asp Lys Pro Val Tyr Thr Pro Asp Gln Ser Val Lys Val Arg
    130                 135                 140
Val Tyr Ser Leu Asn Asp Asp Leu Lys Pro Ala Lys Arg Glu Thr Val
145                 150                 155                 160
Leu Thr Phe Ile Asp Pro Glu Gly Ser Glu Val Asp Met Val Glu Glu
                165                 170                 175
Ile Asp His Ile Gly Ile Ile Ser Phe Pro Asp Phe Lys Ile Pro Ser
            180                 185                 190
Asn Pro Arg Tyr Gly Met Trp Thr Ile Lys Ala Lys Tyr Lys Glu Asp
        195                 200                 205
Phe Ser Thr Thr Gly Thr Ala Tyr Phe Glu Val Lys Glu Tyr Val Leu
    210                 215                 220
Pro His Phe Ser Val Ser Ile Glu Pro Glu Tyr Asn Phe Ile Gly Tyr
225                 230                 235                 240
Lys Asn Phe Lys Asn Phe Glu Ile Thr Ile Lys Ala Arg Tyr Phe Tyr
                245                 250                 255
Asn Lys Val Val Thr Glu Ala Asp Val Tyr Ile Thr Phe Gly Ile Arg
            260                 265                 270
Glu Asp Leu Lys Asp Asp Gln Lys Glu Met Met Gln Thr Ala Met Gln
        275                 280                 285

TABLE 4-continued

SOME NUCLEIC ACID AND AMINO ACID SEQUENCES

Asn Thr Met Leu Ile Asn Gly Ile Ala Gln Val Thr Phe Asp Ser Glu
    290                 295                 300
Thr Ala Val Lys Glu Leu Ser Tyr Tyr Ser Leu Glu Asp Leu Asn Asn
305                 310                 315                 320
Lys Tyr Leu Tyr Ile Ala Val Thr Val Ile Glu Ser Thr Gly Gly Phe
                325                 330                 335
Ser Glu Glu Ala Glu Ile Pro Gly Ile Lys Tyr Val Leu Ser Pro Tyr
            340                 345                 350
Lys Leu Asn Leu Val Ala Thr Pro Leu Phe Leu Lys Pro Gly Ile Pro
        355                 360                 365
Tyr Pro Ile Lys Val Gln Val Lys Asp Ser Leu Asp Gln Leu Val Gly
    370                 375                 380
Gly Val Pro Val Ile Leu Asn Ala Gln Thr Ile Asp Val Asn Gln Glu
385                 390                 395                 400
Thr Ser Asp Leu Asp Pro Ser Lys Ser Val Thr Arg Val Asp Asp Gly
                405                 410                 415
Val Ala Ser Phe Val Leu Asn Leu Pro Ser Gly Val Thr Val Leu Glu
            420                 425                 430
Phe Asn Val Lys Thr Asp Ala Pro Asp Leu Pro Glu Glu Asn Gln Ala
        435                 440                 445
Arg Glu Gly Tyr Arg Ala Ile Ala Tyr Ser Ser Leu Ser Gln Ser Tyr
    450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
                485                 490                 495
Thr His Tyr Asn Tyr Leu Ile Leu Ser Lys Gly Lys Ile Ile His Phe
            500                 505                 510
Gly Thr Arg Glu Lys Phe Ser Asp Ala Ser Tyr Gln Ser Ile Asn Ile
        515                 520                 525
Pro Val Thr Gln Asn Met Val Pro Ser Ser Arg Leu Leu Val Tyr Tyr
    530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
                565                 570                 575
Pro Asp Ala Asp Ala Tyr Ser Pro Gly Gln Thr Val Ser Leu Asn Met
            580                 585                 590
Ala Thr Gly Met Asp Ser Trp Val Ala Leu Ala Ala Val Asp Ser Ala
        595                 600                 605
Val Tyr Gly Val Gln Arg Gly Ala Lys Lys Pro Leu Glu Arg Val Phe
    610                 615                 620
Gln Phe Leu Glu Lys Ser Asp Leu Gly Cys Gly Ala Gly Gly Gly Leu
625                 630                 635                 640
Asn Asn Ala Asn Val Phe His Leu Ala Gly Leu Thr Phe Leu Thr Asn
                645                 650                 655
Ala Asn Ala Asp Asp Ser Gln Glu Asn Asp Glu Pro Cys Lys Glu Ile
            660                 665                 670
Leu Arg Pro Arg Arg Thr Leu Gln Lys Lys Ile Glu Glu Ile Ala Ala
        675                 680                 685
Lys Tyr Lys His Ser Val Val Lys Lys Cys Cys Tyr Asp Gly Ala Cys
    690                 695                 700
Val Asn Asn Asp Glu Thr Cys Glu Gln Arg Ala Ala Arg Ile Ser Leu
705                 710                 715                 720
Gly Pro Arg Cys Ile Lys Ala Phe Thr Glu Cys Cys Val Val Ala Ser
                725                 730                 735
Gln Leu Arg Ala Asn Ile Ser His Lys Asp Met Gln Leu Gly Arg Leu
            740                 745                 750
His Met Lys Thr Leu Leu Pro Val Ser Lys Pro Glu Ile Arg Ser Tyr
        755                 760                 765
Phe Pro Glu Ser Trp Leu Trp Glu Val His Leu Val Pro Arg Arg Lys
    770                 775                 780
Gln Leu Gln Phe Ala Leu Pro Asp Ser Leu Thr Thr Trp Glu Ile Gln
785                 790                 795                 800
Gly Ile Gly Ile Ser Asn Thr Gly Ile Cys Val Ala Asp Thr Val Lys
                805                 810                 815
Ala Lys Val Phe Lys Asp Val Phe Leu Glu Met Asn Ile Pro Tyr Ser
            820                 825                 830
Val Val Arg Gly Glu Gln Ile Gln Leu Lys Gly Thr Val Tyr Asn Tyr
        835                 840                 845
Arg Thr Ser Gly Met Gln Phe Cys Val Lys Met Ser Ala Val Glu Gly
    850                 855                 860
Ile Cys Thr Ser Glu Ser Pro Val Ile Asp His Gln Gly Thr Lys Ser
865                 870                 875                 880
Ser Lys Cys Val Arg Gln Lys Val Glu Gly Ser Ser His Leu Val
                885                 890                 895
Thr Phe Thr Val Leu Pro Leu Glu Ile Gly Leu His Asn Ile Asn Phe
            900                 905                 910

TABLE 4-continued

| SOME NUCLEIC ACID AND AMINO ACID SEQUENCES |
|---|

```
Ser Leu Glu Thr Trp Phe Gly Lys Glu Ile Leu Val Lys Thr Leu Arg
        915                 920                 925
Val Val Pro Glu Gly Val Lys Arg Glu Ser Tyr Ser Gly Val Thr Leu
    930                 935                 940
Asp Pro Arg Gly Ile Tyr Gly Thr Ile Ser Arg Arg Lys Glu Phe Pro
945                 950                 955                 960
Tyr Arg Ile Pro Leu Asp Leu Val Pro Lys Thr Glu Ile Lys Arg Ile
                965                 970                 975
Leu Ser Val Lys Gly Leu Leu Val Gly Glu Ile Leu Ser Ala Val Leu
            980                 985                 990
Ser Gln Glu Gly Ile Asn Ile Leu Thr His Leu Pro Lys Gly Ser Ala
        995                 1000                1005
Glu Ala  Glu Leu Met Ser Val  Val Pro Val Phe Tyr  Val Phe His
    1010                 1015                 1020
Tyr Leu  Glu Thr Gly Asn His  Trp Asn Ile Phe His  Ser Asp Pro
    1025                 1030                 1035
Leu Ile  Glu Lys Gln Lys Leu  Lys Lys Lys Leu Lys  Glu Gly Met
    1040                 1045                 1050
Leu Ser  Ile Met Ser Tyr Arg  Asn Ala Asp Tyr Ser  Tyr Ser Val
    1055                 1060                 1065
Trp Lys  Gly Gly Ser Ala Ser  Thr Trp Leu Thr Ala  Phe Ala Leu
    1070                 1075                 1080
Arg Val  Leu Gly Gln Val Asn  Lys Tyr Val Glu Gln  Asn Gln Asn
    1085                 1090 1095
Ser Ile  Cys Asn Ser Leu Leu  Trp Leu Val Glu Asn  Tyr Gln Leu
    1100                 1105                 1110
Asp Asn  Gly Ser Phe Lys Glu  Asn Ser Gln Tyr Gln  Pro Ile Lys
    1115                 1120                 1125
Leu Gln  Gly Thr Leu Pro Val  Glu Ala Arg Glu Asn  Ser Leu Tyr
    1130                 1135                 1140
Leu Thr  Ala Phe Thr Val Ile  Gly Ile Arg Lys Ala  Phe Asp Ile
    1145                 1150                 1155
Cys Pro  Leu Val Lys Ile Asp  Thr Ala Leu Ile Lys  Ala Asp Asn
    1160                 1165                 1170
Phe Leu  Leu Glu Asn Thr Leu  Pro Ala Gln Ser Thr  Phe Thr Leu
    1175                 1180                 1185
Ala Ile  Ser Ala Tyr Ala Leu  Ser Leu Gly Asp Lys  Thr His Pro
    1190                 1195                 1200
Gln Phe  Arg Ser Ile Val Ser  Ala Leu Lys Arg Glu  Ala Leu Val
    1205                 1210                 1215
Lys Gly  Asn Pro Pro Ile Tyr  Arg Phe Trp Lys Asp  Asn Leu Gln
    1220                 1225                 1230
His Lys  Asp Ser Ser Val Pro  Asn Thr Gly Thr Ala  Arg Met Val
    1235                 1240                 1245
Glu Thr  Thr Ala Tyr Ala Leu  Leu Thr Ser Leu Asn  Leu Lys Asp
    1250                 1255                 1260
Ile Asn  Tyr Val Asn Pro Val  Ile Lys Trp Leu Ser  Glu Glu Gln
    1265                 1270                 1275
Arg Tyr  Gly Gly Gly Phe Tyr  Ser Thr Gln Asp Thr  Ile Asn Ala
    1280                 1285                 1290
Ile Glu  Gly Leu Thr Glu Tyr  Ser Leu Leu Val Lys  Gln Leu Arg
    1295                 1300                 1305
Leu Ser  Met Asp Ile Asp Val  Ser Tyr Lys His Lys  Gly Ala Leu
    1310                 1315                 1320
His Asn  Tyr Lys Met Thr Asp  Lys Asn Phe Leu Gly  Arg Pro Val
    1325                 1330                 1335
Glu Val  Leu Leu Asn Asp Asp  Leu Ile Val Ser Thr  Gly Phe Gly
    1340                 1345                 1350
Ser Gly  Leu Ala Thr Val His  Val Thr Thr Val Val  His Lys Thr
    1355                 1360                 1365
Ser Thr  Ser Glu Glu Val Cys  Ser Phe Tyr Leu Lys  Ile Asp Thr
    1370                 1375                 1380
Gln Asp  Ile Glu Ala Ser His  Tyr Arg Gly Tyr Gly  Asn Ser Asp
    1385                 1390                 1395
Tyr Lys  Arg Ile Val Ala Cys  Ala Ser Tyr Lys Pro  Ser Arg Glu
    1400                 1405                 1410
Glu Ser  Ser Ser Gly Ser Ser  His Ala Val Met Asp  Ile Ser Leu
    1415                 1420                 1425
Pro Thr  Gly Ile Ser Ala Asn  Glu Glu Asp Leu Lys  Ala Leu Val
    1430                 1435                 1440
Glu Gly  Val Asp Gln Leu Phe  Thr Asp Tyr Gln Ile  Lys Asp Gly
    1445                 1450                 1455
His Val  Ile Leu Gln Leu Asn  Ser Ile Pro Ser Ser  Asp Phe Leu
    1460                 1465                 1470
Cys Val  Arg Phe Arg Ile Phe  Glu Leu Phe Glu Val  Gly Phe Leu
    1475                 1480                 1485
Ser Pro  Ala Thr Phe Thr Val  Tyr Glu Tyr His Arg  Pro Asp Lys
    1490                 1495                 1500
```

TABLE 4-continued

SOME NUCLEIC ACID AND AMINO ACID SEQUENCES

| Gln | Cys | Thr | Met | Phe | Tyr | Ser | Thr | Ser | Asn | Ile | Lys | Ile | Gln | Lys |
|---|---|---|---|---|---|---|---|---|---|---|---|---|---|---|
| 1505 | | | | | 1510 | | | | | 1515 | | | | |
| Val | Cys | Glu | Gly | Ala | Ala | Cys | Lys | Cys | Val | Glu | Ala | Asp | Cys | Gly |
| 1520 | | | | | 1525 | | | | | 1530 | | | | |
| Gln | Met | Gln | Glu | Glu | Leu | Asp | Leu | Thr | Ile | Ser | Ala | Glu | Thr | Arg |
| 1535 | | | | | 1540 | | | | | 1545 | | | | |
| Lys | Gln | Thr | Ala | Cys | Lys | Pro | Glu | Ile | Ala | Tyr | Ala | Tyr | Lys | Val |
| 1550 | | | | | 1555 | | | | | 1560 | | | | |
| Ser | Ile | Thr | Ser | Ile | Thr | Val | Glu | Asn | Val | Phe | Val | Lys | Tyr | Lys |
| 1565 | | | | | 1570 | | | | | 1575 | | | | |
| Ala | Thr | Leu | Leu | Asp | Ile | Tyr | Lys | Thr | Gly | Glu | Ala | Val | Ala | Glu |
| 1580 | | | | | 1585 | | | | | 1590 | | | | |
| Lys | Asp | Ser | Glu | Ile | Thr | Phe | Ile | Lys | Lys | Val | Thr | Cys | Thr | Asn |
| 1595 | | | | | 1600 | | | | | 1605 | | | | |
| Ala | Glu | Leu | Val | Lys | Gly | Arg | Gln | Tyr | Leu | Ile | Met | Gly | Lys | Glu |
| 1610 | | | | | 1615 | | | | | 1620 | | | | |
| Ala | Leu | Gln | Ile | Lys | Tyr | Asn | Phe | Ser | Phe | Arg | Tyr | Ile | Tyr | Pro |
| 1625 | | | | | 1630 | | | | | 1635 | | | | |
| Leu | Asp | Ser | Leu | Thr | Trp | Ile | Glu | Tyr | Trp | Pro | Arg | Asp | Thr | Thr |
| 1640 | | | | | 1645 | | | | | 1650 | | | | |
| Cys | Ser | Ser | Cys | Gln | Ala | Phe | Leu | Ala | Asn | Leu | Asp | Glu | Phe | Ala |
| 1655 | | | | | 1660 | | | | | 1665 | | | | |
| Glu | Asp | Ile | Phe | Leu | Asn | Gly | Cys | | | | | | | |
| 1670 | | | | | 1675 | | | | | | | | | |

SEQ ID NO: 5
QVQLVQSGAEVKKPGASVKVSCKASGYIFSNYWIQWVRQAPGQGLEWMGEILPGSGSTEYTEN
FKDRVTMTRDTSTSTVYMELSSLRSEDTAVYYCARYFFGSSPNWYFDVWGQGTLVTVSSASTK
GPSVFPLAPCSRSTSESTAALGCLVKDYFPEPVTVSWNSGALTSGVHTFPAVLQSSGLYSLSS
VVTVPSSNFGTQTYTCNVDHKPSNTKVDKTVERKCCVECPPCPAPPVAGPSVFLFPPKPKDTL
MISRTPEVTCVVVDVSQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVFSCSVMHEALHNHYTQKS
LSLSLGK

SEQ ID NO: 6
DIQMTQSPSSLSASVGDRVTITCGASENIYGALNWYQQKPGKAPKLLIYGATNLADGVPSRFS
GSGSGTDFTLTISSLQPEDFATYYCQNVLNTPLTFGQGTKVEIKRTVAAPSVFIFPPSDEQLK
SGTASVVCLLNNFYPREAKVQWKVDNALQSGNSQESVTEQDSKDSTYSLSSTLTLSKADYEKH
KVYACEVTHQGLSSPVTKSFNRGEC

SEQ ID NO: 7
heavy chain (g2/4) (488 amino acids)
QVQLVQSGAEVKKPGASVKVSCKASGHIFSNYWIQWVRQAPGQGLEWMGEILPGSGHTEYTEN
FKDRVTMTRDTSTSTVYMELSSLRSEDTAVYYCARYFFGSSPNWYFDVWGQGTLVTVSSASTK
GPSVFPLAPCSRSTSESTAALGCLVKDYFPEPVTVSWNSGALTSGVHTFPAVLQSSGLYSLSS
VVTVPSSNFGTQTYTCNVDHKPSNTKVDKTVERKCCVECPPCPAPPVAGPSVFLFPPKPKDTL
MISRTPEVTCVVVDVSQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVFSCSVLHEALHSHYTQKS
LSLSLGK SEQ ID NO: 8
light chain: (Kappa) (214 amino acids)
DIQMTQSPSSLSASVGDRVTITCGASENIYGALNWYQQKPGKAPKLLIYGATNLADGVPSRFS
GSGSGTDFTLTISSLQPEDFATYYCQNVLNTPLTFGQGTKVEIKRTVAAPSVFIFPPSDEQLK
SGTASVVCLLNNFYPREAKVQWKVDNALQSGNSQESVTEQDSKDSTYSLSSTLTLSKADYEKH
KVYACEVTHQGLSSPVTKSFNRGEC

SEQ ID NO: 9
GYIFSNYWIQ

SEQ ID NO: 10
EILPGSGSTEYTENFKD

SEQ ID NO: 11
YFFGSSPNWYFDV

SEQ ID NO: 12
GASENIYGALN

SEQ ID NO: 13
GATNLAD

SEQ ID NO: 14
QNVLNTPLT

SEQ ID NO: 15

TABLE 4-continued

SOME NUCLEIC ACID AND AMINO ACID SEQUENCES

QVQLVQSGAEVKKPGASVKVSCKASGYIFSNYWIQWVRQAPGQGLEWMGEILPGSGSTEYTEN
FKDRVTMTRDTSTSTVYMELSSLRSEDTAVYYCARYFFGSSPNWYFDVWGQGTLVTVSS

SEQ ID NO: 16
DIQMTQSPSSLSASVGDRVTITCGASENIYGALNWYQQKPGKAPKLLIYGATNLADGVPSRFS
GSGSGTDFTLTISSLQPEDFATYYCQNVLNTPLTFGQGTKVEIK

SEQ ID NO: 47 Anti-human-C5a light chain
DIQMTQSPSS LSASVGDRVT ITCRASESVD SYGNSFMHWY QQKPGKAPKL
LIYRASNLES GVPSRFSGSG SGTDFTLTIS SLQPEDFATY YCQQSNEDPY
TFGGGTKVEI KRTVAAPSVF IFPPSDEQLK SGTASVVCLL NNFYPREAKV
QWKVDNALQS GNSQESVTEQ DSKDSTYSLS STLTLSKADY EKHKVYACEV
THQGLSSPVT KSFNRGEC SEQ ID NO: 48 Anti-human-05a heavy chain
QVQLVQSGAE VKKPGASVKV SCKASGYTFT DYSMDWVRQA PGQGLEWMGA
IHLNTGYTNY NQKFKGRVTM TRDTSTSTVY MELSSLRSED TAVYYCARGF
YDGYSPMDYW GQGTTVTVSS ASTKGPSVFP LAPCSRSTSE STAALGCLVK
DYFPEPVTVS WNSGALTSGV HTFPAVLQSS GLYSLSSVVT VPSSNFGTQT
YTCNVDHKP SNTKVDKTVE RKCCVECPPC PAPPVAGPSV FLFPPKPKDT
LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT
LPPSQEEMTK NQVSLTCLVK GFYPSDIAVE WESNGQPENN YKTTPPVLDS
DGSFFLYSRL TVDKSRWQEG NVFSCSVMHE ALHNHYTQKS LSLSLGK SEQ ID NO: 49
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Ser Met Asp Trp Val Arg Gln Ala Pro Gly Gln Gly Leu Glu Trp Met
        35                  40                  45
Gly Ala Ile His Leu Asn Thr Gly Tyr Thr Asn Tyr Asn Gln Lys Phe
    50                  55                  60
Lys Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
            85                  90                  95
Ala Arg Gly Phe Tyr Asp Gly Tyr Ser Pro Met Asp Tyr Trp Gly Gln
        100                 105                 110
Gly Thr Thr Val Thr Val Ser Ser Ala Ser Thr Lys Gly Pro Ser Val
    115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Asn Phe Gly Thr Gln Thr Tyr Thr Cys Asn Val Asp His Lys
    195                 200                 205
Pro Ser Asn Thr Lys Val Asp Lys Thr Val Glu Arg Lys Cys Cys Val
    210                 215                 220
Glu Cys Pro Pro Cys Pro Ala Pro Pro Val Ala Val Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser Gln Glu Asp Pro Glu Val
        260                 265                 270
Gln Phe Asn Trp Tyr Val Asp Gly Val Glu Val His Asn Ala Lys Thr
    275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
            325                 330                 335
Lys Ala Lys Gly Gln Pro Arg Glu Pro Gln Val Tyr Thr Leu Pro Pro
        340                 345                 350
Ser Gln Glu Glu Met Thr Lys Asn Gln Val Ser Leu Thr Cys Leu Val
    355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
            405                 410                 415

TABLE 4-continued

SOME NUCLEIC ACID AND AMINO ACID SEQUENCES

Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
            435                 440                 445

SEQ ID NO: 50 ScFv
DIQMTQSPSSLSASVGDRVTITCGASENIYGALNWYQQKPGKAPKLLIYGATNLADGVPSRFS
GSGSGTDFTLTISSLQPEDFATYYCQNVLNTPLTFGQGTKVEIKRTGGGGSGGGGSGGGGSQV
QLVQSGAEVKKPGASVKVSCKASGYIFSNYWIQWVRQAPGQGLEWMGEILPGSGSTEYTENFK
DRVTMTRDTSISTVYMELSSLRSEDTAVYYCARYFFGSSPNWYFDVWGQGTLVTVSS

---

What is claimed is:

1. A method of treating age-related macular degeneration (AMD) in a patient, wherein the AMD is dry (atrophic) AMD involving geographic atrophy, comprising administering an effective amount of an anti-C5a antibody comprising a light chain of the amino acid sequence of SEQ ID NO:47 and comprising a heavy chain of the amino acid sequence of SEQ ID NO:49, or an antigen-binding fragment thereof, to said patient.

2. The method of claim 1, wherein the antibody or antigen-binding fragment thereof is an anti-C5a antibody.

3. The method of claim 2, wherein the anti-C5 antibody is administered at about 30 mg/ml to about 100 mg/ml, or more.

4. The method of claim 1, wherein the antibody is humanized anti-C5a monoclonal antibody.

5. The method of claim 1, wherein the antibody, or an antigen-binding fragment thereof, is administered intravenously.

6. The method of claim 1, wherein the antibody, or an antigen-binding fragment thereof, is administered intravitreally.

7. The method of claim 6, wherein the antibody, or an antigen-binding fragment thereof, is administered at about 500 µg to about 1,500 µg per eye.

8. The method of claim 6, wherein the antibody, or an antigen-binding fragment thereof, is administered at about 0.5 mg, about 1.5 mg, about 5 mg, or about 10 mg per eye.

9. The method of claim 6, wherein the antibody, or an antigen-binding fragment thereof, is administered at about 0.5 mg to about 10 mg per eye.

10. The method of claim 1, wherein the level of γδT-cells is reduced.

11. The method of claim 1, wherein the level of Th17- and/or γδT-cells in the spleen is reduced.

12. The method of claim 1, wherein the level of IL-17 in the eye is reduced.

13. The method of claim 1, further comprising administering a second therapeutic agent to the patient.

14. The method of claim 1, wherein the patient is a human patient.

15. The method of claim 1, wherein inflammation in the eye is reduced.

16. The method of claim 1, wherein choroidal neovascularization (CNV) in the eye is reduced.

17. The method of claim 1, wherein the effective amount is one that: improves or maintains the patient's vision, decreases IL-17 level in the eye, decreases inflammation in the eye, decreases the level of γδT-cells in the eye, reduces the production of Th17- and γδT-cells in the spleen, or reduces CNV size.

* * * * *